(12) United States Patent
Smith, II et al.

(10) Patent No.: US 10,160,750 B2
(45) Date of Patent: Dec. 25, 2018

(54) DIAMIDE MACROCYCLES AS FACTOR XIA INHIBITORS

(71) Applicant: BRISTOL-MYERS SQUIBB COMPANY, Princeton, NJ (US)

(72) Inventors: Leon M. Smith, II, Somerset, NJ (US); Donald J. P. Pinto, Churchville, PA (US); James R. Corte, Yardley, PA (US); William R. Ewing, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/735,322

(22) PCT Filed: Jun. 16, 2016

(86) PCT No.: PCT/US2016/037823
§ 371 (c)(1),
(2) Date: Dec. 11, 2017

(87) PCT Pub. No.: WO2016/205482
PCT Pub. Date: Dec. 22, 2016

(65) Prior Publication Data
US 2018/0141932 A1  May 24, 2018

Related U.S. Application Data

(60) Provisional application No. 62/181,875, filed on Jun. 19, 2015.

(51) Int. Cl.
| C07D 403/14 | (2006.01) |
| C07D 401/04 | (2006.01) |
| C07D 401/14 | (2006.01) |
| C07D 403/12 | (2006.01) |
| A61P 7/02 | (2006.01) |

(52) U.S. Cl.
CPC .............. *C07D 403/14* (2013.01); *A61P 7/02* (2018.01); *C07D 401/04* (2013.01); *C07D 401/14* (2013.01); *C07D 403/12* (2013.01)

(58) Field of Classification Search
CPC .. C07D 403/12; C07D 403/14; C07D 401/04; C07D 401/14; A61P 7/02
See application file for complete search history.

(56) References Cited

U.S. PATENT DOCUMENTS

| 2012/0039848 A1 | 2/2012 | Qiu et al. |
| 2015/0203492 A1* | 7/2015 | Yang ............ C07D 401/04 514/43 |

FOREIGN PATENT DOCUMENTS

| FR | 2 944 014 | 10/2010 |
| WO | WO2004/080971 A1 | 9/2004 |
| WO | WO2004/094372 A2 | 11/2004 |
| WO | WO2005/099709 A2 | 10/2005 |
| WO | WO2005/123050 A2 | 12/2005 |
| WO | WO2005/123680 A1 | 12/2005 |
| WO | WO2006/089005 A2 | 8/2006 |
| WO | WO2007/070816 A2 | 6/2007 |
| WO | WO2007/070818 A1 | 6/2007 |
| WO | WO2007/070826 A1 | 6/2007 |
| WO | WO2006/076575 A2 | 7/2007 |
| WO | WO2008/076805 A2 | 6/2008 |
| WO | WO2008/104175 A2 | 9/2008 |
| WO | WO2008/157162 A1 | 12/2008 |
| WO | WO2009/114677 A1 | 9/2009 |
| WO | WO2011/100401 A1 | 8/2011 |
| WO | WO2011/100402 A1 | 8/2011 |
| WO | WO2013/022814 A1 | 2/2013 |
| WO | WO2013/022818 A1 | 2/2013 |
| WO | WO2013/055984 A1 | 4/2013 |

(Continued)

OTHER PUBLICATIONS

Ding, G. et al., "A novel kind of nitrogen heterocycle compound induces apoptosis of human chronic myelogenous leukemia K562 cells", Bioorganic & Medicinal Chemistry, vol. 14, pp. 3766-3774 (2006).

Krylova, et al.,"Chemistry of azacyclols .III. Hydrolysis of anhydroazacyclol salts", Zhurnal Obshchei Khimii, vol. 38(9), pp. 2046-2050 (1968).

Shkrob, A.M. et al., "A new approach to the synthesis of stable derivatives of azacyclols", Tetrahedron Letters, vol. 28, pp. 2701-2706 (1967).

Stetter, H. et al., "Macrocyclic ring systems. IV. Macrocyclic diamides from aromatic diamines", Chemische Berichte, vol. 91, pp. 677-680 (1967).

(Continued)

*Primary Examiner* — Timothy R Rozof
(74) *Attorney, Agent, or Firm* — Hong Liu

(57) ABSTRACT

The present invention provides compounds of Formula (I): or stereoisomers, tautomers, or pharmaceutically acceptable salts thereof, wherein all the variables are as defined herein. These compounds are selective factor XIa inhibitors or dual inhibitors of FXIa and plasma kallikrein. This invention also relates to pharmaceutical compositions comprising these compounds and methods of treating thromboembolic and/or inflammatory disorders using the same.

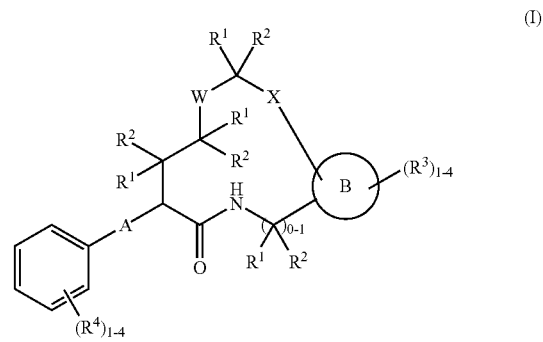

(I)

14 Claims, No Drawings

(56) References Cited

FOREIGN PATENT DOCUMENTS

| WO | WO2013/056034 A1 | 4/2013 |
| WO | WO2013/056060 A1 | 4/2013 |
| WO | WO2014/022766 A1 | 2/2014 |
| WO | WO2014/022767 A1 | 2/2014 |
| WO | WO2014/059202 A1 | 4/2014 |
| WO | WO2014/059203 A1 | 4/2014 |
| WO | WO2014/059214 A1 | 4/2014 |
| WO | WO2014/160592 A2 | 10/2014 |
| WO | WO2014/160668 A1 | 10/2014 |
| WO | WO205/116885 A1 | 8/2015 |
| WO | WO2015/116882 A1 | 8/2015 |
| WO | WO2015/116886 A1 | 8/2015 |
| WO | WO2016/036893 A1 | 3/2016 |
| WO | WO2016/053455 A1 | 4/2016 |
| WO | WO2016/205482 A1 | 12/2016 |
| WO | WO2017/019819 A1 | 2/2017 |
| WO | WO2017/019821 A1 | 2/2017 |
| WO | WO2017/023992 A1 | 2/2017 |
| WO | WO2017/151746 A1 | 9/2017 |

OTHER PUBLICATIONS

Yang, T. et al., "Copper-Catalyzed Synthesis of Medium and Large-Sized Nitrogen Heterocycles via N-Arylation of Phosphoramidates and Carbamates", Organic Letters, vol. 7(21), pp. 4781-4784 (2005).

* cited by examiner

DIAMIDE MACROCYCLES AS FACTOR XIa INHIBITORS

CROSS-REFERENCE TO RELATED APPLICATIONS

This application is a 371 application of PCT/US2016/037823 filed Jun. 16, 2016, which is entitled to priority pursuant to 35 U.S.C. § 119(e) to U.S. provisional patent application No. 62/181,875, filed on Jun. 19, 2015, which is fully incorporated herein in its entirety.

FIELD OF THE INVENTION

The present invention relates generally to novel macrocyclic compounds, and their analogues thereof, which are factor XIa inhibitors or dual inhibitors of factor XIa and plasma kallikrein, compositions containing them, and methods of using them, for example, for the treatment or prophylaxis of thromboembolic disorders, or for the treatment of retinal vascular permeability associated with diabetic retinopathy and diabetic macular edema.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

An alternative way of initiation of coagulation is operative when blood is exposed to artificial surfaces. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI.

Plasma prekallikrein is a zymogen of a trypsin-like serine protease and is present in plasma at 35 to 50 μg/mL. The gene structure is similar to that of factor XI. Overall, the amino acid sequence of plasma kallikrein has 58% homology to factor XI. Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastrointestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (Lehmann, A., "Ecallantide (DX-88), a plasma kallikrein inhibitor for the treatment of hereditary angioedema and the prevention of blood loss in on-pump cardiothoracic surgery", *Expert Opin. Biol. Ther.*, 8:1187-1199 (2008)).

The plasma kallikrein-kinin system is abnormally abundant in patients with advanced diabetic macular edema. It has been recently published that plasma kallikrein contributes to retinal vascular dysfunctions in diabetic rats (Clermont, A. et al., "Plasma kallikrein mediates retinal vascular dysfunction and induces retinal thickening in diabetic rats", *Diabetes*, 60:1590-1598 (2011)). Furthermore, administration of the plasma kallikrein inhibitor ASP-440 ameliorated both retinal vascular permeability and retinal blood flow abnormalities in diabetic rats. Therefore, a plasma kallikrein inhibitor should have utility as a treatment to reduce retinal vascular permeability associated with diabetic retinopathy and diabetic macular edema. Other complications of diabetes such as cerebral hemorrhage, nephropathy, cardiomyopathy and neuropathy, all of which have associations with plasma kallikrein may also be considered as targets for a plasma kallikrein inhibitor.

To date, no small molecule synthetic plasma kallikrein inhibitor has been approved for medical use. The large protein plasma kallikrein inhibitors present risks of anaphylactic reactions, as has been reported for Ecallantide. Thus there remains a need for compounds that inhibit plasma kallikrein, that do not induce anaphylaxis and that are orally available. Furthermore, the molecules in the known art feature a highly polar and ionizable guanidine or amidine functionality. It is well known that such functionalities may be limiting to gut permeability and therefore to oral availability.

SUMMARY OF THE INVENTION

The present invention provides novel macrocyclic compounds, their analogues, including stereoisomers, tautomers, pharmaceutically acceptable salts, or solvates thereof, which are useful as selective factor XIa inhibitors or dual inhibitors of factor XIa and plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the invention may be used in the treatment of retinal vascular permeability associated with diabetic retinopathy and diabetic macular edema.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

(I)

or stereoisomers, tautomers, pharmaceutically acceptable salts, solvates, or prodrugs thereof, wherein:

A is independently selected from

---- is an optional bond;

Ring B is independently selected from aryl and 5- to 10-membered heterocyclyl;

Q is independently selected from O, NH, and $CH_2$;

W is independently selected from $(CR^1R^2)_{1-2}$, O, NH, and $N(C_{1-4}$ alkyl);

X is independently selected from $-CR^8NH-$, $-NHC(=O)-$ and $-C(=O)NH-$; provided when W is O, NH, and $N(C_{1-4}$ alkyl), X is not $-NHC(=O)-$;

Y is independently selected from N and $CR^7$;

$R^1$ and $R^2$ are independently selected from H, halogen, $C_{1-4}$ alkyl substituted with 0-4 $R^e$, $OR^b$, and $C_{3-5}$ cycloalkyl substituted with 1-4 $R^6$;

$R^3$ is independently selected from H, $NO_2$, $=O$, halogen, $C_{1-4}$ alkyl substituted with 1-5 $R^5$, $C_{2-4}$ alkenyl substituted with 1-5 $R^5$, $C_{2-4}$ alkynyl substituted with 1-5 $R^5$, CN, $-(CH_2)_n-OR^b$, $-(CH_2)_n-NR^aR^a$, $-(CH_2)_n-C(=O)R^b$, $-(CH_2)_n-C(=O)OR^b$, $-(CH_2)_n-NR^aC(=O)OR^b$, $-(CH_2)_n-NR^aC(=O)R^b$, $-(CH_2)_n-NR^aC(N-CN)NR^aR^a$, $-(CH_2)_n-NR^aC(NH)NR^aR^a$, $-(CH_2)_n-N=CR^bNR^aR^a$, $-(CH_2)_n-NR^aC(=O)NR^aR^a$, $-(CH_2)_n-C(=O)NR^aR^a$, $-(CH_2)_n-NR^aC(=S)NR^aC(=O)R^b$, $-(CH_2)_n-S(=O)_pR^c$, $-(CH_2)_n-S(=O)_pNR^aR^a$, $-(CH_2)_n-NR^aS(=O)_pNR^aR^a$, $-(CH_2)_n-NR^aS(=O)_pR^c$, $-(CR_dR_d)_n-C_{3-10}$ carbocyclyl substituted with 1-5 $R^5$, and $-(CR_dR_d)_n$-4- to 10-membered heterocyclyl substituted with 1-5 $R^5$; optionally, two adjacent $R^3$ groups on the carbocyclyl and heterocyclyl may form a ring substituted with 1-5 $R^5$;

$R^4$ is independently selected from H, halogen, CN, $-(CH_2)_nNR^aR^a$, $C_{1-6}$ alkyl substituted with 1-5 $R^{10}$, $-(CH_2)_nOR^b$, $-(CH_2)_nC(=O)R^b$, $-(CH_2)_nC(=O)OR^b$, $-(CH_2)_n-NR^aC(=O)OR^b$, $-(CH_2)_n-NR^aC(=O)R^b$, $-(CH_2)_n-NR^aC(N-CN)NR^aR^a$, $-(CH_2)_n-NR^aC(NH)NR^aR^a$, $-(CH_2)_n-N=CR^bNR^aR^a$, $-(CH_2)_n-NR^aC(=O)NR^aR^a$, $-(CH_2)_n-C(=O)NR^aR^a$, $-(CH_2)_n-NR^aC(=S)NR^aC(=O)R^b$, $-(CH_2)_n-S(=O)_pR^c$, $-(CH_2)_n-S(=O)_pNR^aR^a$, $-(CH_2)_n-NR^aS(=O)_pNR^aR^a$, $-(CH_2)_n-NR^aS(=O)_pR^c$, $-(CH_2)_n$-aryl substituted with 1-5 $R^{10}$, $-(CH_2)_n-C_{3-6}$ cycloalkyl substituted with 1-5 $R^{10}$, and $-(CH_2)_n$-4-6 membered heterocyclyl substituted with 1-5 $R^{10}$;

$R^5$, at each occurrence, is independently selected from H, D, $-(CH_2)_n-OR^b$, $=O$, $-(CH_2)_nNH_2$, $-(CH_2)_nCN$, halogen, $C_{1-6}$ alkyl, $-(CH_2)_n-C(=O)OR^b$, $-(CH_2)_n-OR^b$, $-(CH_2)_n-C_{3-10}$ carbocyclyl substituted with 0-5 $R^e$, $-(CH_2)_n$-4- to 10-membered heterocyclyl substituted with 0-5 $R^e$, and $-O$-4- to 10-membered heterocyclyl substituted with 0-5 $R^e$;

$R^6$ is independently selected from H, OH, $=O$, $-(CH_2)_nNH_2$, $-(CH_2)_nCN$, halogen, $C_{1-6}$ alkyl, $-(CH_2)_n-C(=O)OH$, $-(CH_2)_n-C(=O)OC_{1-4}$ alkyl, $-(CH_2)_n-OC_{1-4}$ alkyl, $-(CH_2)_n-C_{3-10}$ carbocycle substituted with 0-5 $R^e$, —(CH$_2$)$_n$-4- to 10-membered heterocycle substituted with 0-5 R$^e$, and —(CH$_2$)$_n$-4- to 10-membered heterocycle substituted with 0-5 R$^e$;

R$^7$ is independently selected from H, CN, OR$^b$, halogen, NR$^a$R$^a$, and C$_{1-3}$ alkyl substituted with 0-5 R$^e$;

R$^8$ is independently selected from H, C$_{1-4}$ alkyl substituted with 0-3 R$^e$, CO$_2$H, —(CH$_2$)$_n$CO$_2$(C$_{1-4}$ alkyl), —(CH$_2$)$_n$CO$_2$NH$_2$, —CONH(C$_{1-4}$ alkoxy), —CO$_2$(CH$_2$)$_2$O(C$_{1-4}$ alkyl), —CO$_2$(CH$_2$)$_2$N(C$_{1-4}$ alkyl)$_2$, —CONH(CH$_2$)$_2$O(C$_{1-4}$ alkyl), —CONH(CH$_2$)$_2$N(C$_{1-4}$ alkyl)$_2$, —CON(C$_{1-4}$ alkyl)(CH$_2$)$_2$O(C$_{1-4}$ alkyl), —CON(C$_{1-4}$ alkyl)(CH$_2$)$_2$N(C$_{1-4}$ alkyl)$_2$, —CONHBn, —CONH(OBn), —(CO)$_{0-1}$(CH$_2$)$_{0-3}$—C$_{3-6}$ carbocycle, and —(CH$_2$)$_{0-1}$—(CO)$_{0-1}$—(V)$_{0-1}$—(CH$_2$)$_{0-2}$-(4- to 6-membered heterocycle comprising carbon atoms and 1-4 heteroatoms selected from N, NH, N(C$_{1-4}$ alkyl), O, and S(O)$_p$); wherein said carbocycle and heterocycle are substituted with 1-2 R$^9$; V is independently selected from O, NH and N(C$_{1-4}$ alkyl);

R$^9$ is independently selected from H, halogen, OH, CHF$_2$, CF$_3$, C$_{1-4}$ alkoxy, CH$_2$OH, CO$_2$H, CO$_2$(C$_{1-4}$ alkyl), CONH$_2$, and C$_{1-4}$ alkyl;

R$^{10}$, at each occurrence, is independently selected from H, halogen, CN, NO$_2$, =O, C(=O)NR$^a$R$^a$, C(=O)OR$^b$, Si(C$_{1-4}$ alkyl)$_3$, —(CH$_2$)$_n$—OR$^b$, —(CH$_2$)$_n$—NR$^a$R$^a$, C(=NOH)NH$_2$, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, aryl substituted with 0-5 R$^e$, —(CH$_2$)$_n$—C$_{3-6}$ cycloalkyl substituted with 0-5 R$^e$, —(CH$_2$)$_n$—O-4- to 10-membered heterocyclyl substituted with 0-5 R$^e$;

R$^a$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$_e$, —(CH$_2$)$_n$—C$_{3-10}$carbocyclyl substituted with 0-5 R$^e$, and —(CH$_2$)$_n$-heterocyclyl substituted with 0-5 R$^e$;

R$^c$, at each occurrence, is independently selected from C$_{1-6}$ alkyl substituted with 0-5 R$^e$, C$_{2-6}$alkenyl substituted with 0-5 R$^e$, C$_{2-6}$alkynyl substituted with 0-5 R$^e$, C$_{3-6}$carbocyclyl, and heterocyclyl;

R$^d$, at each occurrence, is independently selected from H and C$_{1-4}$alkyl substituted with 0-5 R$^e$;

R$^e$, at each occurrence, is independently selected from F, Cl, Br, CN, NO$_2$, =O, C$_{1-6}$ alkyl substituted with 0-5 R$^f$, C$_{2-6}$ alkenyl, C$_{2-6}$ alkynyl, —(CH$_2$)$_n$—C$_{3-6}$ cycloalkyl, —(CH$_2$)$_n$-aryl, —(CH$_2$)$_n$-heterocyclyl, CO$_2$H, —(CH$_2$)$_n$OR$^f$, SR$^f$, and —(CH$_2$)$_n$NR$^f$R$^f$;

R$^f$, at each occurrence, is independently selected from H, C$_{1-5}$ alkyl optionally substituted with F, Cl, Br, C$_{3-6}$ cycloalkyl, and phenyl, or R$^f$ and R$^f$ together with the nitrogen atom to which they are both attached form a heterocyclic ring optionally substituted with C$_{1-4}$alkyl;

n, at each occurrence, is an integer independently selected from 0, 1, 2, 3, and 4; and p, at each occurrence, is an integer independently selected from 0, 1, and 2.

In another aspect, the present invention provides compounds of Formula (I) or stereoisomers, tautomers, pharmaceutically acceptable salts, solvates, or prodrugs thereof, wherein:

A is independently selected from

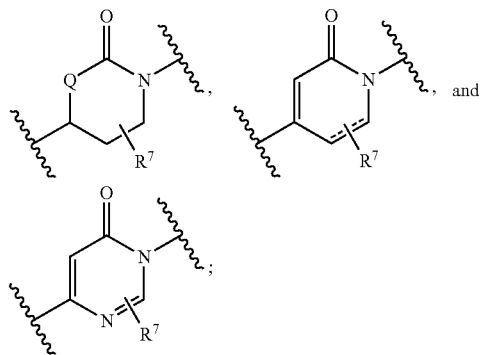

Ring B is independently selected from aryl and 5- to 6-membered heterocyclyl;

Q is independently selected from O, NH, and CH$_2$;

W is independently selected from (CR$^1$R$^2$)$_{1-2}$, O, NH, and N(C$_{1-4}$ alkyl);

X is independently selected from —CH$_2$NH—, —NHC(=O)— and —C(=O)NH—;

R$^1$ and R$^2$ are independently selected from H, halogen, C$_{1-4}$ alkyl, OR$^b$, and C$_{3-5}$ cycloalkyl;

R$^3$ is independently selected from H, NO$_2$, =O, halogen, C$_{1-4}$ alkyl substituted with 1-5 R$^5$, C$_{2-4}$ alkenyl substituted with 1-5 R$^5$, C$_{2-4}$ alkynyl substituted with 1-5 R$^5$, CN, —OR$^b$, —NR$^a$R$^a$, —C(=O)R$^b$, —C(=O)OR$^b$, —NR$^a$C(=O)OR$^b$, —NR$^a$C(=O)R$^b$, —NR$^a$C(N=CN)NHR$^a$, —NR$^a$C(NH)NHR$^a$, —N=CR$^b$NR$^a$R$^a$, —NR$^a$C(=O)NR$^a$R$^a$, —C(=O)NR$^a$R$^a$, —NR$^a$C(=S)NR$^a$C(=O)R$^b$, —S(=O)$_p$R$^c$, —S(=O)$_p$NR$^a$R$^a$, —NR$^a$S(=O)$_p$NR$^a$R$^a$, —NR$^a$S(=O)$_p$R$^c$, —(CH$_2$)$_n$—C$_{3-10}$ carbocyclyl substituted with 1-5 R$^5$, and —(CH$_2$)$_n$-4- to 10-membered heterocyclyl substituted with 1-5 R$^5$; optionally, two adjacent R$^3$ groups on the carbocyclyl and heterocyclyl may form a ring substituted with 1-5 R$^5$;

R$^4$ is independently selected from H, halogen, CN, C$_{1-6}$ alkyl substituted with 1-5 R$^{10}$, —OR$^b$, —(CH$_2$)$_n$-aryl substituted with 1-5 R$^{10}$, —(CH$_2$)$_n$—C$_{3-6}$ cycloalkyl substituted with 1-5 R$^{10}$, and —(CH$_2$)$_n$-4-6 membered heterocyclyl substituted with 1-5 R$^{10}$;

R$^5$, at each occurrence, is independently selected from H, D, —(CH$_2$)$_n$—OR$^b$, =O, —(CH$_2$)$_n$NH$_2$, —(CH$_2$)$_n$CN, halogen, C$_{1-6}$ alkyl, —(CH$_2$)$_n$—C(=O)OR$^b$, —(CH$_2$)$_n$—OR$^b$, —(CH$_2$)$_n$—C$_{3-10}$ carbocyclyl substituted with 0-5 R$^e$, —(CH$_2$)$_n$-4- to 10-membered heterocyclyl substituted with 0-5 R$^e$, and —O-4- to 10-membered heterocyclyl substituted with 0-5 R$^e$;

R$^7$ is independently selected from H, OR$^b$, halogen, NR$^a$R$^a$, and C$_{1-3}$ alkyl;

R$^{10}$, at each occurrence, is independently selected from H, halogen, CN, NO$_2$, =O, C(=O)NR$^a$R$^a$, C(=O)OR$^b$, Si(C$_{1-4}$ alkyl)$_3$, —(CH$_2$)$_n$—OR$^b$, —(CH$_2$)$_n$—NR$^a$R$^a$, C(=NOH)NH$_2$, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, aryl substituted with 0-5 R$^e$, —(CH$_2$)$_n$—C$_{3-6}$ cycloalkyl substituted with 0-5 R$^e$, —(CH$_2$)$_n$—O-4- to 10-membered heterocyclyl substituted with 0-5 R$^e$;

R$^a$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R_e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^e$, at each occurrence, is independently selected from F, Cl, Br, CN, $NO_2$, =O, $C_{1-6}$ alkyl substituted with 0-5 $R^f$, $C_{2-6}$ alkenyl, $C_{2-6}$ alkynyl, —$(CH_2)_n$—$C_{3-6}$ cycloalkyl, —$(CH_2)_n$-aryl, —$(CH_2)_n$-heterocyclyl, $CO_2H$, —$(CH_2)_n$ $OR^f$, $SR^f$, and —$(CH_2)_n NR^f R^f$;

$R^f$, at each occurrence, is independently selected from H, $C_{1-5}$ alkyl optionally substituted with F, Cl, Br, $C_{3-6}$ cycloalkyl, and phenyl, or $R^f$ and $R^f$ together with the nitrogen atom to which they are both attached form a heterocyclic ring optionally substituted with $C_{1-4}$alkyl;

n, at each occurrence, is an integer independently selected from 0, 1, 2, 3, and 4; and p, at each occurrence, is an integer independently selected from 0, 1, and 2.

In another aspect, the present invention provides compounds of Formula (II):

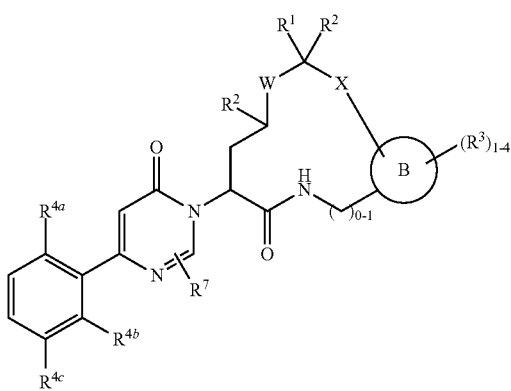

(II)

or stereoisomers, tautomers, pharmaceutically acceptable salts, solvates, or prodrugs thereof, wherein:

Ring B is independently selected from aryl and 5- to 6-membered heterocyclyl;

W is independently selected from $(CHR^{1a})_{1-2}$, O, NH, and $N(C_{1-4}$ alkyl);

X is independently selected from —NHC(=O)— and —C(=O)NH—;

$R^1$ is independently selected from H and $C_{1-4}$ alkyl;

$R^{1a}$ is independently selected from H, F, $CH_3$, and OH;

$R^2$ is independently selected from H and OH;

$R^3$ is independently selected from H, =O, halogen, $C_{1-4}$ alkyl substituted with 1-5 $R^5$, CN, —$OR^b$, —$NR^a R^a$, —C(=O)$R^b$, —C(=O)$OR^b$, —$NR^a C$(=O)$OR^b$, —$NR^a C$(=O)$R^b$, —$NR^a C$(=O)$NR^a R^a$, —C(=O)$NR^a R^a$, —S(=O)$_p R^c$, —$(CH_2)_n$—$C_{3-10}$ carbocyclyl substituted with 1-5 $R^5$, and —$(CH_2)_n$-4- to 10-membered heterocyclyl substituted with 1-5 $R^5$; optionally, two adjacent $R^3$ groups on the carbocyclyl and heterocyclyl may form a ring substituted with 1-5 $R^5$;

$R^{4a}$ is independently selected from H, halogen, CN, $OCH_3$, $OCF_3$, $CH_3$, C(=O)$CH_3$, $CHF_2$, $CF_3$, $CCH_3F_2$, $OCHF_2$, aryl, $C_{3-6}$ cycloalkyl, and 4-6 membered heterocycle, wherein said aryl, cycloalkyl and heterocycle is optionally substituted with $R^{10}$;

$R^{4b}$ is independently selected from H and halogen;

$R^{4c}$ is independently selected from H, F, Cl, methyl, ethyl, isopropyl, and $OCH_3$;

$R^5$, at each occurrence, is independently selected from H, D, —$(CH_2)_n$—$OR^b$, =O, —$(CH_2)_n NH_2$, —$(CH_2)_n CN$, halogen, $C_{1-6}$ alkyl, —$(CH_2)_n$—C(=O)$OR^b$, —$(CH_2)_n$—$OR^b$, —$(CH_2)_n$—$C_{3-10}$ carbocyclyl substituted with 0-5 $R^e$, —$(CH_2)_n$-4- to 10-membered heterocyclyl substituted with 0-5 $R^e$, and —O-4- to 10-membered heterocyclyl substituted with 0-5 $R^e$;

$R^7$ is independently selected from H, $OR^b$, halogen, $NR^a R^a$, and $C_{1-3}$ alkyl;

$R^{10}$, at each occurrence, is independently selected from H, halogen, CN, $NO_2$, =O, C(=O)$NR^a R^a$, C(=O)$OR^b$, $Si(C_{1-4}$ alkyl)$_3$, —$(CH_2)_n$—$OR^b$, —$(CH_2)_n$—$NR^a R^a$, C(=NOH)$NH_2$, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, aryl substituted with 0-5 $R^e$, —$(CH_2)_n$—$C_{3-6}$ cycloalkyl substituted with 0-5 $R^e$, —$(CH_2)_n$—O-4- to 10-membered heterocyclyl substituted with 0-5 $R^e$;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R_e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^e$, at each occurrence, is independently selected from F, Cl, Br, CN, $NO_2$, =O, $C_{1-6}$ alkyl substituted with 0-5 $R^f$, $C_{2-6}$ alkenyl, $C_{2-6}$ alkynyl, —$(CH_2)_n$—$C_{3-6}$ cycloalkyl, —$(CH_2)_n$-aryl, —$(CH_2)_n$-heterocyclyl, $CO_2H$, —$(CH_2)_n$ $OR^f$, $SR^f$, and —$(CH_2)_n NR^f R^f$;

$R^f$, at each occurrence, is independently selected from H, $C_{1-5}$ alkyl optionally substituted with F, Cl, Br, $C_{3-6}$ cycloalkyl, and phenyl, or $R^f$ and $R^f$ together with the nitrogen atom to which they are both attached form a heterocyclic ring optionally substituted with $C_{1-4}$alkyl;

n, at each occurrence, is an integer independently selected from 0, 1, 2, 3, and 4; and p, at each occurrence, is an integer independently selected from 0, 1, and 2.

In another aspect, the present invention provides compounds of Formula (II), or stereoisomers, tautomers, pharmaceutically acceptable salts, solvates, or prodrugs thereof, wherein:

ring B is independently selected from

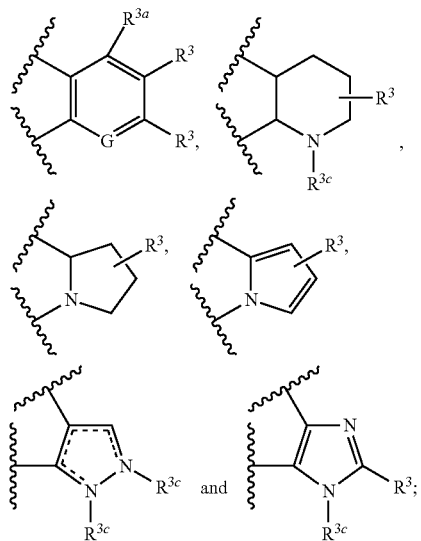

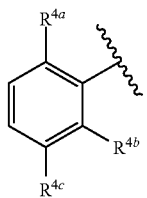

is independently selected from

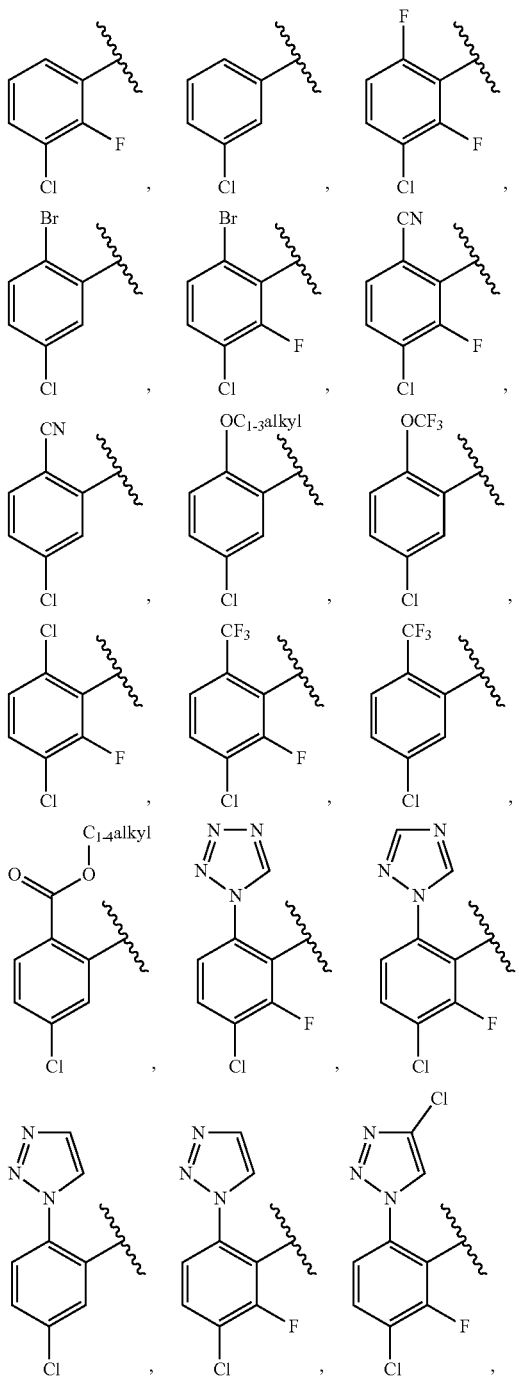

G is independently selected from N and CR$^{3b}$;

R$^3$ is independently selected from H, =O, halogen, C$_{1-4}$ alkyl substituted with 1-5 R$^5$, CN, —OR$^b$, —NR$^a$R$^a$, —C(=O)R$^b$, —C(=O)OR$^b$, —NR$^a$C(=O)OR$^b$, NR$^a$C(=O)R$^b$, —NR$^a$C(=O)NR$^a$R$^a$, —C(=O)NR$^a$R$^a$, —S(=O)$_p$R$^c$, —(CH$_2$)$_n$—C$_{3-10}$ carbocyclyl substituted with 1-5 R$^5$, and —(CH$_2$)$_n$-4- to 10-membered heterocyclyl substituted with 1-5 R$^5$;

R$^{3a}$ is independently selected from H and halogen;

R$^{3b}$ is independently selected from H, halogen, methyl, and CN;

R$^{3c}$ is independently selected from H, C$_{1-4}$alkyl substituted with 1-4 R$^5$, —(CH$_2$)$_n$—C(=O)R$^b$, —(CH$_2$)$_n$—C(=O)OR$^b$; provided when one R$^{3c}$ is present, the other is absent;

R$^{4a}$ is independently selected from H, F, Cl, Br, CN, OCH$_3$, OCF$_3$, CH$_3$, C(=O)CH$_3$, CHF$_2$, CF$_3$, CCH$_3$F$_2$, OCHF$_2$, phenyl, C$_{3-6}$ cycloalkyl, and 4-6 membered heterocycle, wherein said phenyl, cycloalkyl and heterocycle is optionally substituted with R$^{10}$;

R$^{4b}$ is independently selected from H and F;

R$^{4c}$ is independently selected from H, F, Cl, methyl, ethyl, isopropyl, and OCH$_3$;

R$^5$, at each occurrence, is independently selected from H, D, —OR$^b$, —NH$_2$, —CN, halogen, C$_{1-6}$ alkyl, —C(=O)OR$^b$, C$_{3-10}$ carbocyclyl substituted with 0-5 R$^e$, -4- to 10-membered heterocyclyl substituted with 0-5 R$^e$, and —O-4- to 10-membered heterocyclyl substituted with 0-5 R$^e$; and R$^{10}$, at each occurrence, is independently selected from H, halogen, CN, NO$_2$, =O, C(=O)NR$^a$R$^a$, C(=O)OR$^b$, Si(C$_{1-4}$ alkyl)$_3$, —(CH$_2$)$_n$—OR$^b$, —(CH$_2$)$_n$—NR$^a$R$^a$, C(=NOH)NH$_2$, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, aryl substituted with 0-5 R$^e$, —(CH$_2$)$_n$—C$_{3-6}$ cycloalkyl substituted with 0-5 R$^e$, —(CH$_2$)$_n$—O-4- to 10-membered heterocyclyl substituted with 0-5 R$^e$;

other variables are as defined in Formula (II) above.

In another aspect, the present invention provides compounds of Formula (II), or stereoisomers, tautomers, pharmaceutically acceptable salts, solvates, or prodrugs thereof, wherein:

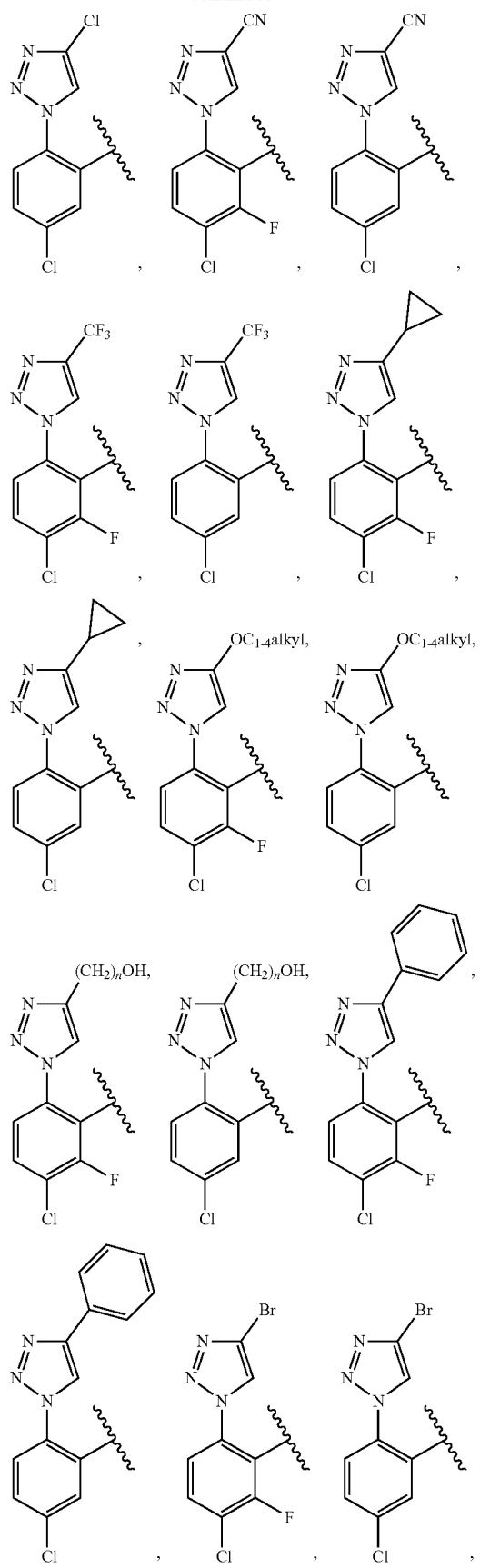
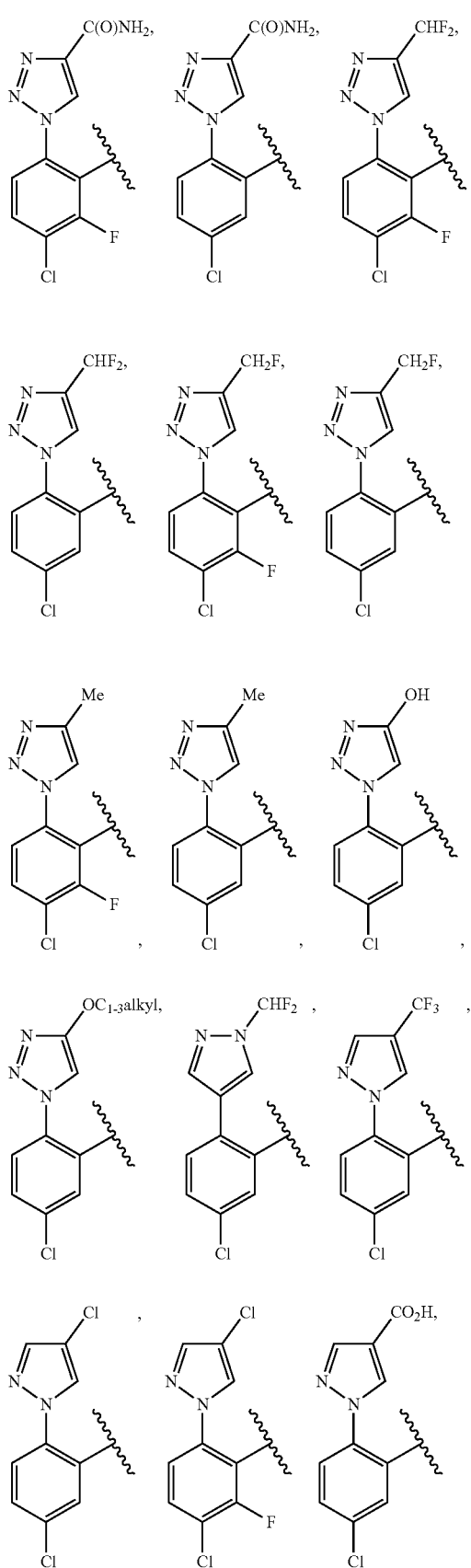

-continued

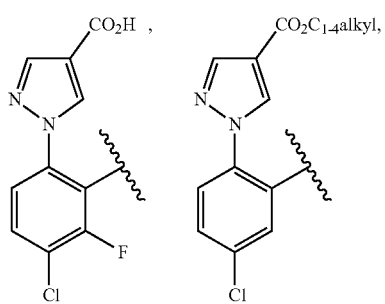

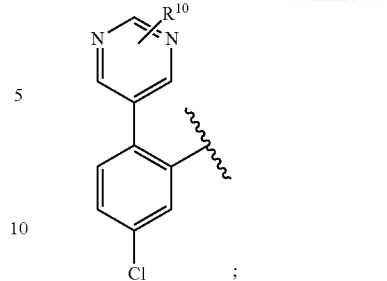

other variables are as defined in Formula (II) above.

In another aspect, the present invention provides compounds of Formula (III):

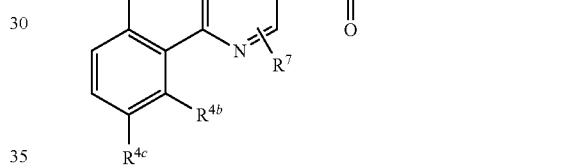

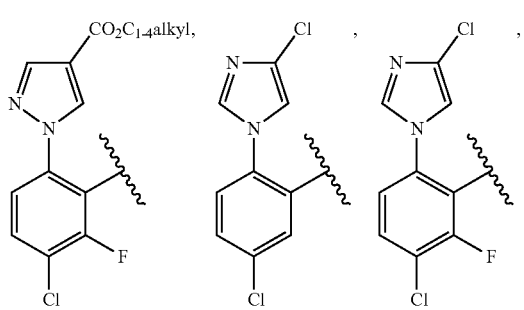

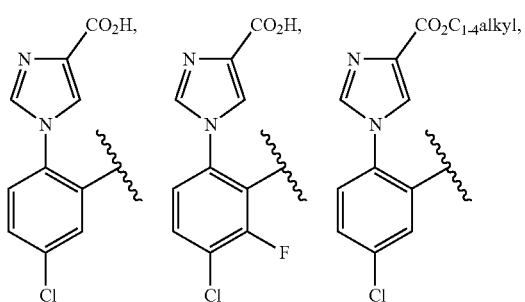

or stereoisomers, tautomers, pharmaceutically acceptable salts, solvates, or prodrugs thereof, wherein:

G is independently selected from N and $CR^{3b}$;

$R^1$ is independently selected from H and $CH_3$;

$R^{1a}$ is independently selected from H, F, $CH_3$, and OH;

$R^2$ is independently selected from H and OH;

$R^{3a}$ is independently selected from H and halogen;

$R^{3b}$ is independently selected from H, halogen, methyl, and CN;

$R^3$ is independently selected from H, halogen, $C_{1-4}$ alkyl substituted with 1-5 $R^5$, CN, —$OR^b$, —$NR^aR^a$, —C(=O)$R^b$, —C(=O)$OR^b$, —$NR^aC$(=O)$OR^b$, $NR^aC$(=O)$R^b$, —$NR^aC$(=O)$NR^aR^a$, —C(=O)$NR^aR^a$, —S(=O)$_pR^c$, —$(CH_2)_n$—$C_{3-10}$ carbocyclyl substituted with 1-5 $R^5$, and —$(CH_2)_n$-4- to 10-membered heterocyclyl substituted with 1-5 $R^5$;

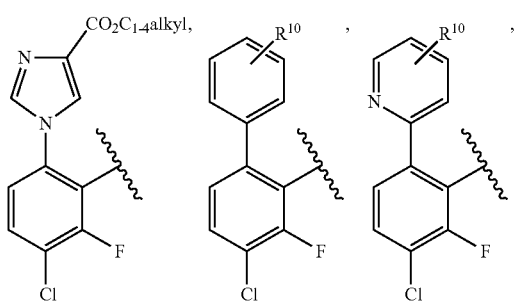

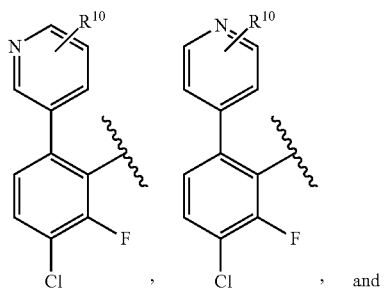, and 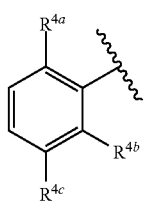

is independently selected from
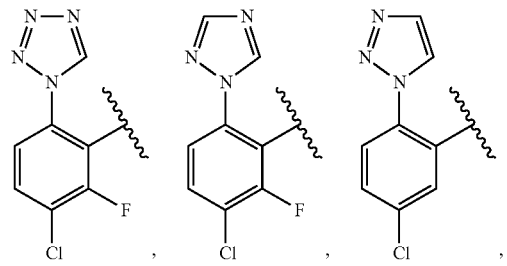
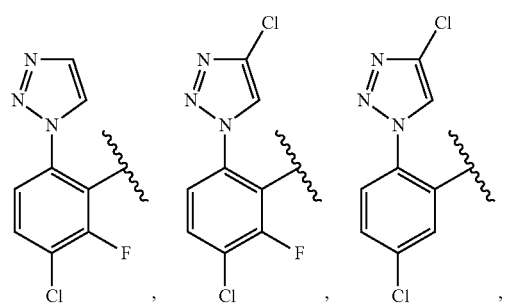
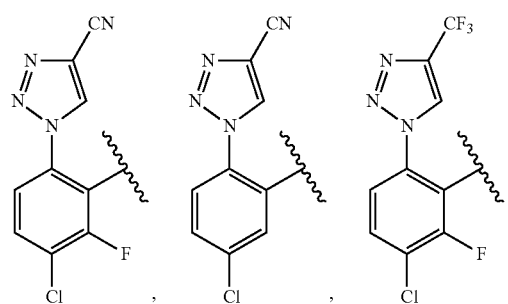
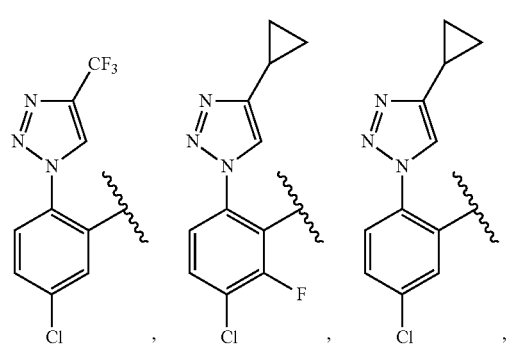
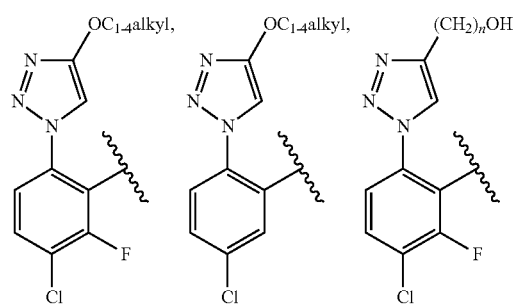
-continued
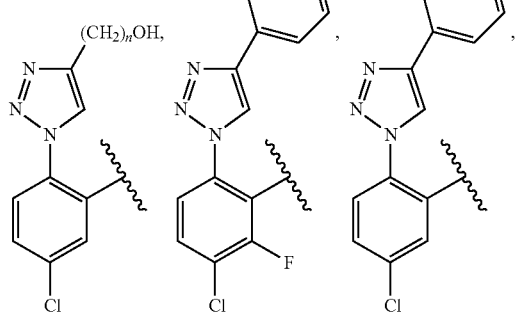
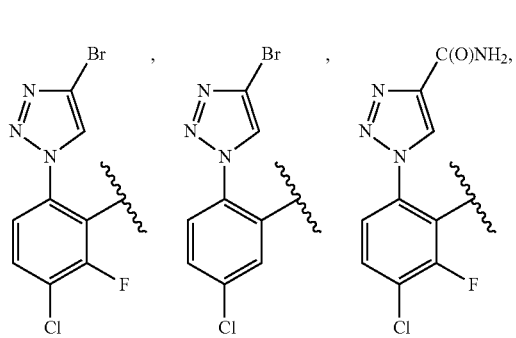
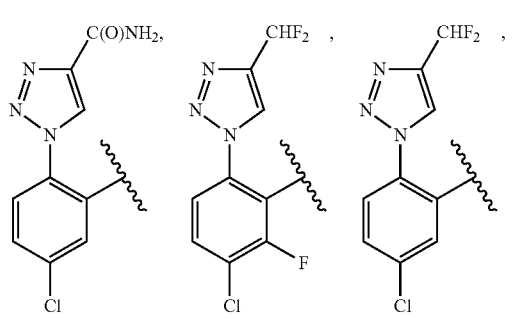
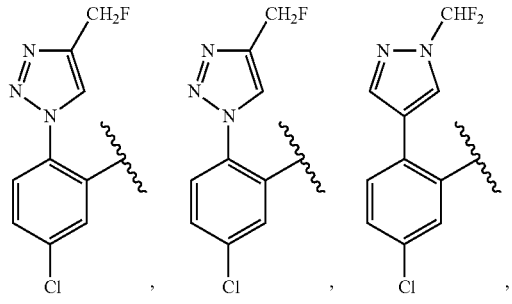
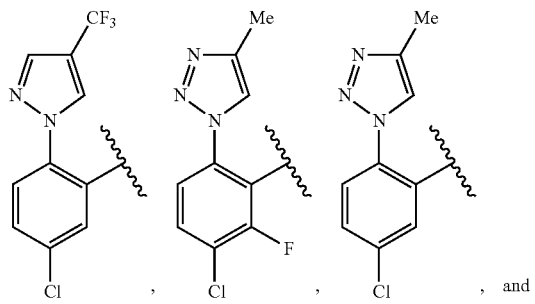
and -continued

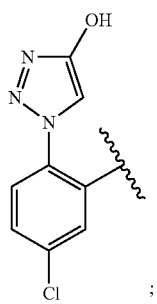

R⁵, at each occurrence, is independently selected from H, D, —OR$^b$, —NH$_2$, —CN, halogen, C$_{1-6}$ alkyl, —C(=O)OR$^b$, C$_{3-10}$ carbocyclyl substituted with 0-5 R$^e$, -4- to 10-membered heterocyclyl substituted with 0-5 R$^e$, and —O-4- to 10-membered heterocyclyl substituted with 0-5 R$^e$;

R⁷ is independently selected from H, OH, halogen, NR$^a$R$^a$, and C$_{1-3}$ alkyl;

R$^a$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$_e$, —(CH$_2$)$_n$—C$_{3-10}$carbocyclyl substituted with 0-5 R$^e$, and —(CH$_2$)$_n$-heterocyclyl substituted with 0-5 R$^e$;

R$^c$, at each occurrence, is independently selected from C$_{1-6}$ alkyl substituted with 0-5 R$^e$, C$_{2-6}$alkenyl substituted with 0-5 R$^e$, C$_{2-6}$alkynyl substituted with 0-5 R$^e$, C$_{3-6}$carbocyclyl, and heterocyclyl;

R$^e$, at each occurrence, is independently selected from F, Cl, Br, CN, NO$_2$, =O, C$_{1-6}$ alkyl substituted with 0-5 R$^f$, C$_{2-6}$ alkenyl, C$_{2-6}$ alkynyl, —(CH$_2$)$_n$—C$_{3-6}$ cycloalkyl, —(CH$_2$)$_n$-aryl, —(CH$_2$)$_n$-heterocyclyl, CO$_2$H, —(CH$_2$)$_n$OR$^f$, SR$^f$, and —(CH$_2$)$_n$NR$^f$R$^f$;

R$^f$, at each occurrence, is independently selected from H, C$_{1-5}$ alkyl optionally substituted with F, Cl, Br, C$_{3-6}$ cycloalkyl, and phenyl, or R$^f$ and R$^f$ together with the nitrogen atom to which they are both attached form a heterocyclic ring optionally substituted with C$_{1-4}$alkyl;

n, at each occurrence, is an integer independently selected from 0, 1, 2, 3, and 4;

p, at each occurrence, is an integer independently selected from 0, 1, and 2.

In another aspect, the present invention provides compounds of Formula (III), or stereoisomers, tautomers, pharmaceutically acceptable salts, solvates, or prodrugs thereof, wherein:

G is CR$^{3b}$;
R$^1$ is independently selected from H and CH$_3$;
R$^{1a}$ is independently selected from H, F, CH$_3$, and OH;
R$^2$ is independently selected from H and OH;
R$^{3a}$ is H;
R$^{3b}$ is independently selected from H, halogen, methyl, and CN;
R$^3$ is independently selected from H, =O, F, CHF$_2$, CF$_3$, OCF$_3$, OCHF$_2$, CH$_3$, CN, —(CH$_2$)$_{0-2}$—OH, OC$_{1-4}$ alkyl, C(=O)C$_{1-4}$ alkyl, —(CH$_2$)$_{0-1}$—C(=O)OH, —C(=O)OC$_{1-4}$ alkyl, —S(=O)$_2$C$_{1-4}$ alkyl, and —NHC(=O)OC$_{1-4}$ alkyl;

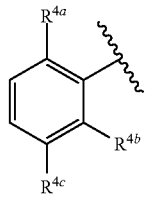

is independently selected from

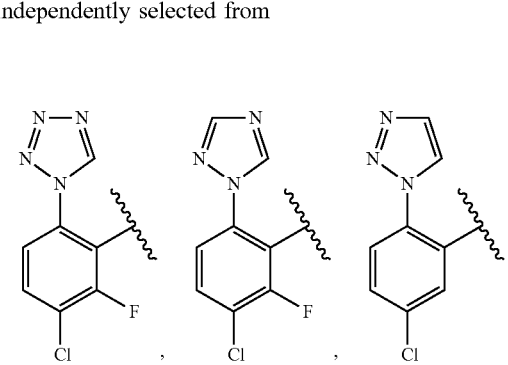

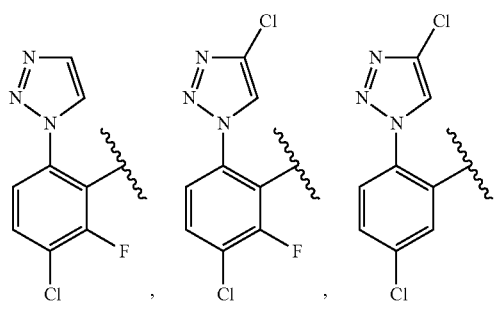

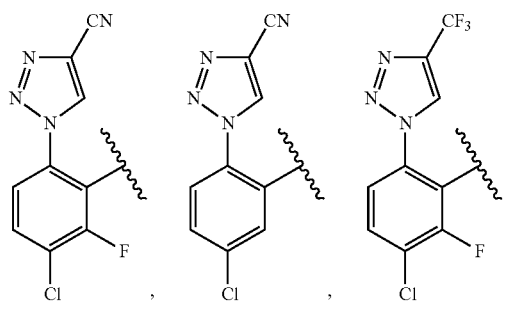

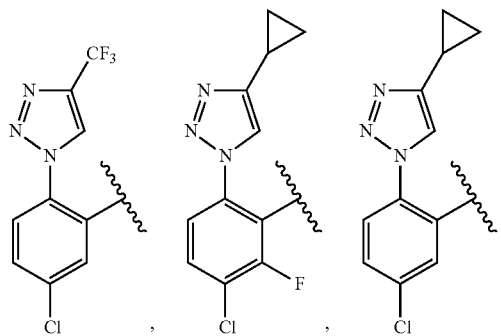

-continued

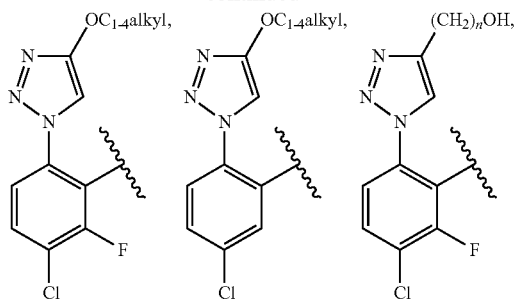
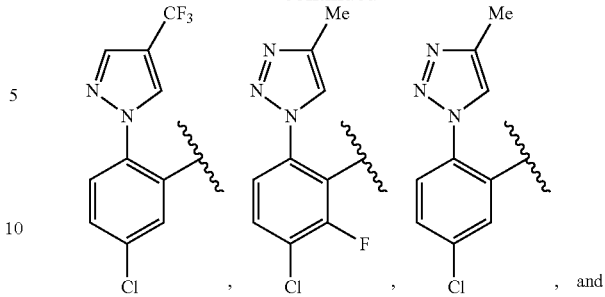

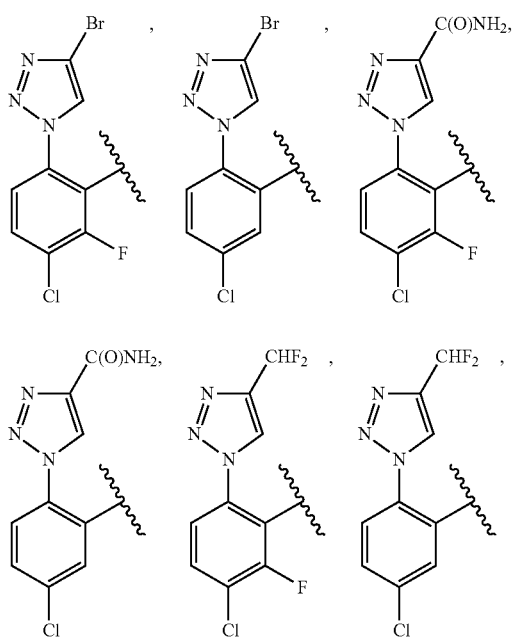
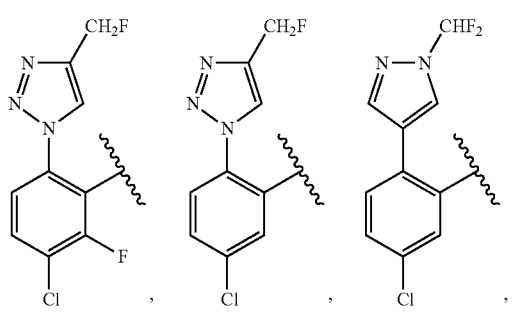

R⁷ is independently selected from H, OH, halogen, and $C_{1-3}$ alkyl;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R_e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^e$, at each occurrence, is independently selected from F, Cl, Br, CN, $NO_2$, =O, $C_{1-6}$ alkyl substituted with 0-5 $R^f$, $C_{2-6}$ alkenyl, $C_{2-6}$ alkynyl, —$(CH_2)_n$—$C_{3-6}$ cycloalkyl, —$(CH_2)_n$-aryl, —$(CH_2)_n$-heterocyclyl, $CO_2H$, —$(CH_2)_nOR^f$, $SR^f$, and —$(CH_2)_nNR^fR^f$;

$R^f$, at each occurrence, is independently selected from H, $C_{1-5}$ alkyl optionally substituted with F, Cl, Br, $C_{3-6}$ cycloalkyl, and phenyl, or $R^f$ and $R^f$ together with the nitrogen atom to which they are both attached form a heterocyclic ring optionally substituted with $C_{1-4}$alkyl;

n, at each occurrence, is an integer independently selected from 0, 1, 2, 3, and 4; and p, at each occurrence, is an integer independently selected from 0, 1, and 2.

In another aspect, the present invention provides compounds of Formula (II), or stereoisomers, tautomers, pharmaceutically acceptable salts, solvates, or prodrugs thereof, wherein:

G is $CR^{3b}$;
$R^1$ is independently selected from H and $CH_3$;
$R^{1a}$ is H;
$R^2$ is H;
$R^{3a}$ is H;
$R^{3b}$ is H;

R[3] is independently selected from H, F, Cl, CN, C$_{1-4}$alkyl substituted with 1-4 R[5], C(=O)R$^b$, C(=O)OR$^b$, —S(=O)$_2$R$^c$, and —NHC(=O)OR$^b$;
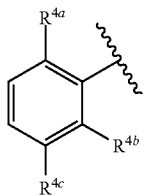
is independently selected from
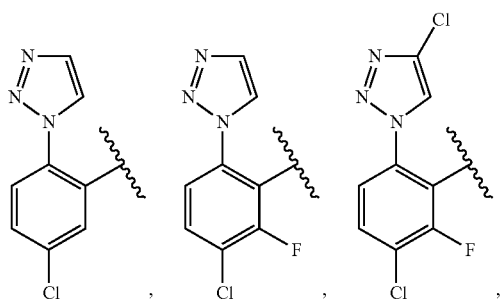
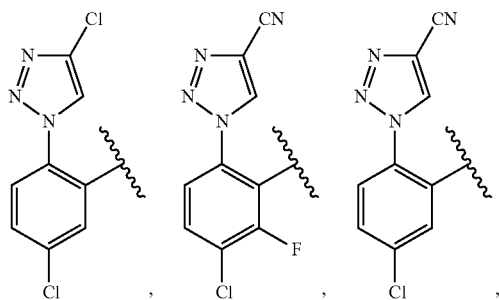
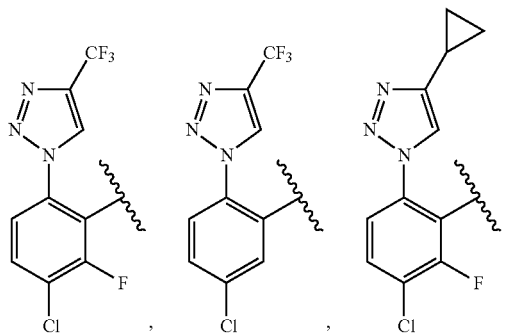
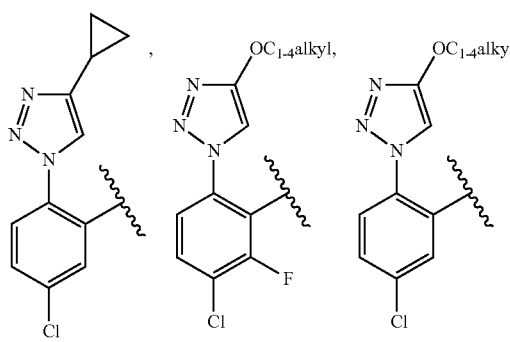
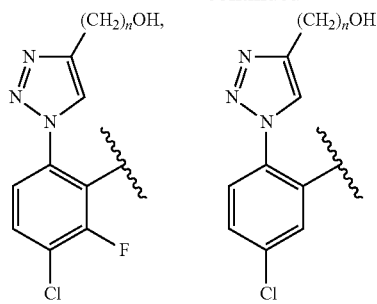
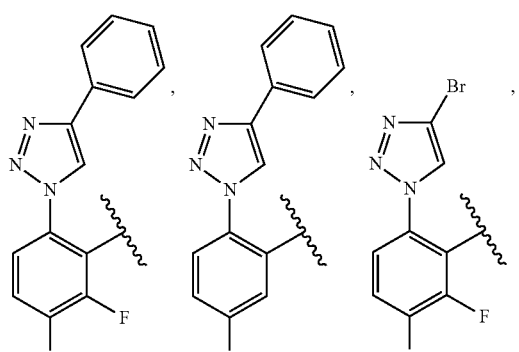
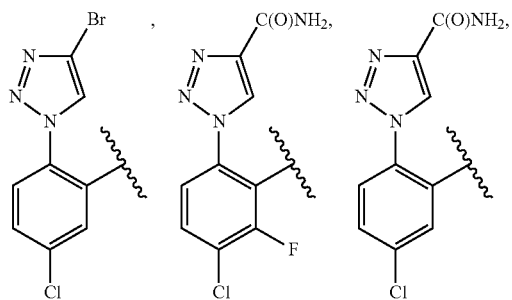
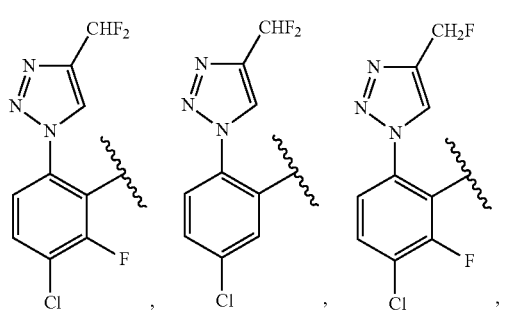
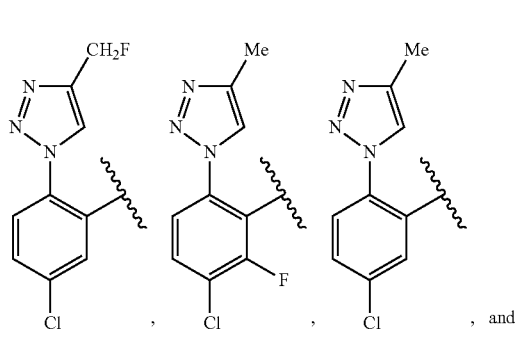
, and -continued

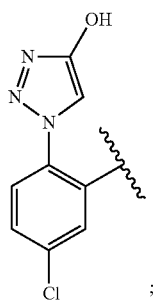 [SMILES: *c1cc(Cl)ccc1-n1cc(O)nn1]

R⁵, at each occurrence, is independently selected from H, D, —OR$^b$, —NH$_2$, —CN, halogen, C$_{1-6}$ alkyl, —C(=O)OR$^b$, C$_{3-10}$ carbocyclyl substituted with 0-5 R$^e$, -4- to 10-membered heterocyclyl substituted with 0-5 R$^e$, and —O-4- to 10-membered heterocyclyl substituted with 0-5 R$^e$;

R⁷ is H;

R$^b$, at each occurrence, is independently selected from H and C$_{1-6}$ alkyl substituted with 0-5 R$^e$;

R$^c$, at each occurrence, is C$_{1-6}$ alkyl substituted with 0-5 R$^e$;

R$^e$, at each occurrence, is independently selected from F, Cl, Br, CN, NO$_2$, =O, C$_{1-6}$ alkyl substituted with 0-5 R$^f$, C$_{2-6}$ alkenyl, C$_{2-6}$ alkynyl, —(CH$_2$)$_n$—C$_{3-6}$ cycloalkyl, —(CH$_2$)$_n$-aryl, —(CH$_2$)$_n$-heterocyclyl, CO$_2$H, —(CH$_2$)$_n$OR$^f$, SR$^f$, and —(CH$_2$)$_n$NR$^f$R$^f$;

R$^f$, at each occurrence, is independently selected from H, C$_{1-5}$ alkyl optionally substituted with F, Cl, Br, C$_{3-6}$ cycloalkyl, and phenyl;

n, at each occurrence, is an integer independently selected from 0, 1, 2, 3, and 4; and p, at each occurrence, is an integer independently selected from 0, 1, and 2.

In another aspect, the present invention provides compounds of Formula (IV):

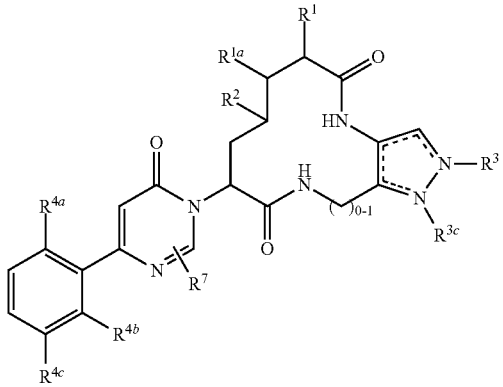

(IV)

or stereoisomers, tautomers, pharmaceutically acceptable salts, solvates, or prodrugs thereof, wherein:

--- is an optional bond;

R¹ is independently selected from H and CH$_3$;

R$^{1a}$ is independently selected from H, F, CH$_3$, and OH;

R² is independently selected from H and OH;

R$^{3c}$ is independently selected from H, and C$_{1-4}$ alkyl substituted with 1-4 R⁵; provided when one R$^{3c}$ is present, the other is absent;

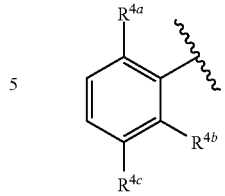

is independently selected from

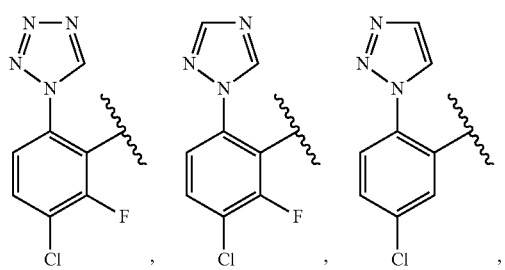

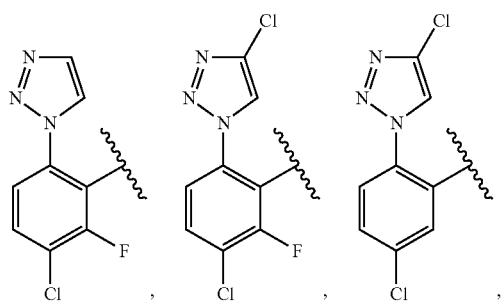

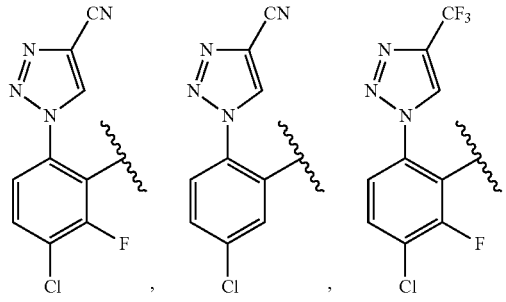

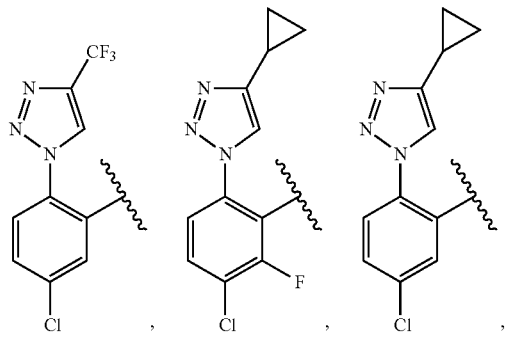

-continued

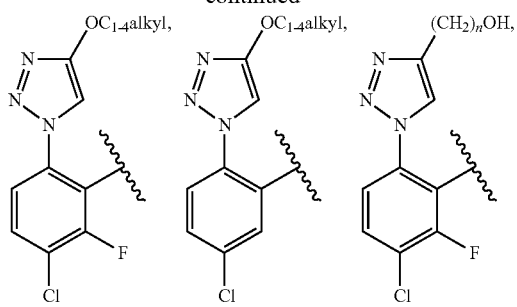

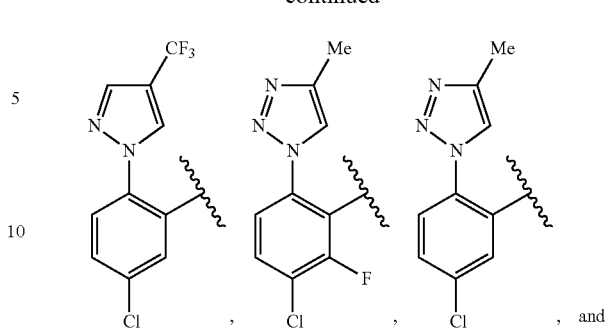

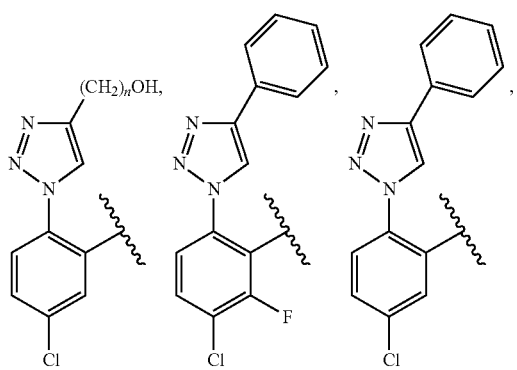

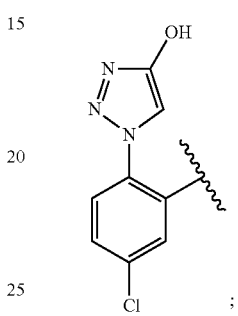

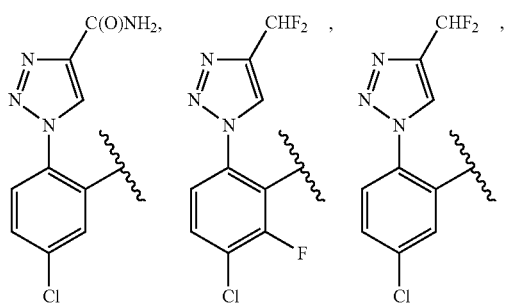

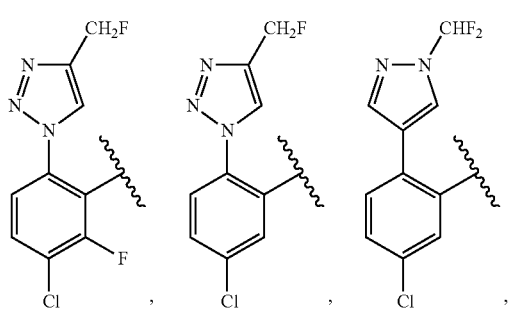

$R^5$, at each occurrence, is independently selected from H, D, —$OR^b$, —$NH_2$, —CN, F, Cl, Br, $C_{1-6}$ alkyl, —C(=O)$OR^b$, $C_{3-10}$ carbocyclyl substituted with 0-5 $R^e$, -4- to 10-membered heterocyclyl substituted with 0-5 $R^e$, and —O-4- to 10-membered heterocyclyl substituted with 0-5 $R^e$;

$R^7$ is independently selected from H, $OR^b$, halogen, $NR^aR^a$, and $C_{1-3}$ alkyl;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R_e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^e$, at each occurrence, is independently selected from F, Cl, Br, CN, $NO_2$, =O, $C_{1-6}$ alkyl substituted with 0-5 $R^f$, $C_{2-6}$ alkenyl, $C_{2-6}$ alkynyl, —$(CH_2)_n$—$C_{3-6}$ cycloalkyl, —$(CH_2)_n$-aryl, —$(CH_2)_n$-heterocyclyl, $CO_2H$, —$(CH_2)_n$$OR^f$, $SR^f$, and —$(CH_2)_nNR^fR^f$;

$R^f$, at each occurrence, is independently selected from H, $C_{1-5}$ alkyl optionally substituted with F, Cl, Br, $C_{3-6}$ cycloalkyl, and phenyl, or $R^f$ and $R^f$ together with the nitrogen atom to which they are both attached form a heterocyclic ring optionally substituted with $C_{1-4}$alkyl; and n, at each occurrence, is an integer independently selected from 0, 1, 2, 3, and 4.

In another aspect, the present invention provides compounds of Formula (V):

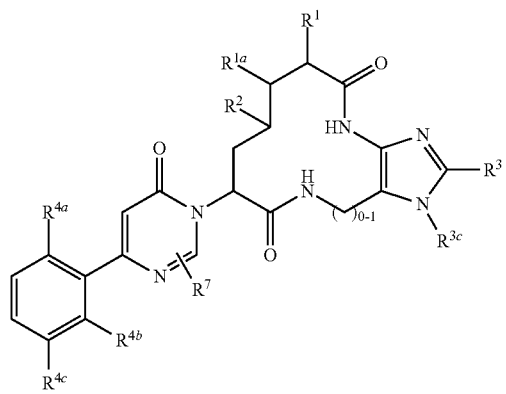

(V)

or stereoisomers, tautomers, pharmaceutically acceptable salts, solvates, or prodrugs thereof, wherein:

$R^1$ is independently selected from H and $CH_3$;

$R^{1a}$ is independently selected from H, F, $CH_3$, and OH;

$R^2$ is independently selected from H and OH;

$R^{3c}$ is independently selected from H, $C_{1-4}$alkyl substituted with 1-4 $R^5$, —$(CH_2)_n$—C(=O)$R^b$, —$(CH_2)_n$—C(=O)O$R^b$; provided when one $R^{3c}$ is present, the other is absent;

$R^3$ is independently selected from H, halogen, $C_{1-4}$ alkyl substituted with 1-5 $R^5$, CN, —O$R^b$, —N$R^aR^a$, —C(=O)$R^b$, —C(=O)O$R^b$, —N$R^a$C(=O)O$R^b$, —N$R^a$C(=O)$R^b$, —N$R^a$C(=O)N$R^aR^a$, —C(=O)N$R^aR^a$, —S(=O)$_pR^c$, —$(CH_2)_n$—$C_{3-10}$ carbocyclyl substituted with 1-5 $R^5$, and —$(CH_2)_n$-4- to 10-membered heterocyclyl substituted with 1-5 $R^5$;

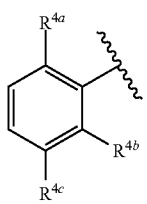

is independently selected from

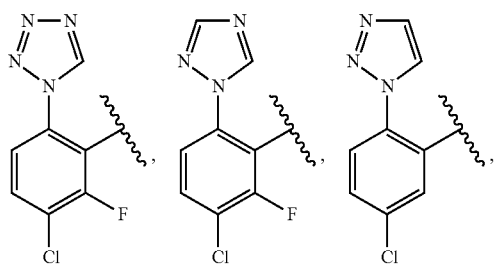

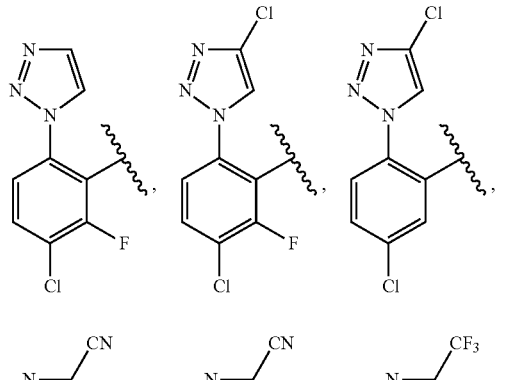

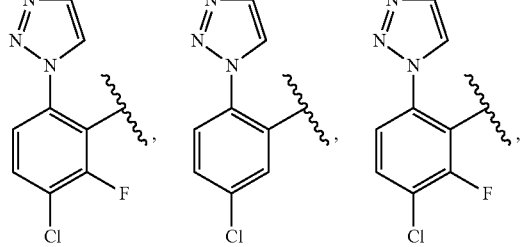

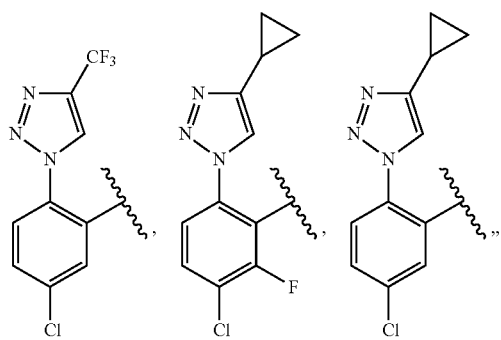

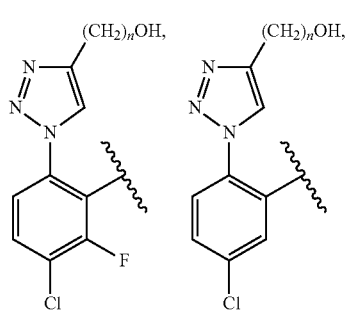

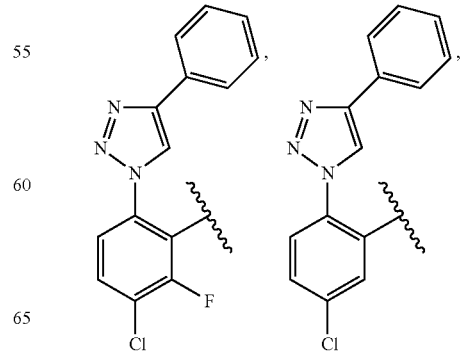

-continued

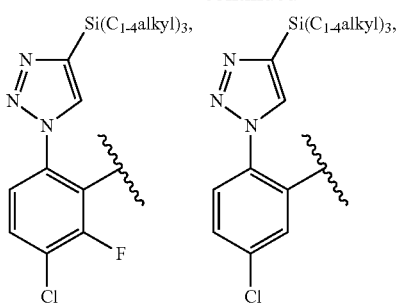

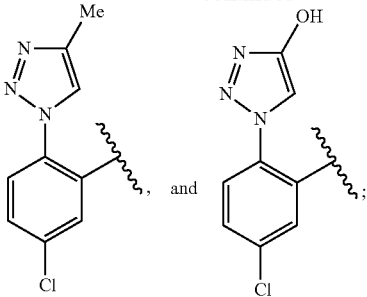

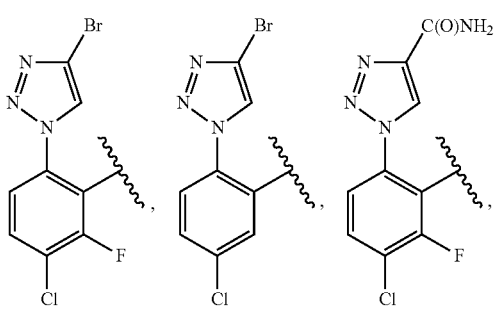

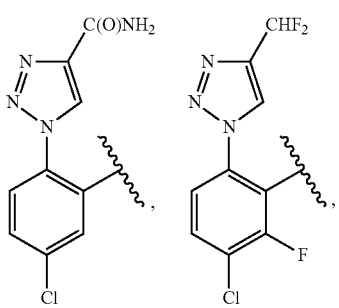

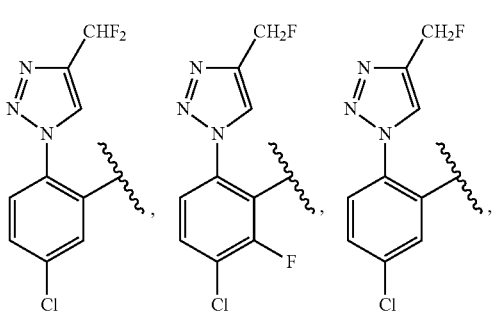

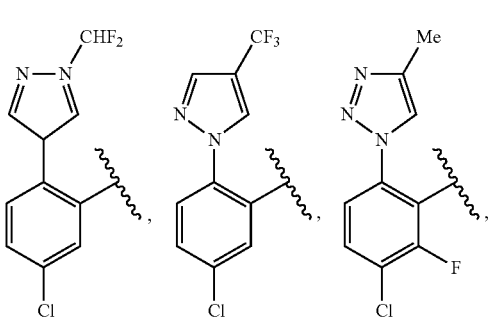

$R^5$, at each occurrence, is independently selected from H, —$OR^b$, —$NH_2$, —CN, halogen, $C_{1-6}$ alkyl, —$C(\!=\!O)OR^b$, $C_{3-10}$ carbocyclyl substituted with 0-5 $R^e$, -4- to 10-membered heterocyclyl substituted with 0-5 $R^e$, and —O-4- to 10-membered heterocyclyl substituted with 0-5 $R^e$;

$R^7$ is independently selected from H, $OR^b$, halogen, $NR^aR^a$, and $C_{1-3}$ alkyl;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R_e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^e$, at each occurrence, is independently selected from F, Cl, Br, CN, $NO_2$, =O, $C_{1-6}$ alkyl substituted with 0-5 $R^f$, $C_{2-6}$ alkenyl, $C_{2-6}$ alkynyl, —$(CH_2)_n$—$C_{3-6}$ cycloalkyl, —$(CH_2)_n$-aryl, —$(CH_2)_n$-heterocyclyl, $CO_2H$, —$(CH_2)_n$$OR^f$, $SR^f$, and —$(CH_2)_nNR^fR^f$;

$R^f$, at each occurrence, is independently selected from H, $C_{1-5}$ alkyl optionally substituted with F, Cl, Br, $C_{3-6}$ cycloalkyl, and phenyl, or $R^f$ and $R^f$ together with the nitrogen atom to which they are both attached form a heterocyclic ring optionally substituted with $C_{1-4}$alkyl; and n, at each occurrence, is an integer independently selected from 0, 1, 2, 3, and 4.

In another embodiment, the compounds of the present invention have Factor XIa or plasma kallikrein Ki values ≤10 μM.

In another embodiment, the compounds of the present invention have Factor XIa or plasma kallikrein Ki values ≤1 μM.

In another embodiment, the compounds of the present invention have Factor XIa or plasma kallikrein Ki values ≤0.5 μM.

In another embodiment, the compounds of the present invention have Factor XIa or plasma kallikrein Ki values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a factor Xa inhibitor such as apixaban, rivaroxaban, betrixaban, edoxaban, an anti-coagulant agent, an anti-platelet agent, a thrombin inhibiting agent such as dabigatran, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, eribaxaban, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a method for the prophylaxis of a disease or condition in which plasma kallikrein activity is implicated comprising administering to a patient in need of such treatment and/or prophylaxis a therapeutically effective amount of at least one of the compounds of the present invention or a stereoisomer, a tautomer, a pharmaceutically acceptable salt, or a solvate thereof.

The disease or condition in which plasma kallikrein activity is implicated includes, but not limited to, impaired visual acuity, diabetic retinopathy, diabetic macular edema, hereditary angioedema, diabetes, pancreatitis, nephropathy, cardio myopathy, neuropathy, inflammatory bowel disease, arthritis, inflammation, septic shock, hypotension, cancer, adult respiratory distress syndrome, disseminated intravascular coagulation, and cardiopulmonary bypass surgery.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans-(or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond. "Alkyl" also includes deuteroalkyl such as $CD_3$.

"Alkenyl" or "alkenylene" is intended to include hydrocarbon chains of either straight or branched configuration having one or more, preferably one to three, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups; such as ethenyl, propenyl, butenyl, pentenyl, and hexenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Alkoxy also includes deuteroalkoxy such as $OCD_3$. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "amino", as used herein, refers to —$NH_2$.

The term "substituted amino", as used herein, refers to the defined terms below having the suffix "amino" such as "arylamino", "alkylamino", "arylamino", etc.

The term "alkoxycarbonyl", as used herein, refers to an alkoxy group attached to the parent molecular moiety through a carbonyl group.

The term "alkoxycarbonylamino", as used herein, refers to an —NHR wherein R is an alkoxycarbonyl group.

The term "alkylamino", as used herein refers to —NHR, wherein R is an alkyl group.

The term "alkylcarbonyl", as used herein, refers to an alkyl group attached to the parent molecular moiety through a carbonyl group.

The term "alkylcarbonylamino", as used herein, refers to —NHR wherein R is an alkylcarbonyl group.

The term "aminosulfonyl", as used herein, refers to —SO$_2$NH$_2$.

The term "arylalkyl", as used herein, refers to an alkyl group substituted with one, two, or three aryl groups.

The term "arylamino", as used herein, refers to —NHR wherein R is an aryl group.

The term "arylcarbonyl", as used herein, refers to an aryl group attached to the parent molecular moiety through a carbonyl group.

The term "arylcarbonylamino", as used herein refers to —NHR wherein R is an arylcarbonyl group.

The term "cyano", as used herein, refers to —CN.

The term "cycloalkylamino", as used herein, refers to —NHR wherein R is a cycloalkyl group.

The term "cycloalkylcarbonyl", as used herein, refers to a cycloalkyl group attached to the parent molecular moiety through a carbonyl group.

The term "cycloalkylcarbonylamino", as used herein, refers to —NHR wherein R is a cycloalkylcarbonyl group.

The term "cycloalkyloxy", as used herein, refers to a cycloalkyl group attached to the parent molecular moiety through an oxygen atom.

The term "dialkylamino", as used herein, refers to NR$_2$, wherein each R is an alkyl group. The two alkyl groups are the same or different.

The term "haloalkoxy", as used herein, refers to a haloalkyl group attached to the parent molecular moiety through an oxygen atom.

The term "haloalkyl", as used herein, refers to an alkyl group substituted by one, two, three, or four halogen atoms.

The term "haloalkylamino", as used herein, refers to —NHR wherein R is a haloalkyl group.

The term "carbonyl" refers to C(=O) or C(O).

The term "carboxyl" or "carboxyl" refers to C(=O)OH.

The terms "carboxyl ester" and "oxycarbonyl" refer to the groups —C(O)O-alkyl, —C(O)O-substituted alkyl, —C(O)O-alkenyl, —C(O)O-substituted alkenyl, —C(O)O-alkynyl, C(O)O-substituted alkynyl, —C(O)O-cycloalkyl, —C(O)O-substituted cycloalkyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic.

The term "aminoacyl" or "amide", or the prefix "carbamoyl", "carboxamide", "substituted carbamoyl" or "substituted carboxamide" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic.

The term "haloalkylcarbonyl", as used herein, refers to a haloalkyl group attached to the parent molecular moiety through a carbonyl group.

The term "haloalkylcarbonylamino", as used herein, refers to —NHR wherein R is a haloalkylcarbonyl group.

The terms "alkylcarbonyl" refer to an alkyl or substituted alkyl bonded to a carbonyl.

The term "alkoxycarbonyl", as used herein, refers to an alkoxy group attached to the parent molecular moiety through a carbonyl group.

The term "hydroxy" or "hydroxyl" refers to OH.

As used herein the term "thiol" means —SH. A thiol may be substituted with a substituent disclosed herein, in particular alkyl(thioalkyl), aryl(thioaryl), or alkoxy(thioalkoxy).

As used herein the term "sulfonyl", used alone or linked to other terms such as alkylsulfonyl or arylsulfonyl, refers to the divalent radicals —SO$_2$—. In aspects of the invention a sulfonyl group, the sulfonyl group may be attached to a substituted or unsubstituted hydroxyl, alkyl group, ether group, alkenyl group, alkynyl group, aryl group, cycloalkyl group, cycloalkenyl group, cycloalkynyl group, heterocyclic group, carbohydrate, peptide, or peptide derivative.

The term "cycloalkyl" refers to cyclized alkyl groups, including mono-, bi- or poly-cyclic ring systems. "C$_3$ to C$_7$ cycloalkyl" or "C$_{3-7}$ cycloalkyl" is intended to include C$_3$, C$_4$, C$_5$, C$_6$, and C$_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocyclyls include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocyclyl (e.g., [2.2.2]bicyclooctane). Preferred carbocyclyls, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997).

"$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle", "heterocyclyl" or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocyclyl may optionally be quaternized. It is preferred that when the total number of S and O atoms in the heterocyclyl exceeds 1, then these heteroatoms are not adjacent to one another. It is preferred that the total number of S and O atoms in the heterocyclyl is not more than 1. When the term "heterocyclyl" is used, it is intended to include heteroaryl.

Examples of heterocyclyls include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocyclyls.

Examples of 5- to 10-membered heterocyclyls include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocyclyls include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocyclyls.

As used herein, the term "bicyclic heterocyclyl" "bicyclic heterocyclyl" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocyclyl, a 6-membered heterocyclyl or a carbocyclyl (provided the first ring is not benzo when the second ring is a carbocyclyl).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocyclyl exceeds 1, then these heteroatoms are not adjacent to one another. It is preferred that the total number of S and O atoms in the heterocyclyl is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydroquinolinyl, 2,3-dihydrobenzofuranyl, chromanyl, 1,2,3,4-tetrahydroquinoxalinyl, and 1,2,3,4-tetrahydroquinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocyclyl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5: "Design and Application of Prodrugs", *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or hours, "rt" for room temperature, "RT" for retention time, "RBF" for round bottom flask, "atm" for atmosphere, "psi" for pounds per square inch, "conc." for concentrate, "RCM" for ring-closing metathesis, "sat" or "sat'd" for saturated, "SFC" for supercritical fluid chromatography "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
Boc$_2$O di-tert-butyl dicarbonate
AcOH or HOAc acetic acid
BOP reagent benzotriazol-1-yloxytris(dimethylamino)phosphonium hexafluorophosphate
Burgess reagent 1-methoxy-N-triethylammoniosulfonyl-methanimidate
Cbz carbobenzyloxy
DCM or CH$_2$Cl$_2$ dichloromethane
CH$_3$CN or ACN acetonitrile
CDCl$_3$ deutero-chloroform
CHCl$_3$ chloroform
mCPBA or m-CPBA meta-chloroperbenzoic acid
Cs$_2$CO$_3$ cesium carbonate
Cu(OAc)$_2$ copper (II) acetate
CuI copper(I) iodide
CuSO$_4$ copper(II) sulfate
Cy$_2$NMe N-cyclohexyl-N-methylcyclohexanamine
DBU 1,8-diazabicyclo[5.4.0]undec-7-ene
DCE 1,2 dichloroethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
EDC N-(3-dimethylaminopropyl)-N'-ethylcarbodiimide
EDCI N-(3-dimethylaminopropyl)-N'-ethylcarbodiimide hydrochloride
EDTA ethylenediaminetetraacetic acid
Et$_3$N or TEA triethylamine
EtOAc ethyl acetate
Et$_2$O diethyl ether
EtOH ethanol
GMF glass microfiber filter Grubbs II (1,3-bis(2,4,6-trimethylphenyl)-2-imidazolidi-nylidene)dichloro (phenylmethylene)(triycyclohexyl-phosphine)ruthenium
HCl hydrochloric acid
HATU O-(7-azabenzotriazol-1-yl)-N,N,N',N'-tetramethyl-uronium hexafluorophosphate
HEPES 4-(2-hydroxyethyl)piperaxine-1-ethanesulfonic acid
Hex hexane
HOBt or HOBT 1-hydroxybenzotriazole
$H_2O_2$ hydrogen peroxide
$H_2SO_4$ sulfuric acid
IBX 2-iodoxybenzoic acid
$InCl_3$ Indium(III) chloride
Jones reagent $CrO_3$ in aqueous $H_2SO_4$, 2 M
$K_2CO_3$ potassium carbonate
$K_2HPO_4$ potassium phosphate dibasic
$K_3PO_4$ potassium phosphate tribasic
KOAc potassium acetate
KOH potassium hydroxide
$K_3PO_4$ potassium phosphate
LAH lithium aluminum hydride
LG leaving group
LiOH lithium hydroxide
MeOH methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
NaOMe sodium methoxide
$Na_2SO_3$ sodium sulfite
$Na_2SO_4$ sodium sulfate
$NH_3$ ammonia
$NH_4Cl$ ammonium chloride
$NH_4OH$ ammonium hydroxide
$NH_4COOH$ ammonium formate
NMM N-methylmorpholine
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$[1,1'-bis(diphenylphosphino)-ferrocene]dichlo-ropalladium(II)
$Ph_3PCl_2$ triphenylphosphine dichloride
PG protecting group
$POCl_3$ phosphorus oxychloride
$PtO_2$ platinum oxide
i-PrOH or IPA isopropanol
PS Polystyrene
rt room temperature
TBAI tetra-n-butylammonium iodide
TFA trifluoroacetic acid
THF tetrahydrofuran
$TMSCHN_2$ trimethylsilyldiazomethane
$TMSN_3$ trimethylsilylazide
®T3P propane phosphonic acid anhydride
TRIS tris (hydroxymethyl) aminomethane
pTsOH p-toluenesulfonic acid The compounds of the present invention can be prepared in a number of ways known to one skilled in the art of organic synthesis, which are described in more detail in Section VI.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, atrial fibrillation, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (Colman, R. W. et al., eds., *Hemostasis and Thrombosis, Basic Principles and Clinical Practice*, Fifth Edition, p. 853, Lippincott Williams & Wilkins (2006)).

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood,* 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood,* 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", *Hemostasis and Thrombosis,* pp. 103-122, Lippincott Williams & Wilkins (2001); Schmaier, A. H., "Contact Activation", *Thrombosis and Hemorrhage,* pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Med.,* 202:271-281 (2005); Kleinschmitz et al., *J. Exp. Med.,* 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.,* 10:198-204 (2000)).

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.,* 101:329-354 (2001).) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.,* 87:774-777 (2002); Wang et al., *J. Thromb. Haemost.,* 3:695-702 (2005)). Also, factor XI deficiency rescues the perinatal lethal phenotype of complete protein C deficiency (Chan et al., *Amer. J. Pathology,* 158:469-479 (2001)). Furthermore, baboon cross-reactive, function blocking antibodies to human factor XI protect against baboon arterial—venous shunt thrombosis (Gruber et al., *Blood,* 102:953-955 (2003)). Evidence for an antithrombotic effect of small molecule inhibitors of factor XIa is also disclosed in published U.S. Patent Publication No. 2004/0180855 A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or post-traumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience,* 6:201-207 (2001); Gailani, D. et al., *Blood Coagulation and Fibrinolysis,* 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.,* 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.,* 15:1107-1113 (1995)). In another study, Factor XI levels above the 90th percentile in patients were associated with a 2.2-fold increased risk for venous thrombosis (Meijers, J. C. M. et al., *N. Engl. J. Med.*, 342:696-701 (2000)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, Second Edition, pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial and venous thrombosis, at doses that preserved hemostasis. (Wong P. C. et al., *Journal of Thrombosis and Thrombolysis*, 32(2): 129-137 (August 2011); Schumacher, W. et al., *Journal of Thrombosis and Haemostasis*, 3(Suppl. 1):P1228 (2005); Schumacher, W. A. et al., *Eur. J. Pharmacol.*, 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo. Pre-clinical and clinical studies using FXI antisense (ASO) has been shown to be effective in various venous and arterial thrombosis models, comparable to warfarin or enoxaparin without increased bleeding (Bueller et al., DOI: 10.1056/NEJMoa1405760 (2014)).

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery*, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; Chromogenix or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; Chromogenix or BMPM-2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.00035 M.

Factor XIIa determinations were made in 0.05 M HEPES buffer at pH 7.4 containing 0.145 M NaCl, 0.05 M KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human plasma kallikrein (Enzyme Research Laboratories) at a final assay concentration of 200 pM and the synthetic substrate S-2302 (H-(D)-Pro-Phe-Arg-pNA; Chromogenix) at a concentration of 0.00008-0.0004 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix or AnaSpec) at a concentration of 0.0002-0.0004 M.

The Michaelis constant, $K_m$, for substrate hydrolysis by each protease, was determined at 25° C. or 37° C. in the absence of inhibitor. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(V_{max} * S)/(K_m + S);$$

$$(v_o - v_s)/v_s = I/(K_i*(1+S/K_m)) \text{ for a competitive inhibitor with one binding site; or}$$

$$v_s/v_o = A+((B-A)/(1+(IC_{50}/(I))^n)); \text{ and}$$

$$K_i = IC_{50}/(1+S/K_m) \text{ for a competitive inhibitor}$$

where:

$v_o$ is the velocity of the control in the absence of inhibitor;
$v_s$ is the velocity in the presence of inhibitor;
$V_{max}$ is the maximum reaction velocity;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme: inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 1.5 times or 2 times, respectively, relative to the clotting time in the absence of the inhibitor. The IC1.5× or IC2× is found by linear interpolation from relative clotting time versus inhibitor concentration plots using inhibitor concentrations that span the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Illinois). Similarly, clotting times can be determined from laboratory animal species or humans dosed with compounds of the invention.

Activated Partial Thromboplastin Time (aPTT) is determined using ACTIN® (Dade-Behring, Illinois) following the directions in the package insert. Plasma (0.05 mL) is warmed to 37° C. for 1 minute. ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Innovin, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

Chymotrypsin determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human chymotrypsin at a final concentration of 0.2-2 nM (Calbiochem) and the synthetic substrate S-2586 (Methoxy-Succinyl-Arg-Pro-Tyr-pNA; Chromogenix) at a concentration of 0.0005-0.005 M.

Trypsin determinations were made in 0.1 M sodium phosphate buffer at a pH of 7.5 containing 0.2 M sodium chloride and 0.5% PEG 8000. Determinations were made using purified human trypsin (Sigma) at a final assay concentration of 0.1-1 nM and the synthetic substrate S-2222 (Bz-Ile-Glu (gamma-OMe, 50%)-Gly-Arg-pNA; Chromogenix) at a concentration of 0.0005-0.005 M.

The exemplified Examples disclosed below were tested in the Factor XIa assay described above and found having Factor XIa inhibitory activity. A range of Factor XIa inhibitory activity (Ki values) of ≤10 µM (10000 nM) was observed.

The exemplified Examples disclosed below were tested in the Plasma Kallikrein assay described above, with some Examples having both Factor XIa and Plasma Kallikrein inhibitory activity. For those Examples where the Plasma Kallikrein inhibitory activity was observed as Ki values of ≤10 µM (10000 nM), the inhibitory activity is reported.

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arteriovenous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arteriovenous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient. In one embodiment, the pharmaceutical composition is a solid formulation, e.g., a spray-dried composition, which may be used as is, or whereto the physician or the patient adds solvents, and/or diluents prior to use.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Solid dispersions are also called solid-state dispersions. In some embodiments, any compound described herein is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 300 milligrams per dosage unit, and the second anti-coagulant in an amount of about 1 to about 500 milligrams per dosage unit.

Where the compounds of the present invention are administered in combination with an anti-platelet agent, by way of general guidance, typically a daily dosage may be about 0.01 to about 300 milligrams of the compound of the present invention and about 50 to about 150 milligrams of the anti-platelet agent, preferably about 0.1 to about 4 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 100 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (aliskiren) and vasopepsidase inhibitors, an antiarrythmic agent selected from $I_{Kur}$ inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known nonsteroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPAR-gamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention can also be combined with soluble guanylate cyclase inhibitors, Chymase inhibitors, ROMK inhibitors, ACE inhibitors, ATII inhibitors, ATR inhibitors, NEP inhibitors and other compounds to treat heart failure.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Fourth Edition, Wiley-Interscience (2006)).

Macrocyclic compounds of this invention can be prepared by the condensation of an aminosubstituted aromatic compound with commercially available Boc and or Cbz protected allylamino acid to afford intermediate 1a as shown in scheme 1. Reduction of the nitro group followed by the condensation with an appropriate olefinic acid would afford the intermediate 1c which can be subjected to the Grubbs methathesis cyclization using Grubbs ruthenium catalysts in an appropriate solvent e.g DCM or EtOAc to afford macrocycle 1d. Reduction of the olefinic group in intermediate 1d would afford intermediate 1e. Removal of the protecting group under standard conditions known to those in the art of organic synthesis would arrive at the macrocycle intermediate 1f.

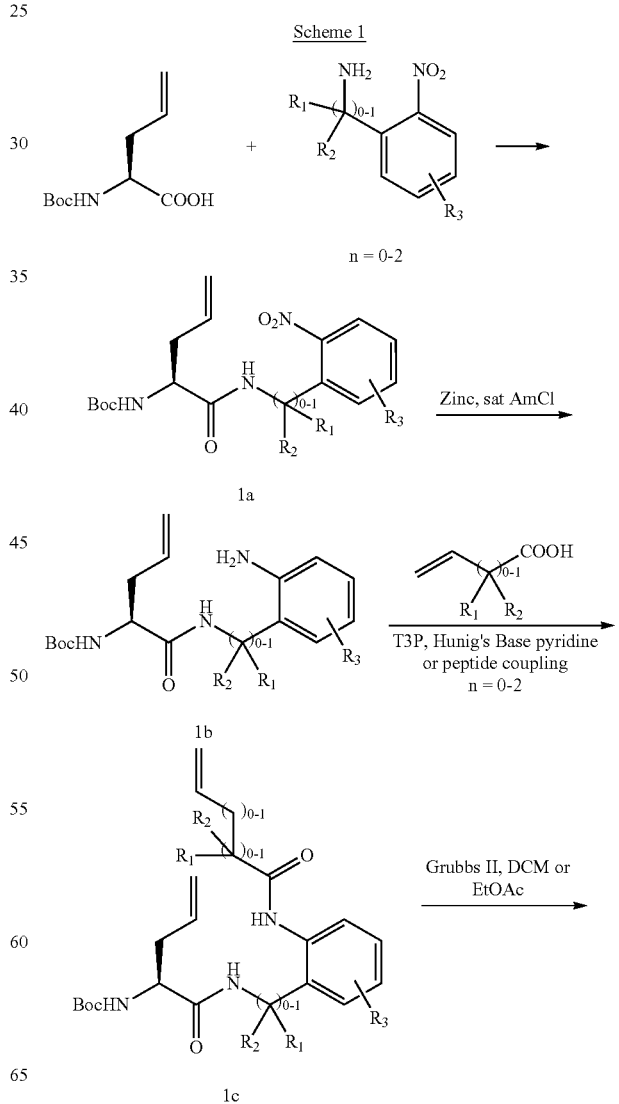

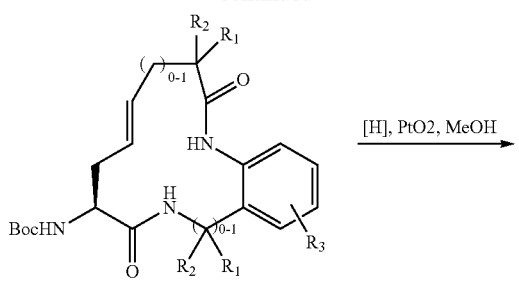

1d

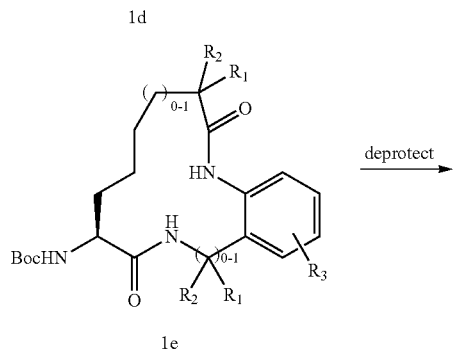

1e

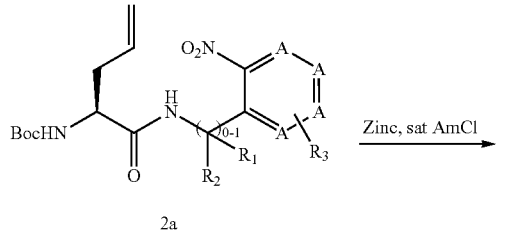

2a

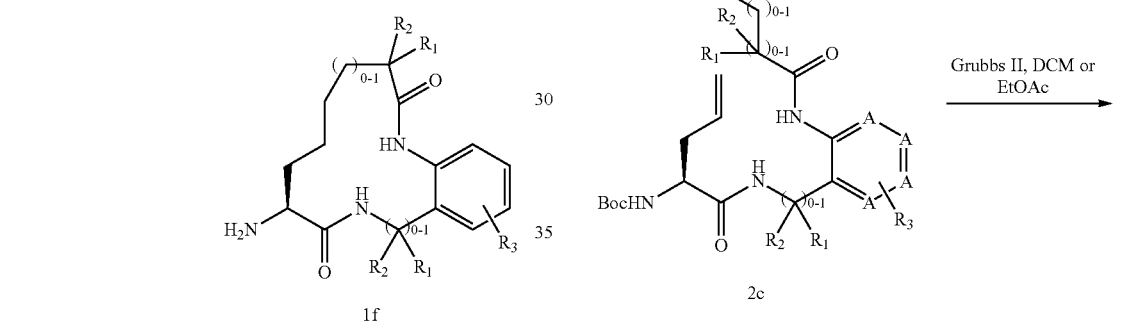

Alternatively intermediate 1d can also be deprotected to the amine and carried on to compounds of this invention. In situations wherein the coupling olefinic carboxylic acid is substituted the Grubbs cyclized product would result in the formation of diasteromers which can be separated by chiral HPLC methods known in the art. The resultant diateromers can then be carried onwards to various diasteromeric forms of intermediate 1f.

In a similar manner various 6-membered heterocyclic macrocycles of this invention such as pyridyls, pyridazines, pyrimidines and pyrazines can be prepared as shown in scheme 2.

Scheme 2

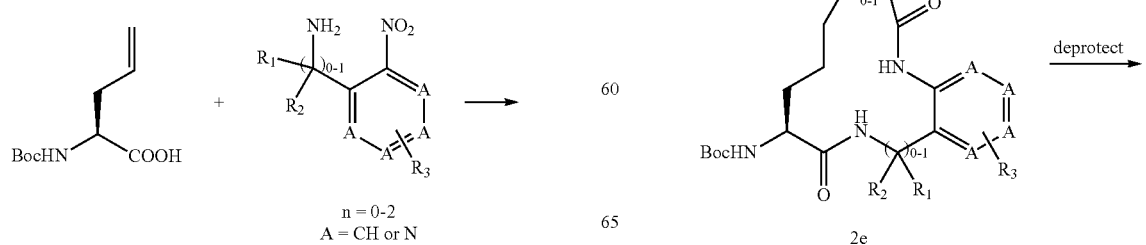

n = 0-2
A = CH or N

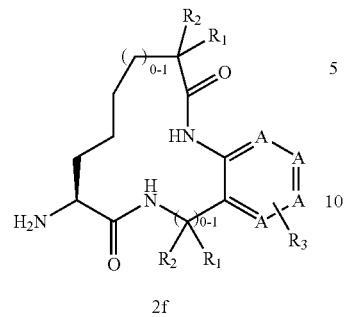

2f

In a similar manner various 5-membered heterocyclic containing macrocycles of this invention can be prepared as shown in scheme 3. The 5-membered heterocycles such as substituted thiophenes, pyrazoles, imidazoles, oxazoles, thiazoles, isoxazole, isothiazoles, 1,2,3-triazoles and other combinations there off when appropriately substituted can be employed to prepared a diverse array of 5-membered heterocyclic containing macrocycles of this invention. Also included in this invention are regioisomeric 5-membered heterocycles which can be prepared early on in the synthesis and then coupled to the Boc-allylamino acid. In situations wherein the regioisomer is difficult to separate these are coupled to the Boc-allylaminoacid and the coupled intermediate 1 is then separated by chiral HPLC and these intermediates are then carried on separately to afford compounds of this invention. The substitutions on the heterocycles can be diverse which also includes deuterium and halogen groups.

Scheme 3

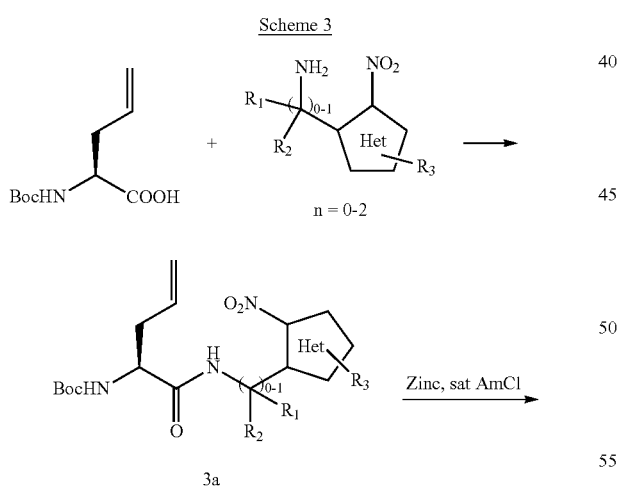

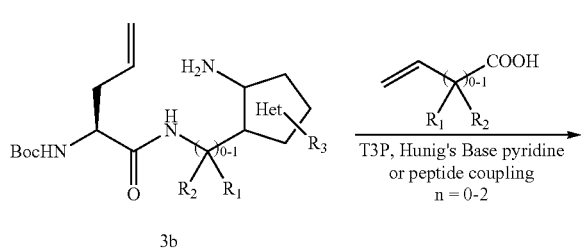

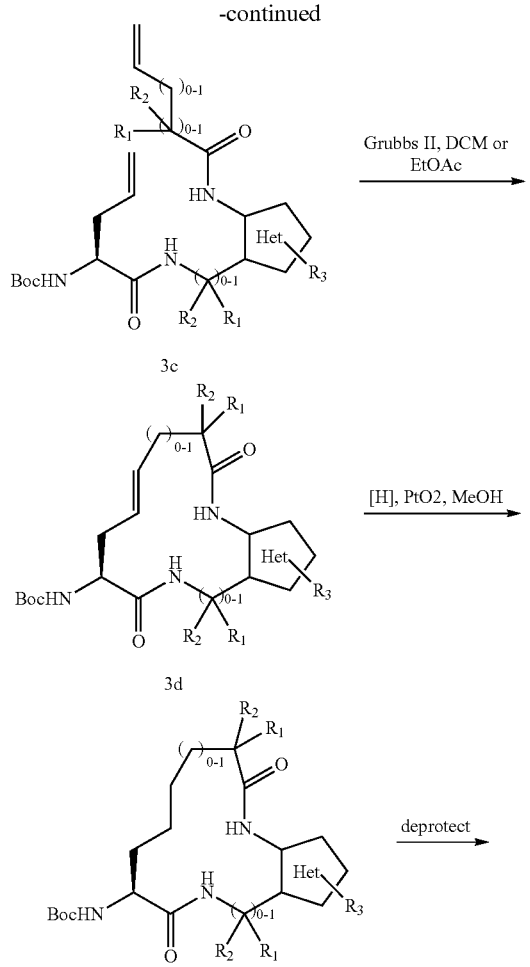

Het = 5 membered heterocycles e.g thiophene, oxazole, thazole isothiazole, isoxazoles, pyrazoles, pyrazolines, isoxazolines, thiadiazoles oxadiazoles In instances wherein the nitro functional group is not accessible in a heterocycle a halogen on as substituted 5 and or 6-membered heterocycle can be employed. The halogen can be aminated using Palladium catalyzed conditions using diphenylimine as used by Buchwald and co-workers. Alternatively the halogen can be directly aminated using a wide variety of Ullman like conditions using an amine source or sodium azide. These in turn can be utilized to prepare macrocycles of this invention.

Scheme 4 describes the synthesis of suitably substituted pyrimidin-4-ol derivatives where G1 is a substituted phenyl. Aniline 4a can be converted to a suitably substituted triazole 4b in a one pot, two step sequence. Specifically, the aniline 4a is converted to the aryl azide in situ followed by cycloaddition with a suitably substituted alkyne in the presence of a copper catalyst, such as Cu₂O, to provide 4b. Demethylation of 4b provides the pyrimidin-4-ol derivatives 4c. The trimethylsilyl group, can be converted to a chloride at elevated temperature with NCS in the presence of silica gel. Aniline 4a can be converted to the iodide 4d with p-TsOH, NaNO₂, and NaI. Subjecting iodide 4d to a variety of N-arylation or Suzuki-Miyaura couplings, followed by demethylation, gives additional pyrimidin-4-ol derivatives 4e. The tetrazole intermediate 4g can be prepared by first treatment of the aniline 4a with trimethoxymethane and sodium azide followed by demethylation of the methoxy group.

Scheme 5 describes the synthesis of suitably substituted pyrimidin-4-ol derivatives wherein a thiadiazole is incorporated. Bromide 5a can be converted to acetyl compound 5b by coupling with 1-(trimethylsilyl)ethanone with Pd catalyst. 5b can react with ethyl hydrazinecarboxylate to form 5c, which upon treatment with SOCl₂ to give thiadiazole compound 5d. Intermediate 5e can be obtained by demethylation of 5d. Alternatively 5a can be subjected to cross couplings conditions known in the art to prepared various other 5 and or 6-membered substituted para chlorophenyl intermediates such as 5f. 5f can be then demethylated to afford requisite intermediates such as 5g.

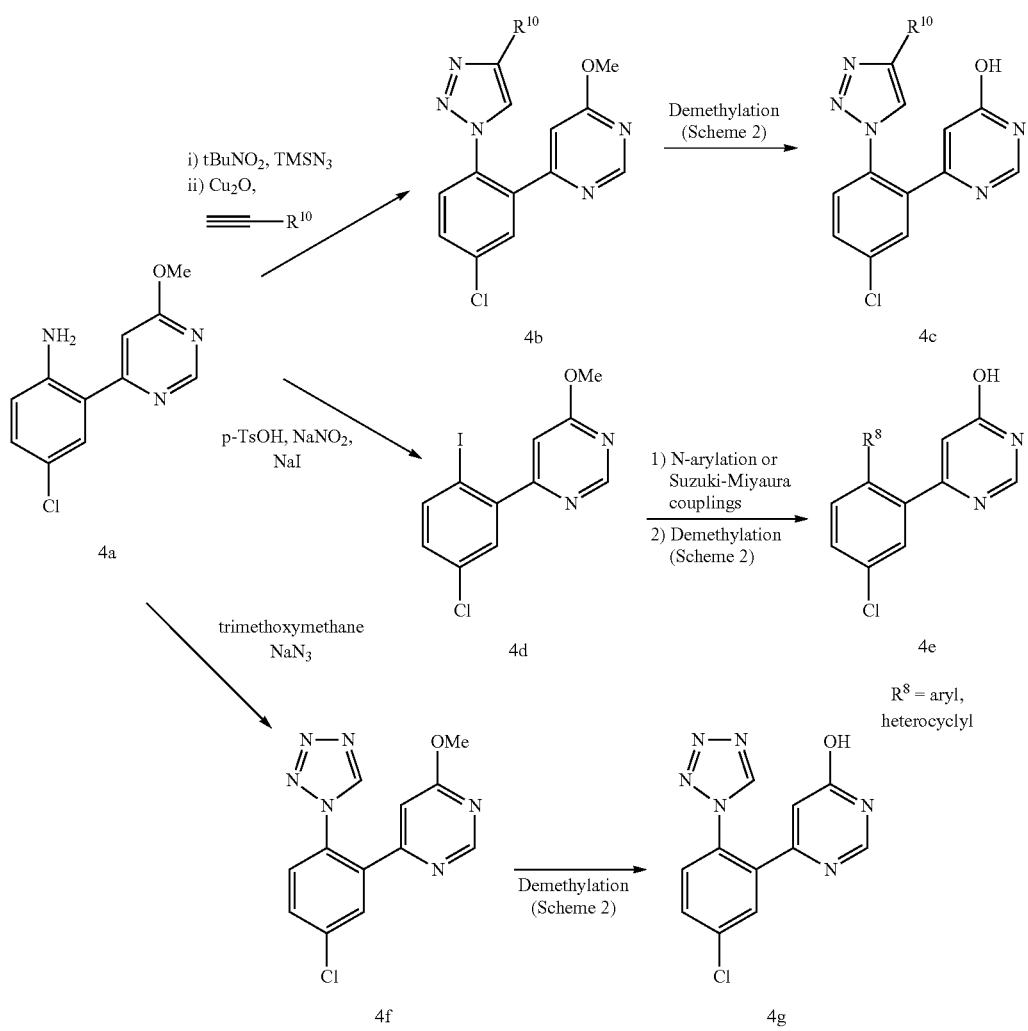

Scheme 4

Scheme 5

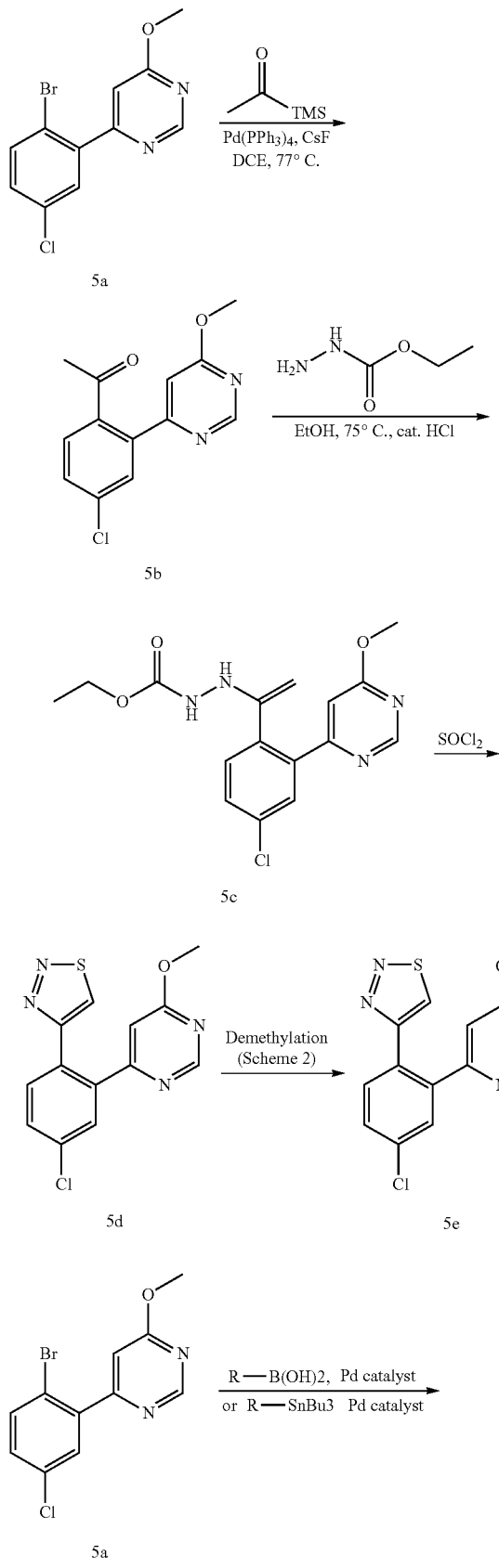

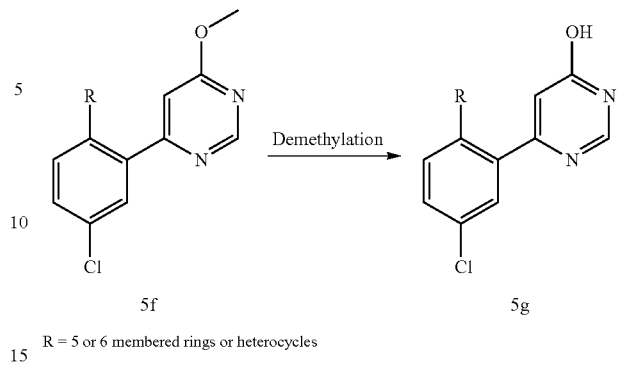

R = 5 or 6 membered rings or heterocycles

Representative pyrimidinone compounds 1a of this invention can be prepared as described in Scheme 6. Using a modified procedure described by Xiao (*Organic Letters*, 11:1421 (2009)), suitably substituted pyrimidin-4-ol derivatives 6b can be coupled with an appropriately substituted macrocycle amine (scheme 1-3) in the presence of HATU and DBU in a solvent such as $CH_3CN$ to provide pyrimidinone compounds 1a.

Scheme 6

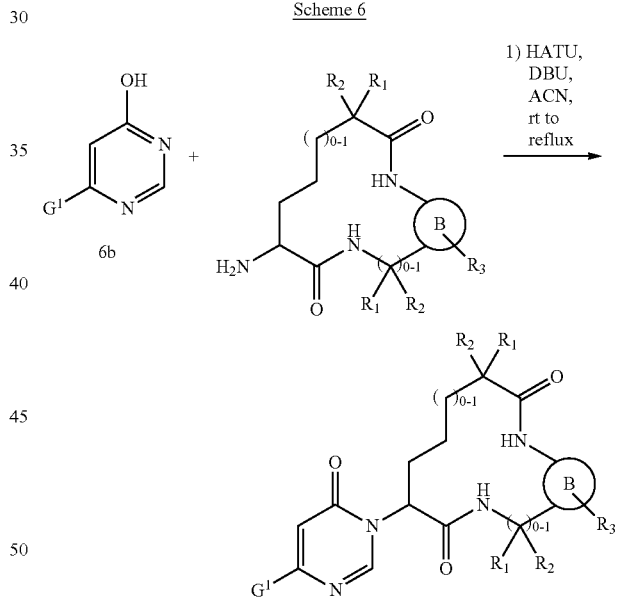

Scheme 7 describes the synthesis of suitably substituted pyrimidin-4-ol derivatives 7d. Suzuki-Miyaura coupling between 6-chloropyrimidin-4-ol (7a or 7b) and an appropriately substituted heteroaryl boronic acid or ester in the presence of a base such as Hunig's base or potassium phosphate tribasic, in a solvent mixture, such as toluene and ethanol, or THF, using a precatalyst such as $Pd(PPh_3)_4$ or $2^{nd}$ generation Xphos provides 7d. Alternatively, when 4-chloro-6-methoxypyrimidine 7b is used, an additional deprotection step, employing aqueous HBr at elevated temperatures, is required to provide pyrimidin-4-ol derivatives 7d. Alternatively, 7c can be condensed with ammonium acetate to afford intermediate 7d.

Scheme 7

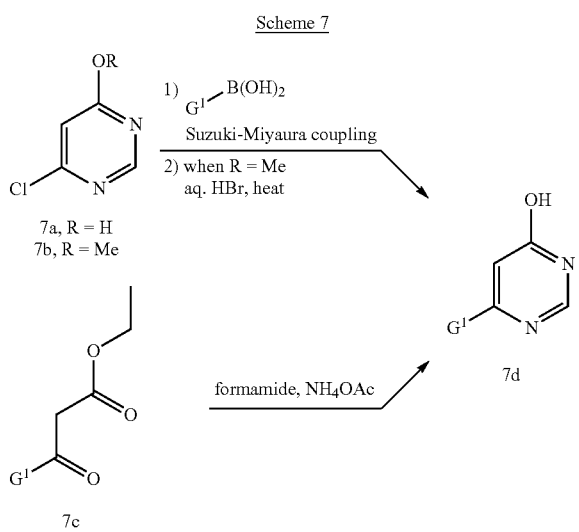

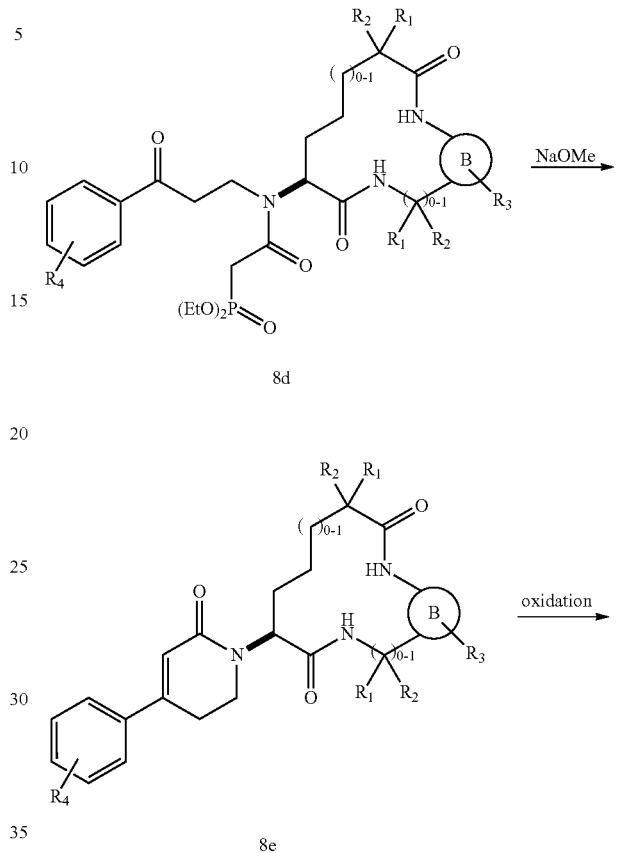

Dihydropyridones of this invention can be prepared by the method outlined in scheme 8. Starting from aldehyde 8a, vinyl Grignard addition (yielding allylic alcohol 8b) followed by oxidation gives vinyl ketones 8c. Michael addition of the amines from Scheme 1-3 followed by acylation with phosphonic acids affords compounds 2e, which upon cyclization with base provides the dihydropyridone 8e. Further oxidation of 8e Should afford pyridone analogs of this invention 8f.

Scheme 8

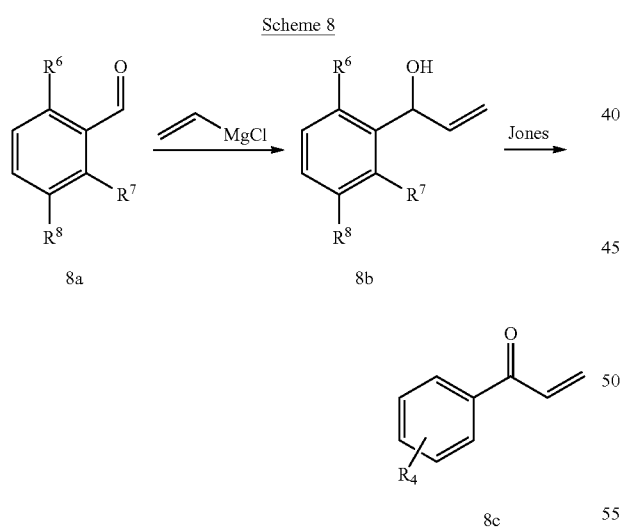

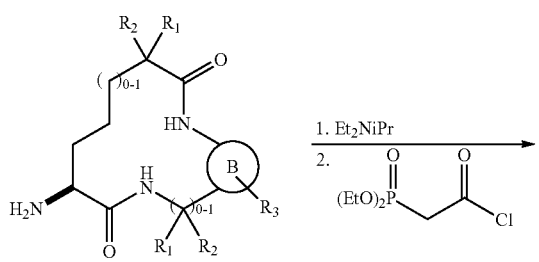

Alternatively macrocycles of this invention can be coupled to a requisite azole carboxylic acid to afford compounds 9a of this invention as shown in scheme 9. Likewise coupling of the requisite macrocyclic amine with acrylic acid or propionic acids of this invention should afford compounds 9b of this invention. Similarly coupling of the macrocyclic amines with Boc protected trans-examic acid should afforded compounds 9c of this invention after deprotection.

Scheme 9
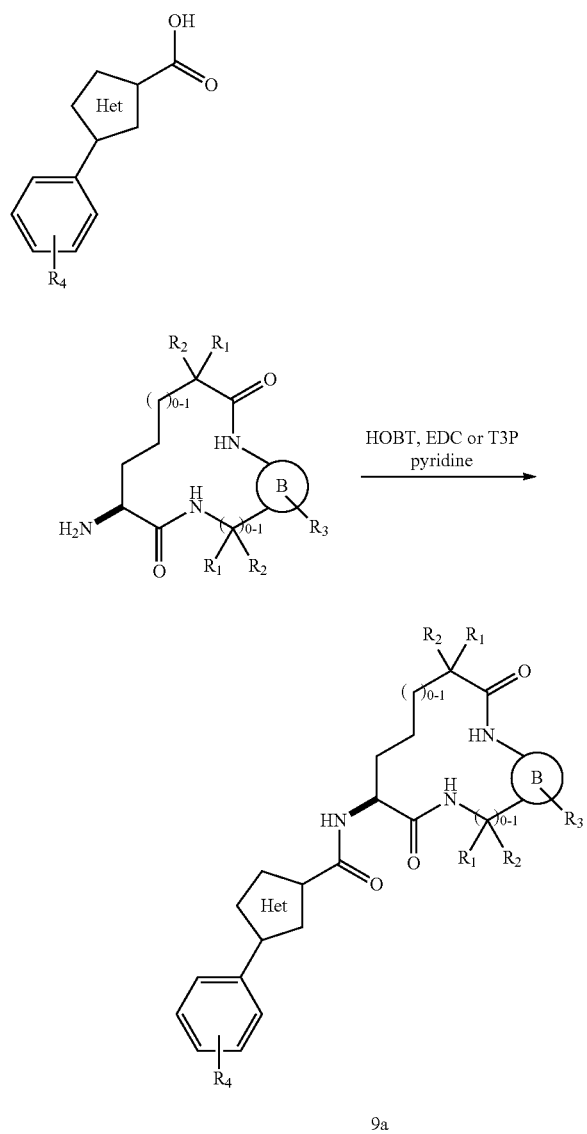
Het = pyrazole, triazole imidazole, isoxazole, isoxazolin, pyrazoline
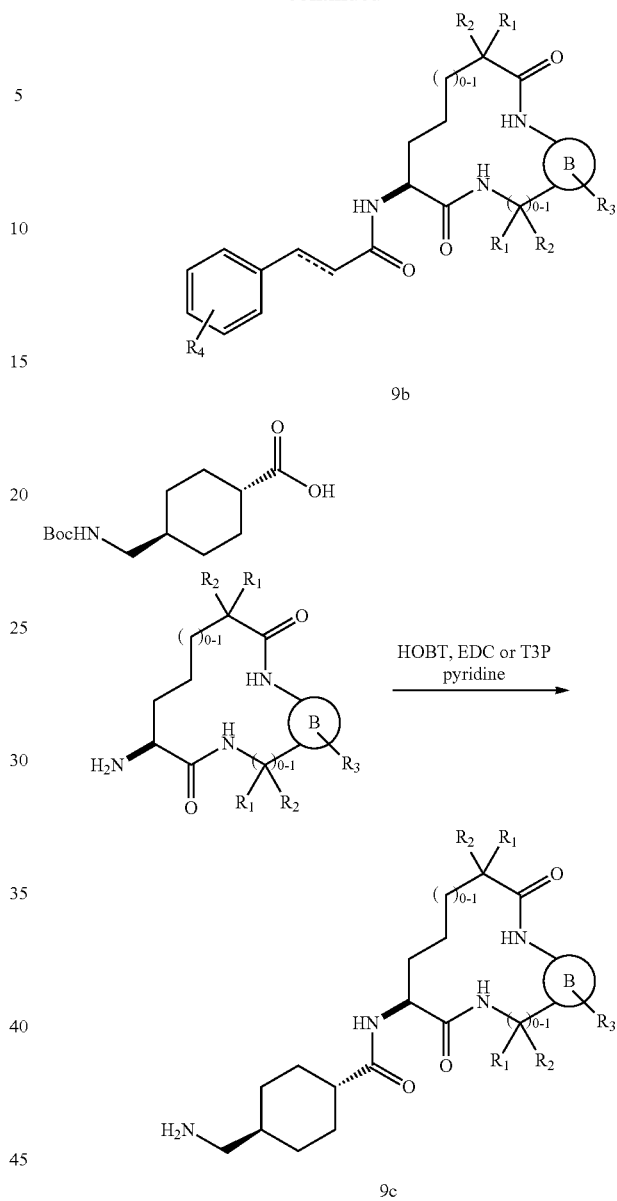
Additional compounds of this invention can be synthesized by cross coupling techniques known to those in the art to afford additional compounds of this invention as shown in scheme 10.
Scheme 10
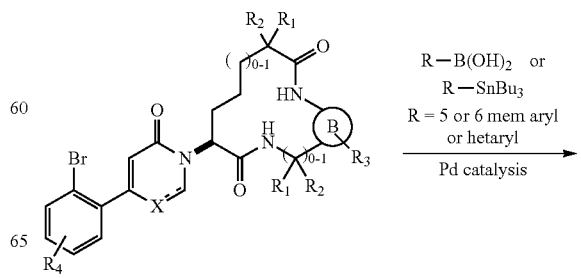

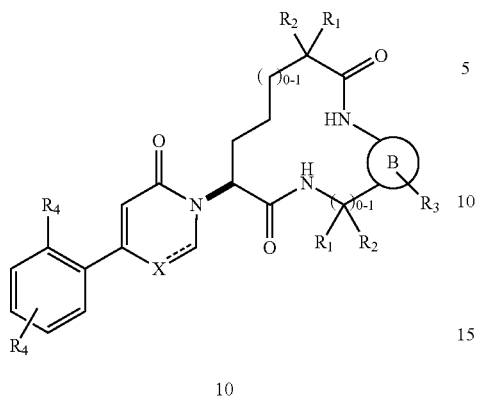

10

X = CH2 or CH or N

Purification of intermediates and final products was carried out via either normal or reverse phase chromatography. Normal phase chromatography was carried out using prepacked $SiO_2$ cartridges eluting with either gradients of hexanes and EtOAc, DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm) (or) Sunfire Prep C18 OBD 5u 30×100 mm, 25 min gradient from 0-100% B. A=$H_2O$/ACN/TFA 90:10:0.1. B=ACN/$H_2O$/TFA 90:10:0.1

Unless otherwise stated, analysis of final products was carried out by reverse phase analytical HPLC.

Method A: Waters SunFire column (3.5 Lm C18, 3.0×150 mm). Gradient elution (0.5 mL/min) from 10-100% Solvent B for 12 min and then 100% Solvent B for 3 min was used. Solvent A is (95% water, 5% acetonitrile, 0.05% TFA) and Solvent B is (5% water, 95% acetonitrile, 0.05% TFA, UV 254 nm).

Method B: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method C: Waters Acquity UPLC BEH C18, 2.1×50 mm, 1.7-μm particles; Mobile Phase A: 5:95 acetonitrile: water with 0.1% TFA; Mobile Phase B: 95:5 acetonitrile: water with 0.1% TFA; Temperature: 50° C.; Gradient: 0-100% B over 3 minutes, then a 0.75-minute hold at 100% B; Flow: 1.11 mL/min Method X: Zorbax SB C18 column (4.6×75 mm). Gradient elution (2.5 mL/min) from 0-100% Solvent B for 8 min and then 100% Solvent B for 2 min was used. Solvent A is (90% water, 10% MeOH, 0.02% $H_3PO_4$) and Solvent B is (10% water, 90% MeOH, 0.02% $H_3PO_4$, UV 220 nm).

Intermediate 1. Preparation of (R)-2-Methylbut-3-enoic acid

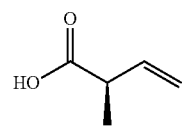

1A. Preparation of (R)-4-Benzyl-3-((R)-2-methyl-but-3-enoyl)oxazolidin-2-one

To the solution of 2-methylbut-3-enoic acid (5.59 g, 55.9 mmol) and NMM (6.14 ml, 55.9 mmol) in THF (62 ml) at 0° C. was added pivaloyl chloride (6.87 ml, 55.9 mmol) dropwise. The reaction mixture was cooled to −78° C., and stirred for ~2 h. In a separate flask: To a solution of (R)-4-benzyloxazolidin-2-one (8.25 g, 46.6 mmol) in THF (126 ml) at −78° C. was added 2.5 M n-BuLi in hexane (20.49 ml, 51.2 mmol) dropwise. After 35 min, this reaction was transferred via cannula to the first reaction. The reaction mixture was stirred at −78° C. for 2 h, then the cold bath was removed, and the reaction was quenched with sat $NH_4Cl$. The reaction was diluted with water and extracted with EtOAc (3×). The combined organic layers were washed with brine, dried over $Na_2SO_4$, filtered, and concentrated to give a yellow oil (15 g). Purification by silica gel chromatography afforded (R)-4-benzyl-3-((R)-2-methylbut-3-enoyl)oxazolidin-2-one (6.59 g, 55%) as a colorless oil. MS (ESI) m/z: 282.1 (M+Na)$^+$. $^1$H NMR (500 MHz, CDCl$_3$) δ 7.36-7.19 (m, 5H), 6.03-5.93 (m, 1H), 5.23-5.10 (m, 2H), 4.69-4.63 (m, 1H), 4.51-4.43 (m, 1H), 4.23-4.15 (m, 2H), 3.29 (dd, J=13.5, 3.3 Hz, 1H), 2.79 (dd, J=13.5, 9.6 Hz, 1H), 1.35 (d, J=6.9 Hz, 3H) ppm. The other diastereomer (R)-4-benzyl-3-((S)-2-methylbut-3-enoyl)oxazolidin-2-one (4.6 g, 38%) also obtained as a white solid. MS (ESI) m/z: 260.1 (M+H)$^+$.

1B. Preparation of (R)-2-Methylbut-3-enoic acid

To a clear colorless solution of (R)-4-benzyl-3-((R)-2-methylbut-3-enoyl)oxazolidin-2-one (6.05 g, 23.33 mmol) in THF (146 ml) at 0° C. was added dropwise $H_2O_2$ (9.53 ml, 93 mmol) (30% aqueous) followed by 2 N LiOH (23.33 mL, 46.7 mmol). After 30 min, the reaction was quenched with 25 ml of sat $Na_2SO_3$ and 25 ml of sat $NaHCO_3$. The reaction was then concentrated to remove the THF. The residue was diluted with water and extracted with CHCl$_3$ (3×). The aqueous layer was acidified with conc. HCl to pH-3 and then it was extracted with EtOAc (3×). The EtOAc layers were combined, washed with brine, dried over MgSO$_4$, filtered and concentrated to afford (R)-2-methylbut-3-enoic acid (2.15 g, 92%) as a colorless oil. $^1$H NMR (500 MHz, CDCl$_3$) δ 10.84 (br. s., 1H), 5.94 (ddd, J=17.4, 10.1, 7.4 Hz, 1H), 5.22-5.13 (m, 2H), 3.23-3.15 (m, 1H), 1.31 (d, J=7.2 Hz, 3H) ppm.

Intermediate 2. Preparation of 6-[5-Chloro-2-(4-chloro-1H-1,2,3-triazol-1-yl)phenyl]pyrimidin-4-ol

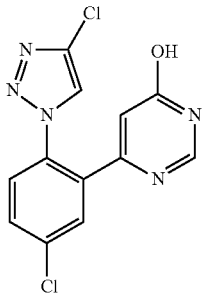

2A. Preparation of 4-Chloro-2-(tetramethyl-1,3,2-dioxaborolan-2-yl)aniline

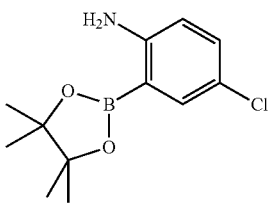 [SMILES: CC1(C)OB(c2cc(Cl)ccc2N)OC1(C)C]

In a 20 ml microwave vial was added 2-bromo-4-chloroaniline (3 g, 14.53 mmol), 4,4,5,5-tetramethyl-2-(tetramethyl-1,3,2-dioxaborolan-2-yl)-1,3,2-dioxaborolane (5.53 g, 21.80 mmol), KOAc (3.66 g, 37.3 mmol), Pd(dppf)Cl$_2$—CH$_2$Cl$_2$ adduct (0.32 g, 0.44 mmol) and DMSO (9 ml). The resulting suspension was purged with N$_2$, capped and heated at 80° C. for 22 h. The reaction was cooled to rt. Water was added to dissolve the salts, then the reaction was filtered. The remaining solid was suspended in DCM and the insoluble solid was filtered. The filtrate was concentrated and then purified by normal phase chromatography to give 4-chloro-2-(tetramethyl-1,3,2-dioxaborolan-2-yl)aniline (3.15 g, 86% yield) as a white solid. MS (ESI) m/z: 172.3 (M-C$_6$H$_{10}$+H)$^+$. $^1$H NMR (400 MHz, CDCl$_3$) δ 7.54 (d, J=2.6 Hz, 1H), 7.13 (dd, J=8.8, 2.6 Hz, 1H), 6.52 (d, J=8.6 Hz, 1H), 4.72 (br. s., 2H), 1.34 (s, 12H).

2B. Preparation of 4-Chloro-2-(6-methoxypyrimidin-4-yl)aniline

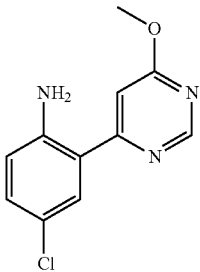 [SMILES: COc1cc(-c2cc(Cl)ccc2N)ncn1]

A RBF containing 4-chloro-6-methoxy pyrimidine (3.13 g, 21.62 mmol), 4-chloro-2-(tetramethyl-1,3,2-dioxaborolan-2-yl) aniline (7.31 g, 21.62 mmol), Na$_2$CO$_3$ (2.29 g, 21.62 mmol), DME (86 ml), EtOH (10.81 ml) and water (10.81 ml) was equipped with a condenser. The mixture was purged with Ar for several min then Pd(dppf)Cl$_2$.CH$_2$Cl$_2$ adduct (1.77 g, 2.16 mmol) was added. The reaction was heated at 90° C. for 5 h. The reaction was cooled to rt, diluted with water and extracted with EtOAc. The organic layer was washed with brine, concentrated and purified by normal phase chromatography to give 4-chloro-2-(6-methoxypyrimidin-4-yl)aniline (2.86 g, 56.1% yield) as yellow solid. MS (ESI) m/z: 236.0 (M+H)$^+$. $^1$H NMR (500 MHz, CDCl$_3$) δ 8.78 (d, J=1.1 Hz, 1H), 7.49 (d, J=2.5 Hz, 1H), 7.15 (dd, J=8.8, 2.5 Hz, 1H), 6.99 (d, J=1.1 Hz, 1H), 6.67 (d, J=8.8 Hz, 1H), 5.89 (br. s., 2H), 4.03 (s, 3H).

2C. Preparation of 4-{5-Chloro-2-[4-(trimethylsilyl)-1H-1,2,3-triazol-1-yl]-phenyl}-6-methoxy-pyrimidine

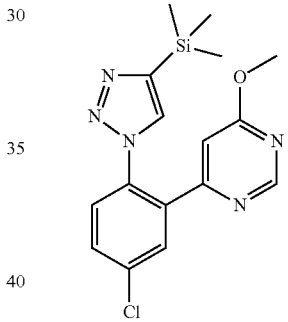

To a solution of 4-chloro-2-(6-methoxypyrimidin-4-yl) aniline (1.5 g, 6.36 mmol) in ACN (90 ml) at 0° C. was added 3-methylbutyl nitrite (1.28 ml, 9.55 mmol), followed by the dropwise addition of TMSN$_3$ (1.26 ml, 9.55 mmol). Gas evolution was observed. After 10 min, the ice bath was removed, and the reaction was allowed to warm to rt. After 1 h, ethynyltrimethylsilane (2.72 ml, 19.09 mmol) and Cu$_2$O (0.09 g, 0.64 mmol) were added and the reaction was stirred for an additional 1 h. The reaction was partitioned between EtOAc and sat NH$_4$Cl, and the layers were separated. The organic layer was washed with brine, dried over MgSO$_4$, filtered and concentrated. Purification by normal phase chromatography gave 4-{5-chloro-2-[4-(trimethylsilyl)-1H-1,2,3-triazol-1-yl]phenyl}-6-methoxypyrimidine (2.13 g, 5.92 mmol, 93% yield) as a yellow solid. MS(ESI) m/z: 360.3 (M+H)$^+$. $^1$H NMR (400 MHz, CDCl$_3$) δ 8.71 (d, J=1.1 Hz, 1H), 7.82 (d, J=2.2 Hz, 1H), 7.61-7.56 (m, 1H), 7.54-7.48 (m, 2H), 6.20 (d, J=1.1 Hz, 1H), 3.92 (s, 3H), 0.32-0.28 (m, 9H).

2D. Preparation of 4-[5-Chloro-2-(4-chloro-1H-1,2,3-triazol-1-yl)phenyl]-6-methoxypyrimidine

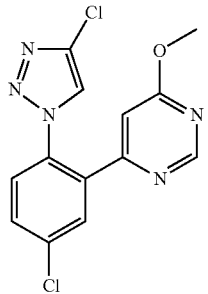

To a solution of 4-{5-chloro-2-[4-(trimethylsilyl)-1H-1,2,3-triazol-1-yl]phenyl})-6-methoxypyrimidine (1.56 g, 4.33 mmol) in ACN (28.9 ml) was added NCS (2.03 g, 15.17 mmol) and silica gel (6.51 g, 108 mmol). The reaction was stirred at 80° C. for 1 h. Then, the reaction was filtered to remove the silica gel and the collected silica gel was washed with EtOAc. The filtrate was washed with water (2×), brine and concentrated. Purification by normal phase chromatography gave 4-[5-chloro-2-(4-chloro-1H-1,2,3-triazol-1-yl)phenyl]-6-methoxypyrimidine (0.90 g, 64.5% yield) as a yellow foam. MS(ESI) m/z: 322.3 (M+H)$^+$. $^1$H NMR (400 MHz, CDCl$_3$) δ 8.70 (d, J=1.1 Hz, 1H), 7.75 (d, J=2.4 Hz, 1H), 7.66-7.55 (m, 2H), 7.50 (d, J=8.6 Hz, 1H), 6.52 (d, J=0.9 Hz, 1H), 3.98 (s, 3H).

2E. Preparation of 6-[5-Chloro-2-(4-chloro-1H-1,2,3-triazol-1-yl)phenyl] pyrimidin-4-ol

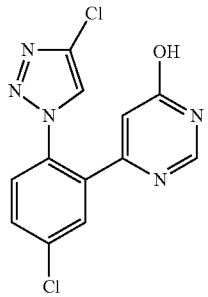 [SMILES: Oc1cc(-c2cc(Cl)ccc2-n2cc(Cl)nn2)ncn1]

To a solution of 4-[5-chloro-2-(4-chloro-1H-1,2,3-triazol-1-yl)phenyl]-6-methoxypyrimidine (900 mg, 2.79 mmol) in AcOH (6 ml) was added 48% HBr in water (3 ml, 26.5 mmol). The mixture was stirred at 85° C. for 1 h. The reaction was concentrated to dryness and then partitioned between EtOAc and sat NaHCO$_3$ solution. The mixture was separated and the aqueous layer was extracted with EtOAc (2×). The organic layers were combined, concentrated, and then the residue was purified by normal phase chromatography to give a white solid. The solid was suspended in Et$_2$O, filtered and washed with Et$_2$O to give 6-[5-chloro-2-(4-chloro-1H-1,2,3-triazol-1-yl)phenyl]pyrimidin-4-ol (610 mg, 70.9% yield) as a white solid. MS(ESI) m/z: 308.3 (M+H)$^+$. $^1$H NMR (400 MHz, CDCl$_3$) δ 7.96 (s, 1H), 7.74-7.67 (m, 2H), 7.62 (dd, J=8.5, 2.3 Hz, 1H), 7.47 (d, J=8.4 Hz, 1H), 6.44 (d, J=0.9 Hz, 1H).

Intermediate 3. Preparation of 6-(3-Chloro-6-(4-chloro-1H-1,2,3-triazol-1-yl)-2-fluorophenyl)-pyrimidin-4-ol

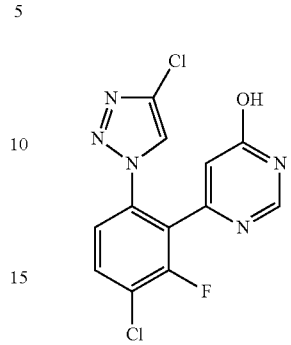

3A. Preparation of N-(4-Chloro-3-fluorophenyl)-2,2,2-trifluoroacetamide

To a suspension of 4-chloro-3-fluoroaniline (10.67 g, 73.3 mmol) and Na$_2$CO$_3$ (24.5 g, 125 mmol) in Et$_2$O (300 ml) at −10° C. under N$_2$ was added TFAA (12.23 ml, 88 mmol) dropwise. The mixture was allowed to warm to rt for 18 h. The reaction mixture was diluted with hexane (300 ml), and filtered. The filtrate was washed with ice-water, 10% aq NaHCO$_3$, and brine, dried over Na$_2$SO$_4$, and concentrated. A pale yellow solid obtained as N-(4-chloro-3-fluorophenyl)-2,2,2-trifluoroacetamide (17 g, 96% yield). MS (ESI) m/z: 242.1 (M+H)$^+$.

3B. Preparation of (6-Amino-3-chloro-2-fluorophenyl)boronic acid

To a cooled (−78° C.) clear, colorless solution of N-(4-chloro-3-fluorophenyl)-2,2,2-trifluoroacetamide (5 g, 20.70 mmol) in THF (69.0 ml) was added dropwise 2.5 M nBuLi in hexane (16.56 ml, 41.4 mmol) over 15 min, keeping the internal temperature below −60° C. The resulting clear, yellow solution was stirred at −78° C. for 10 min, then most of the dry ice chunks were removed. The reaction was allowed to warm to −50° C. over 1 h. The resulting clear brown solution was cooled to −78° C. and then triisopropyl borate (10.51 ml, 45.5 mmol) was added dropwise. The reaction was stirred at −78° C. for 10 min, and then the ice bath was removed and the reaction was allowed to warm to rt. The resulting orange suspension was stirred at rt for 2 h, then cooled in an ice bath and quenched with 1 N HCl (40 ml). The reaction mixture was warmed to 40° C. for 1 h and then cooled to rt. The reaction was diluted with EtOAc and the layers were separated. The organic layer was washed with brine and concentrated. Purification by normal phase chromatography afforded (6-amino-3-chloro-2-fluorophenyl)boronic acid (3 g, 76.6% yield). MS (ESI) m/z: 190.1 (M+H)$^+$.

3C. Preparation of 4-Chloro-3-fluoro-2-(6-methoxypyrimidin-4-yl)aniline

The reaction was run in a 350 ml pressure bottle. A solution of 4-chloro-6-methoxypyrimidine (1.784 g, 12.34 mmol), (6-amino-3-chloro-2-fluorophenyl)boronic acid (3.3 g, 12.34 mmol)) in toluene (24.68 ml) and EtOH (24.68 ml)) was purged with N$_2$ for several min. DIEA (4.31 ml, 24.68 mmol) followed by Pd(Ph₃P)₄ (1.426 g, 1.234 mmol) were added. The flask was capped and the reaction was heated (oil bath) at 120° C. for 2 h, then cooled to rt, and concentrated. Purification by normal phase chromatography afforded 4-chloro-3-fluoro-2-(6-methoxypyrimidin-4-yl)aniline (2 g, 45.2% yield) as a yellow solid. MS (ESI) m/z: 254.0 (M+H)⁺.

3D. Preparation of 4-(3-Chloro-2-fluoro-6-(4-(trimethylsilyl)-1H-1,2,3-triazol-1-yl)phenyl)-6-methoxypyrimidine

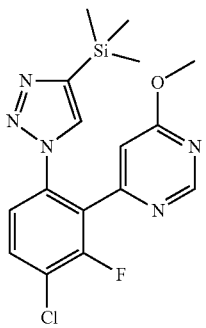 [SMILES: COc1cc(-c2c(-n3cc([Si](C)(C)C)nn3)ccc(Cl)c2F)ncn1]

To a cooled (0° C.), clear, yellow solution of 4-chloro-3-fluoro-2-(6-methoxypyrimidin-4-yl)aniline (2.1 g, 8.28 mmol) in ACN (118 ml) was added isoamyl nitrite (1.67 ml, 12.42 mmol), followed by the dropwise addition of TMSN₃ (1.63 ml, 12.42 mmol). After 10 min, the cold bath was removed, and the reaction was allowed to warm to rt. After 2 h, ethynyltrimethylsilane (3.54 ml, 24.84 mmol) and Cu₂O (0.118 g, 0.83 mmol) were added, and the reaction was stirred at rt for 1.5 h. The reaction was then diluted with EtOAc and washed with sat NH₄Cl, brine, dried over MgSO₄, filtered and concentrated to give a brown oil. Purification by normal phase chromatography afforded 4-(3-chloro-2-fluoro-6-(4-(trimethylsilyl)-1H-1,2,3-triazol-1-yl)phenyl)-6-methoxypyrimidine (2.71 g, 87% yield) as a brown solid. MS (ESI) m/z: 378.1 (M+H)⁺.

3E. Preparation of 4-(3-Chloro-6-(4-chloro-1H-1,2,3-triazol-1-yl)-2-fluorophenyl)-6-methoxypyrimidine

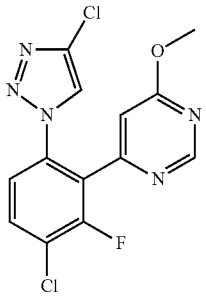 [SMILES: COc1cc(-c2c(-n3cc(Cl)nn3)ccc(Cl)c2F)ncn1]

To a RBF equipped with a stirring bar and condenser was added 4-(3-chloro-2-fluoro-6-(4-(trimethylsilyl)-1H-1,2,3-triazol-1-yl)phenyl)-6-methoxypyrimidine (2.71 g, 7.17 mmol), NCS (3.35 g, 25.1 mmol), and silica gel (10.77 g, 179 mmol), followed by ACN (48 ml). The reaction was heated at 80° C. for 1 h, and then cooled to rt. The reaction was filtered, and the filtrate was concentrated. The residue was redissolved in EtOAc and washed with sat NaHCO₃, water, brine, and concentrated. Purification by normal phase chromatography afforded 4-(3-chloro-6-(4-chloro-1H-1,2,3-triazol-1-yl)-2-fluorophenyl)-6-methoxypyrimidine (1.05 g, 43.0% yield) as a yellow solid. MS (ESI) m/z: 340.0 (M+H)⁺. ¹H NMR (400 MHz, CDCl₃) δ 8.68 (d, J=0.7 Hz, 1H), 7.71-7.62 (m, 2H), 7.37 (dd, J=8.6, 1.8 Hz, 1H), 6.84 (s, 1H), 4.02 (s, 3H).

3F. Preparation of 6-(3-Chloro-6-(4-chloro-1H-1,2,3-triazol-1-yl)-2-fluorophenyl)-pyrimidin-4-ol

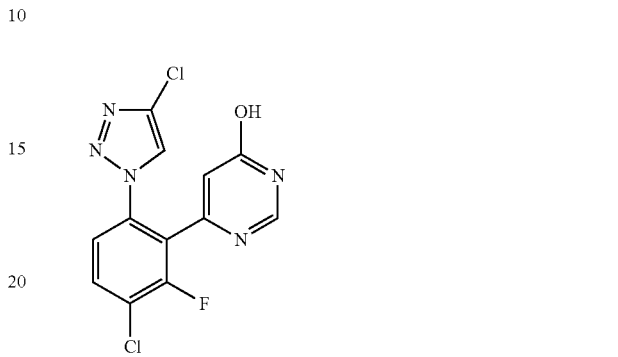

A clear, yellow solution of 4-(3-chloro-6-(4-chloro-1H-1,2,3-triazol-1-yl)-2-fluorophenyl)-6-methoxypyrimidine (1.05 g, 3.09 mmol) in HOAc (15.43 ml) and 48% HBr in water (17.46 ml, 154 mmol) was warmed to 65° C. for 3 h, and then cooled to rt and concentrated. The yellow gum was suspended in EtOAc and washed with sat NaHCO₃ (2×), brine, dried over Na₂SO₄, filtered, and concentrated. To the residue was added Et₂O (10 ml), and the resulting suspension was sonicated, and filtered. The solid was rinsed with Et₂O (2 ml), air-dried with suction to afford 6-(3-chloro-6-(4-chloro-1H-1,2,3-triazol-1-yl)-2-fluorophenyl)pyrimidin-4-ol (0.79 g, 78% yield) as a white solid. MS (ESI) m/z: 326.3 (M+H)⁺. ¹H NMR (400 MHz, CD₃OD) δ 8.35 (s, 1H), 8.08 (d, J=0.7 Hz, 1H), 7.85 (dd, J=8.7, 7.6 Hz, 1H), 7.54 (dd, J=8.6, 1.5 Hz, 1H), 6.57 (s, 1H).

Intermediate 4. Preparation of 6-(3-Chloro-2-fluoro-6-(4-(trifluoromethyl)-1H-1,2,3-triazol-1-yl)phenyl)pyrimidin-4-ol

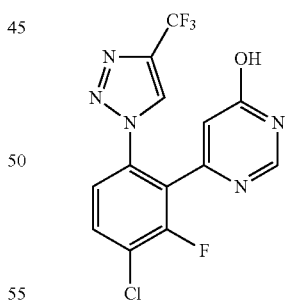

4A. Preparation of 4-(3-Chloro-2-fluoro-6-(4-(trifluoromethyl)-1H-1,2,3-triazol-1-yl)phenyl)-6-methoxypyrimidine To a cooled (0° C.), clear, yellow solution of 4-chloro-3-fluoro-2-(6-methoxypyrimidin-4-yl)aniline (0.2 g, 0.79 mmol) in ACN (11.26 ml) was added isoamyl nitrite (0.16 ml, 1.18 mmol), followed by the dropwise addition of TMSN₃ (0.16 ml, 1.18 mmol). After 10 min, the cold bath was removed, and the reaction was allowed to warm to rt. After 2 h, Cu₂O (0.011 g, 0.079 mmol) was added, then 3,3,3-trifluoroprop-1-yne (0.5 ml, 0.79 mmol) gas was bubbled in through the reaction for 5 min. The reaction was capped and stirred at rt. After 1 h, the reaction was diluted with EtOAc and washed with sat NH$_4$Cl, brine, dried over MgSO$_4$, filtered and concentrated to give a brown oil. Purification by normal phase chromatography afforded 4-(3-chloro-2-fluoro-6-(4-(trifluoromethyl)-1H-1,2,3-triazol-1-yl)phenyl)-6-methoxypyrimidine (0.24 g, 81% yield) as a yellow solid. MS (ESI) m/z: 374.3 (M+H)$^+$.

4B. Preparation of 6-(3-Chloro-2-fluoro-6-(4-(trifluoromethyl)-1H-1,2,3-triazol-1-yl)phenyl)pyrimidin-4-ol A clear, yellow solution of 4-(3-chloro-2-fluoro-6-(4-(trifluoromethyl)-1H-1,2,3-triazol-1-yl)phenyl)-6-methoxypyrimidine (0.1 g, 0.268 mmol) in HOAc (1.34 ml) and 48% HBr in water (1.5 ml, 13.4 mmol) was warmed to 65° C. for 3 h, and then cooled to rt and concentrated. The yellow gum was suspended with EtOAc, washed with sat NaHCO$_3$ (2×), brine, dried over Na$_2$SO$_4$, filtered, and concentrated. To the residue was added Et$_2$O (3 ml). The resulting suspension was sonicated, and filtered. The solid was rinsed with Et$_2$O (2 ml), air-dried with suction to afford 6-(3-chloro-2-fluoro-6-(4-(trifluoromethyl)-1H-1,2,3-triazol-1-yl)phenyl)pyrimidin-4-ol (0.07 g, 72.7% yield) as a white solid. MS (ESI) m/z: 360.0 (M+H)$^+$. $^1$H NMR (400 MHz, CD$_3$OD) δ 8.84 (s, 1H), 8.03 (br. s., 1H), 7.91-7.84 (m, 1H), 7.58 (dd, J=8.8, 1.5 Hz, 1H), 6.61 (br. s., 1H).

Intermediate 5. Preparation of 6-{5-Chloro-2-[4-(trifluoromethyl)-1H-1,2,3-triazol-1-yl]phenyl}pyrimidin-4-ol

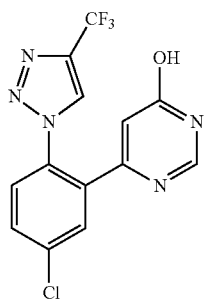 [SMILES: Oc1cc(-c2cc(Cl)ccc2-n2cc(C(F)(F)F)nn2)ncn1]

5A. Preparation of 4-{5-Chloro-2-[4-(trifluoromethyl)-1H-1,2,3-triazol-1-yl]phenyl}-6-methoxypyrimidine

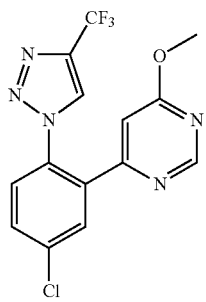 [SMILES: COc1cc(-c2cc(Cl)ccc2-n2cc(C(F)(F)F)nn2)ncn1]

To a solution of 4-chloro-2-(6-methoxypyrimidin-4-yl)aniline (1.0 g, 4.24 mmol), prepared as described in Example 2B, in ACN (60 ml) at 0° C. was added 3-methylbutyl nitrite (0.86 ml, 6.36 mmol) followed by the dropwise addition of TMSN$_3$ (0.84 ml, 6.36 mmol). Gas evolution was observed. After 10 min, the ice bath was removed, and the reaction was allowed to warm to rt. After 2 h, Cu$_2$O (61 mg, 0.42 mmol) was added followed by a slow bubbling of 3,3,3-trifluoroprop-1-yne gas over a period of 5 min. After an additional 10 min, the reaction was partitioned between DCM and sat NH$_4$Cl and then the layers were separated. The organic layer was washed with brine, dried over MgSO$_4$, filtered and concentrated. Purification by normal phase chromatography gave 4-{5-chloro-2-[4-(trifluoromethyl)-1H-1,2,3-triazol-1-yl]phenyl}-6-methoxypyrimidine (1.46 g, 97% yield) as a yellow solid. MS(ESI) m/z: 356.1 (M+H)$^+$. $^1$H NMR (400 MHz, CDCl$_3$) δ 8.62 (d, J=1.1 Hz, 1H), 8.00 (d, J=0.7 Hz, 1H), 7.75 (d, J=2.4 Hz, 1H), 7.66-7.60 (m, 1H), 7.52 (d, J=8.6 Hz, 1H), 6.60 (d, J=1.1 Hz, 1H), 3.98 (s, 3H). $^{19}$F NMR (376 MHz, CDCl$_3$) δ −61.10 (s).

5B. Preparation of 6-{5-Chloro-2-[4-(trifluoromethyl)-1H-1,2,3-triazol-1-yl]phenyl}pyrimidin-4-ol

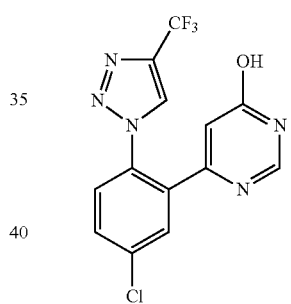

To a solution of 4-{5-chloro-2-[4-(trifluoromethyl)-1H-1,2,3-triazol-1-yl]phenyl}-6-methoxypyrimidine (1.46 g, 4.10 mmol) in AcOH (10 ml) was added 48% HBr in water (5 ml, 44.2 mmol). The mixture was stirred at 85° C. for 1 h. The reaction was concentrated to dryness and then partitioned between EtOAc and sat aq NaHCO$_3$. The layers were separated and the aqueous layer was extracted with EtOAc (2×). The organic layers were combined and washed with sat NaHCO$_3$, brine, dried over MgSO$_4$, filtered and the solvent was reduced under vacuum until some solid started to form. The resulting suspension was triturated with Et$_2$O. The solid was filtered and washed with Et$_2$O to give 6-{5-chloro-2-[4-(trifluoromethyl)-1H-1,2,3-triazol-1-yl]phenyl}pyrimidin-4-ol (1 g, 71.3% yield) as a pale yellow solid. MS(ESI) m/z: 342.0 (M+H)$^+$. $^1$H NMR (400 MHz, CD$_3$OD) δ 8.83 (d, J=0.7 Hz, 1H), 7.99 (d, J=0.9 Hz, 1H), 7.87 (d, J=2.2 Hz, 1H), 7.79-7.72 (m, 1H), 7.70-7.62 (m, 1H), 6.45 (d, J=0.9 Hz, 1H). $^{19}$F NMR (376 MHz, CD$_3$OD) δ −62.61 (s).

Intermediate 6. Preparation of 6-{5-Chloro-2-[4-(difluoromethyl)-1H-1,2,3-triazol-1-yl]phenyl}pyrimidin-4-ol

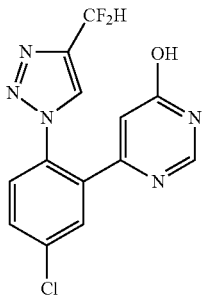 [SMILES: Oc1cc(-c2cc(Cl)ccc2-n2cc(C(F)(F)F)nn2)ncn1]

6A. Preparation of {1-[4-Chloro-2-(6-methoxypyrimidin-4-yl)phenyl]-1H-1,2,3-triazol-4-yl}methanol

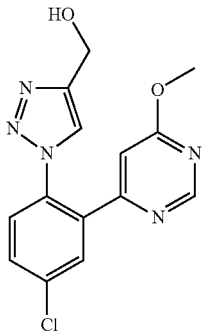 [SMILES: COc1cc(-c2cc(Cl)ccc2-n2cc(CO)nn2)ncn1]

{1-[4-Chloro-2-(6-methoxypyrimidin-4-yl)phenyl]-1H-1,2,3-triazol-4-yl}methanol (0.44 g, 52.5% yield) was prepared in a similar manner as the procedure described for the preparation of 4-{5-chloro-2-[4-(trimethylsilyl)-1H-1,2,3-triazol-1-yl]phenyl}-6-methoxypyrimidine, as described in Example 2C, by replacing ethynyltrimethylsilane with propargyl alcohol (0.38 ml, 6.36 mmol). MS(ESI) m/z: 318.3 (M+H)$^+$. $^1$H NMR (400 MHz, CDCl$_3$) δ 8.66 (d, J=1.1 Hz, 1H), 7.77 (d, J=2.2 Hz, 1H), 7.63 (s, 1H), 7.61-7.55 (m, 1H), 7.51-7.46 (m, 1H), 6.42 (d, J=1.1 Hz, 1H), 4.77 (d, J=5.9 Hz, 2H), 3.93 (s, 3H).

6B. Preparation of 1-[4-Chloro-2-(6-methoxypyrimidin-4-yl)phenyl]-1H-1,2,3-triazole-4-carbaldehyde

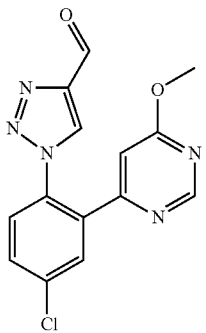 [SMILES: COc1cc(-c2cc(Cl)ccc2-n2cc(C=O)nn2)ncn1]

To a solution of {1-[4-chloro-2-(6-methoxypyrimidin-4-yl)phenyl]-1H-1,2,3-triazol-4-yl}methanol (95 mg, 0.3 mmol) in DMSO (1 mL) was added IBX (92 mg, 0.33 mmol) and the reaction was stirred at rt for 14 h. Water and sat NaHCO$_3$ were added and the mixture was extracted with EtOAc (2×). The organic layers were combined, concentrated and purified by normal phase chromatography to give 1-[4-chloro-2-(6-methoxy pyrimidin-4-yl)phenyl]-1H-1,2,3-triazole-4-carbaldehyde (82 mg, 87% yield) as a white solid. MS(ESI) m/z: 316.3 (M+H)$^+$. $^1$H NMR (400 MHz, CDCl$_3$) δ 10.16 (s, 1H), 8.62 (d, J=1.1 Hz, 1H), 8.21 (s, 1H), 7.76 (d, J=2.2 Hz, 1H), 7.64 (dd, J=8.5, 2.3 Hz, 1H), 7.53 (d, J=8.4 Hz, 1H), 6.59 (d, J=1.1 Hz, 1H), 3.97 (s, 3H).

6C. Preparation of 4-{5-Chloro-2-[4-(difluoromethyl)-1H-1,2,3-triazol-1-yl]phenyl}-6-methoxypyrimidine

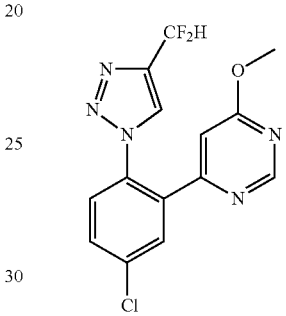

To a solution of 1-[4-chloro-2-(6-methoxypyrimidin-4-yl)phenyl]-1H-1,2,3-triazole-4-carbaldehyde (427 mg, 1.35 mmol) in DCM (30 ml) was added DAST (0.54 ml, 4.1 mmol) and the reaction was stirred overnight at rt. The reaction was quenched with water and extracted with DCM. The organic layer was concentrated and purified by normal phase chromatography to give 4-{5-chloro-2-[4-(difluoromethyl)-1H-1,2,3-triazol-1-yl]phenyl}-6-methoxypyrimidine (441 mg, 97% yield) as a yellow solid. MS(ESI) m/z: 338.3 (M+H)$^+$. $^1$H NMR (400 MHz, CDCl$_3$) δ 8.65 (d, J=0.9 Hz, 1H), 7.89 (s, 1H), 7.76 (d, J=2.4 Hz, 1H), 7.62 (dd, J=8.5, 2.3 Hz, 1H), 7.55-7.47 (m, 1H), 6.89 (t, J=54.6 Hz, 1H), 6.52 (d, J=1.1 Hz, 1H), 4.03-3.87 (m, 3H). $^{19}$F NMR (376 MHz, CDCl$_3$) δ −112.40 (s).

6D. Preparation of 6-{5-Chloro-2-[4-(difluoromethyl)-1H-1,2,3-triazol-1-yl]phenyl}pyrimidin-4-ol

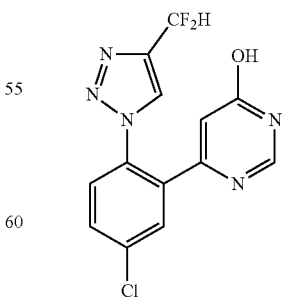

6-{5-Chloro-2-[4-(difluoromethyl)-1H-1,2,3-triazol-1-yl]phenyl}pyrimidin-4-ol (370 mg, 88% yield) was prepared in a similar manner as the procedure described in Example 2E, by replacing 4-[5-chloro-2-(4-chloro-1H-1,2,3-triazol-1-yl)phenyl]-6-methoxypyrimidine with 4-{5-chloro-2-[4-(difluoromethyl)-1H-1,2,3-triazol-1-yl]phenyl}-6-methoxypyrimidine (441 mg, 1.31 mmol). MS(ESI) m/z: 324.3 (M+H)$^+$. $^1$H NMR (400 MHz, CDCl$_3$) δ 8.04 (s, 1H), 7.86 (s, 1H), 7.71 (d, J=2.2 Hz, 1H), 7.67-7.61 (m, 1H), 7.51 (d, J=8.6 Hz, 1H), 6.92 (t, J=54.6 Hz, 1H), 6.43 (d, J=0.7 Hz, 1H). $^{19}$F NMR (376 MHz, CDCl$_3$) δ −112.69 (s).

Intermediate 7. Preparation of 1-(3-Chloro-2,6-difluorophenyl)prop-2-en-1-one

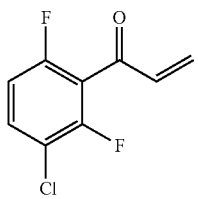

7A. Preparation of 1-(3-Chloro-2,6-difluorophenyl)prop-2-en-1-ol

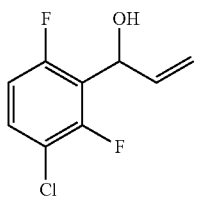

To a 100 mL dry RBF containing vinylmagnesium bromide (1 M in THF) (24 ml, 24.00 mmol) under Ar at 0° C. was added 3-chloro-2,6-difluorobenzaldehyde (3.2 g, 18.13 mmol) in THF (10 ml) dropwise. The reaction was stirred for 1 h and quenched with 1 N HCl to pH 2. The mixture was extracted with Et$_2$O (3×). The combined organic layer was washed with brine, dried over MgSO$_4$, filtered, and concentrated to yield 1-(3-chloro-2,6-difluorophenyl)prop-2-en-1-ol (3.71 g, 100%) as a pale yellow oil. $^1$H NMR (500 MHz, CDCl$_3$) δ 7.34 (ddd, J=8.9, 8.1, 5.8 Hz, 1H), 6.90 (td, J=9.2, 1.7 Hz, 1H), 6.23 (dddt, J=17.2, 10.4, 5.8, 1.2 Hz, 1H), 5.60 (dd, J=7.6, 6.7 Hz, 1H), 5.40-5.31 (m, 1H), 5.28 (dt, J=10.2, 1.2 Hz, 1H), 2.38 (dt, J=8.3, 1.9 Hz, 1H).

7B. Preparation of 1-(3-Chloro-2,6-difluorophenyl)prop-2-en-1-one

To a solution of 1-(3-chloro-2,6-difluorophenyl)prop-2-en-1-ol (3.7 g, 18.08 mmol) in acetone (90 ml) at 0° C. was added Jones' reagent (8.77 ml, 23.51 mmol) dropwise. Upon finishing addition of Jones' reagent, the reaction was quenched with isopropanol. The mixture was concentrated. The residue was suspended in water and extracted with DCM (3×). The combined organic layer was washed with brine, dried over MgSO$_4$, filtered, and concentrated. The residue was purified by silica gel chromatography to yield 1-(3-chloro-2,6-difluorophenyl)prop-2-en-1-one as a yellow oil (3.45 g, 94%) which solidified in freezer. $^1$H NMR (500 MHz, CDCl$_3$) δ 7.48 (ddd, J=9.0, 8.0, 5.5 Hz, 1H), 7.05-6.91 (m, 1H), 6.70 (ddt, J=17.5, 10.5, 1.1 Hz, 1H), 6.29-6.11 (m, 2H).

Intermediate 8. Preparation of 1-(5-Chloro-2-(4-chloro-1H-1,2,3-triazol-1-yl)phenyl)prop-2-en-1-one

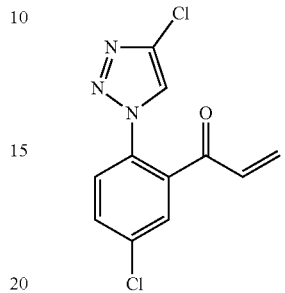

8A. Preparation of 2-Azido-5-chlorobenzaldehyde

A solution of 5-chloro-2-fluorobenzaldehyde (1.38 g, 8.70 mmol) and NaN$_3$ (0.58 g, 8.92 mmol) in DMF (4 ml) was stirred at 55° C. for 8 h then cooled to rt. The reaction mixture was diluted with Et$_2$O and water which was then acidified with 1N HCl to pH 4. The ertheral layer was washed with water (3×) followed by brine (3×), then dried over MgSO$_4$ and filtered. The organic layers were then concentrated under vacuum to yield 1.47 g of 2-azido-5-chlorobenzaldehyde (93%) as pale yellow solid. $^1$H NMR (400 MHz, CDCl$_3$-d) δ 10.30 (s, 1H), 7.86 (d, J=2.6 Hz, 1H), 7.58 (dd, J=8.7, 2.5 Hz, 1H), 7.24 (d, J=8.6 Hz, 1H)

8B. Preparation of 5-Chloro-2-(4-(tributylstannyl)-1H-1,2,3-triazol-1-yl)benzaldehyde A solution of 2-azido-5-chlorobenzaldehyde (386 mg, 2.126 mmol) and tributylstanylacetylene (0.65 mL, 2.13 mmol) in toluene (5 ml) was heated at 100° C. for 5 h before cooling down to rt. After 5 h, the reaction mixture was concentrated and directly purified using normal phase chromatography to yield 495 mg of 5-chloro-2-(4-(tributylstannyl)-1H-1,2,3-triazol-1-yl)benzaldehyde (43%) as pale yellow oil. MS (ESI) m/z: 498.1 (M+H)$^+$.

8C. Preparation of 5-Chloro-2-(4-chloro-1H-1,2,3-triazol-1-yl)benzaldehyde

To a solution of 5-chloro-2-(4-(tributylstannyl)-1H-1,2,3-triazol-1-yl)benzaldehyde (459 mg, 0.924 mmol) in ACN (5 ml) was added NCS (185 mg, 1.386 mmol) and the reaction was then heated at 60° C. for 15 h. After 15 h, the reaction mixture was concentrated and directly purified using normal phase chromatography to yield 117 mg of 5-chloro-2-(4-chloro-1H-1,2,3-triazol-1-yl)benzaldehyde (52%) as white solid. MS (ESI) m/z: 242.0 (M+H, Chlorine isotope peak)$^+$.

8D. Preparation of 1-(5-Chloro-2-(4-chloro-1H-1,2,3-triazol-1-yl)phenyl)prop-2-en-1-one 1-(5-Chloro-2-(4-chloro-1H-1,2,3-triazol-1-yl)phenyl)prop-2-en-1-one was prepared using a procedure analogous to that used for the preparation of Intermediate 7 by replacing 3-chloro-2,6-difluorobenzaldehyde with 5-chloro-2-(4- chloro-1H-1,2,3-triazol-1-yl)benzaldehyde. MS (ESI) m/z: 268.3 (M+H)+. 1H NMR (400 MHz, CDCl3) δ 7.71-7.66 (m, 1H), 7.62-7.52 (m, 2H), 7.44 (d, J=8.4 Hz, 1H), 6.29 (dd, J=17.6, 10.6 Hz, 1H), 5.98-5.79 (m, 2H).

Intermediate 9. Preparation of (3R,7S)-7-Amino-3-methyl-4,5,6,7,9,10-hexahydrobenzo[b][1,5]-diaza-cyclododecine-2,8 (1H,3H)-dione

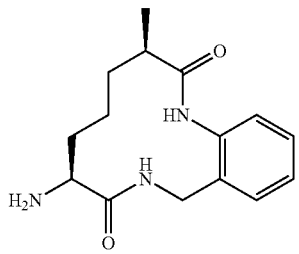 [SMILES: C[C@@H]1CCC[C@H](N)C(=O)NCc2ccccc2NC1=O]

9A. Preparation of (S)-tert-Butyl (1-((2-nitrobenzyl)amino)-1-oxopent-4-en-2-yl)carbamate

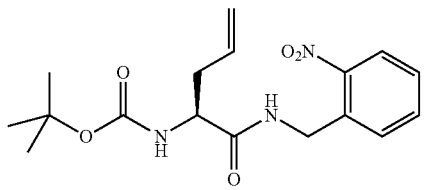 [SMILES: C=CC[C@H](NC(=O)OC(C)(C)C)C(=O)NCc1ccccc1[N+](=O)[O-]]

4-Methylmorpholine (1.40 ml, 12.72 mmol) was added to a stirring solution of (S)-2-((tert-butoxycarbonyl)amino) pent-4-enoic acid (1.369 g, 6.36 mmol), (2-nitrophenyl) methanamine, HCl (1.2 g, 6.36 mmol), and HATU (3.63 g, 9.54 mmol) in DMF (25.4 ml) at rt. After 14 h, the reaction mixture was partition between EtOAc and water. The organic layer was washed with brine, dried over Na2CO3, filtered, and concentrated. The crude material was purified by normal phase chromatography to give (S)-tert-butyl (1-((2-nitrobenzyl)amino)-1-oxopent-4-en-2-yl)carbamate (1.99 g, 5.68 mmol, 89%). MS (ESI) m/z: 350.1 (M+H)+. 1H NMR (400 MHz, CDCl3) δ 8.06 (dd, J=8.0, 0.8 Hz, 1H), 7.67-7.58 (m, 2H), 7.49-7.43 (m, 1H), 6.99-6.91 (m, 1H), 5.76-5.63 (m, 1H), 5.14-5.07 (m, 2H), 4.78-4.64 (m, 2H), 2.57-2.44 (m, 2H), 1.42 (s, 9H).

9B. Preparation of (S)-tert-Butyl (1-((2-aminobenzyl)amino)-1-oxopent-4-en-2-yl)carbamate

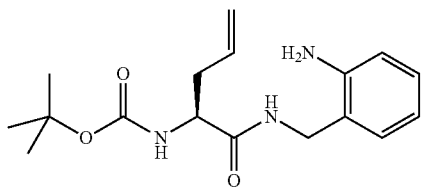 [SMILES: C=CC[C@H](NC(=O)OC(C)(C)C)C(=O)NCc1ccccc1N]

(S)-tert-Butyl (1-((2-nitrobenzyl)amino)-1-oxopent-4-en-2-yl)carbamate (1.985 g, 5.68 mmol) was dissolved in acetone (40 ml) and H2O (8 ml), cooled to 0° C. Zn powder (3.71 g, 56.8 mmol) and NH4Cl (1.520 g, 28.4 mmol) were then added and the reaction mixture was allowed to gradually come to rt. The reaction was filtered and filtrate concentrated. The residue was partitioned between water (50 ml) and EtOAc (100 ml). The aqueous layer was extracted with EtOAc (2×50 ml). The combined organic layers were washed with brine (50 ml) and dried (MgSO4) to give (S)-tert-butyl (1-((2-aminobenzyl)amino)-1-oxopent-4-en-2-yl)carbamate (1.73 g, 5.42 mmol, 95%) as a colorless oil. This material was carried forward as is. MS (ESI) m/z: 320.1 (M+H)+. 1H NMR (400 MHz, CDCl3) δ 7.13-7.01 (m, 2H), 6.72-6.63 (m, 2H), 6.60-6.52 (m, 1H), 5.72 (ddt, J=17.1, 10.1, 7.1 Hz, 1H), 5.17-5.06 (m, 2H), 4.44-4.30 (m, 2H), 2.58-2.41 (m, 2H), 1.40 (s, 9H).

9C. Preparation of tert-Butyl ((S)-1-((2-((R)-2-methylbut-3-enamido)benzyl)amino)-1-oxopent-4-en-2-yl)carbamate

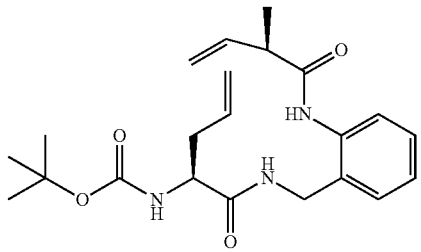 [SMILES: C=CC[C@H](NC(=O)OC(C)(C)C)C(=O)NCc1ccccc1NC(=O)[C@H](C)C=C]

(R)-2-Methylbut-3-enoic acid (0.75 g, 7.45 mmol), (S)-tert-butyl (1-((2-aminobenzyl)amino)-1-oxopent-4-en-2-yl) carbamate (1.7 g, 5.32 mmol), pyridine (1.29 ml, 15.97 mmol) in EtOAc (56.6 ml) was cooled down to 0° C., T3P (50% wt in EtOAc) (6.77 g, 10.65 mmol) was added, stirred at 0° C., and then allowed to gradually warmed up to rt. After 5 h, reaction mixture was concentrated and purified by normal phase chromatography to give tert-butyl ((S)-1-((2-((R)-2-methylbut-3-enamido)benzyl)amino)-1-oxopent-4-en-2-yl)carbamate (1.98 g, 93%). MS (ESI) m/z: 402.2 (M+H)+. 1H NMR (400 MHz, CDCl3) δ 8.06 (d, J=8.3 Hz, 1H), 7.34-7.28 (m, 1H), 7.19 (dd, J=7.6, 1.5 Hz, 1H), 7.09-7.05 (m, 1H), 6.86-6.79 (m, 1H), 6.12-6.01 (m, 1H), 5.73-5.61 (m, 1H), 5.35-5.28 (m, 2H), 5.20-5.06 (m, 3H), 4.36 (br. s., 1H), 3.35 (quin, J=7.2 Hz, 1H), 2.59-2.51 (m, 1H), 2.50-2.43 (m, 1H), 1.57-1.56 (m, 1H), 1.43-1.32 (m, 11H).

9D. Preparation of tert-Butyl ((3R,7S,E)-3-methyl-2,8-dioxo-1,2,3,6,7,8,9,10-octahydrobenzo[b][1,5] diazacyclododecin-7-yl)carbamate

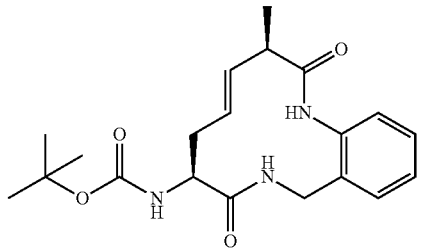 [SMILES: C[C@@H]1/C=C/C[C@H](NC(=O)OC(C)(C)C)C(=O)NCc2ccccc2NC1=O]

tert-Butyl ((S)-1-((2-((R)-2-methylbut-3-enamido)benzyl)amino)-1-oxopent-4-en-2-yl)carbamate (0.500 g, 1.25 mmol) was dissolved in EtOAc (733 ml) and the resulting solution was degassed with a stream of Ar for 30 min. Grubbs II (0.424 g, 0.498 mmol) was added and the solution heated at 60° C. for overnight. The reaction mixture concentrated and purified by normal phase chromatography give tert-butyl ((3R,7S,E)-3-methyl-2,8-dioxo-1,2,3,6,7,8,9,10-octahydrobenzo[b][1,5]diazacyclododecin-7-yl)carbamate (0.241 g, 51.8% yield) as a tan solid. MS (ESI) m/z: 374 (M+H)+. 1H NMR (400 MHz, CDCl3) δ 8.39 (br. s., 1H), 8.30 (d, J=8.1 Hz, 1H), 7.34 (t, J=7.7 Hz, 1H), 7.17 (d, J=7.5 Hz, 1H), 7.11-7.01 (m, 1H), 6.39 (br. s., 1H), 5.80-5.60 (m, 2H), 5.25 (d, J=7.0 Hz, 1H), 4.91-4.80 (m, 1H), 3.96 (d, J=13.9 Hz, 1H), 3.24-3.12 (m, 1H), 1.65 (s, 2H), 1.47-1.32 (m, 12H).

9E. Preparation of tert-Butyl ((3R,7S)-3-methyl-2,8-dioxo-1,2,3,4,5,6,7,8,9,10-decahydrobenzo[b][1,5]diazacyclododecin-7-yl)carbamate

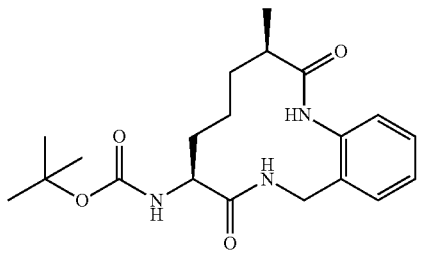 [SMILES: C[C@@H]1CCC[C@H](NC(=O)OC(C)(C)C)C(=O)NCc2ccccc2NC1=O]

PtO2 (0.015 g, 0.065 mmol) was added to a solution of tert-butyl ((3R,7S,E)-3-methyl-2,8-dioxo-1,2,3,6,7,8,9,10-octahydrobenzo[b][1,5]diazacyclododecin-7-yl)carbamate (0.241 g, 0.645 mmol) in EtOH (25.8 ml) and subjected to a hydrogen atmosphere (55 psi) overnight. After this time the suspension was filtered through a plug of Celite® and filtrate concentrated to give tert-butyl ((3R,7S)-3-methyl-2,8-dioxo-1,2,3,4,5,6,7,8,9,10-decahydrobenzo[b][1,5]diazacyclododecin-7-yl)carbamate. MS (ESI) m/z: 376 (M+H)+.

9F. Preparation of (3R,7S)-7-Amino-3-methyl-4,5,6,7,9,10-hexahydrobenzo[b][1,5]diaza-cyclododecine-2,8(1H,3H)-dione

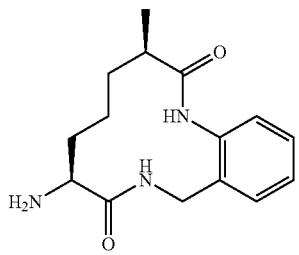 [SMILES: C[C@@H]1CCC[C@H](N)C(=O)NCc2ccccc2NC1=O]

TFA (0.616 mL, 7.99 mmol) was added to a stirring solution of tert-butyl ((3R,7S)-3-methyl-2,8-dioxo-1,2,3,4,5,6,7,8,9,10-decahydrobenzo[b][1,5]diazacyclododecin-7-yl)carbamate (0.150 g, 0.400 mmol) in DCM (10 ml). After 3 h, the reaction mixture was concentrated to dryness. The residue was partitioned between EtOAc and sat NaHCO3 solution. The organic layer was washed with brine, dried over Na2SO4, filtered, and concentrated to give (3R,7S)-7-amino-3-methyl-4,5,6,7,9,10-hexahydrobenzo[b][1,5]diazacyclododecine-2,8(1H,3H)-dione (0.063 g, 0.229 mmol, 57.3%) as a tan solid. MS (ESI) m/z: 276 (M+H)+.

Intermediate 10. Preparation of (3R,7S)-7-Amino-12-fluoro-3-methyl-4,5,6,7,9,10-hexahydrobenzo[b][1,5]diazacyclododecine-2,8(1H,3H)-dione

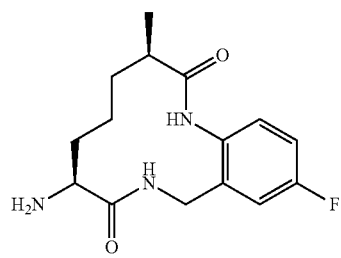 [SMILES: C[C@@H]1CCC[C@H](N)C(=O)NCc2cc(F)ccc2NC1=O]

10A. Preparation of tert-Butyl (2-(azidomethyl)-4-fluorophenyl)carbamate

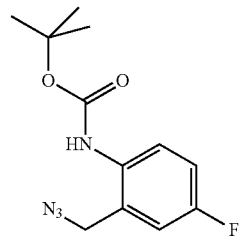 [SMILES: CC(C)(C)OC(=O)Nc1ccc(F)cc1CN=[N+]=[N-]]

NaBH4 (0.474 g, 12.54 mmol) was added portion-wise to a solution of tert-butyl (4-fluoro-2-formylphenyl)carbamate (1.0 g, 4.18 mmol) in MeOH (25 ml) at rt. After stirring for 1 h, the reaction mixture was concentrated. The residue was partitioned between EtOAc and brine. The organic layer was dried over Na2SO4, filtered, and concentrated. The resulting solid was washed with hexane to give the desired alcohol intermediate. To the alcohol intermediate in THF (25 ml) under a nitrogen atmosphere at 0° C. was added DBU (1.250 ml, 8.29 mmol). After 5 min, diphenylphosphoryl azide (1.34 ml, 6.22 mmol) was added dropwise. The mixture was allowed to gradually come to rt and stir overnight. The reaction mixture was concentrated, diluted with EtOAc, washed with water followed by brine, dried over Na2SO4, filtered, and concentrated. The crude material was purified by normal phase chromatography to give tert-butyl (2-(azidomethyl)-4-fluorophenyl)carbamate (0.840 g, 3.15 mmol, 76% yield) as a clear oil which slowly solidified. 1H NMR (400 MHz, CDCl3) δ 7.74 (dd, J=7.9, 5.1 Hz, 1H), 7.09-6.97 (m, 2H), 6.64 (br. s., 1H), 4.33 (s, 2H), 1.52 (s, 9H).

10B. Preparation of tert-Butyl (2-(aminomethyl)-4-fluorophenyl)carbamate

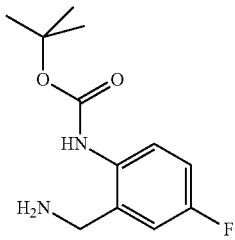 [SMILES: CC(C)(C)OC(=O)Nc1ccc(F)cc1CN]

10% Pd/C (H₂O content 50%, 200 mg) was added to a solution of tert-butyl (2-(azidomethyl)-4-fluorophenyl)carbamate (0.84 g, 3.15 mmol) in EtOAc (31.5 ml) and the resulting reaction mixture subjected to a hydrogen atmosphere (55 psi). After 3 h, the suspension was filtered through a plug of Celite® and the filtrate concentrated to give tert-butyl (2-(aminomethyl)-4-fluorophenyl)carbamate which was carried forward to the next reaction without further purification. MS (ESI) m/z: 241 (M+H)⁺.

10C. Preparation of Benzyl N-[(1S)-1-{[(2-{[(tert-butoxy)carbonyl]amino}-5-fluorophenyl)methyl]carbamoyl}but-3-en-1-yl]carbamate

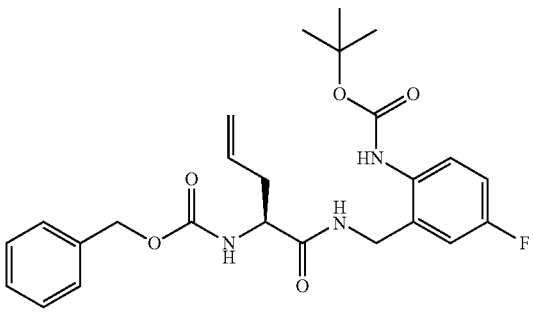 [SMILES: C=CC[C@H](NC(=O)OCc1ccccc1)C(=O)NCc1cc(F)ccc1NC(=O)OC(C)(C)C]

To a solution of (S)-2-(((benzyloxy)carbonyl)amino)pent-4-enoic acid (0.971 g, 3.90 mmol), tert-butyl (2-(aminomethyl)-4-fluorophenyl)carbamate (0.936 g, 3.90 mmol), and pyridine (0.945 ml, 11.69 mmol) in EtOAc (39.0 ml), T3P (50% wt in EtOAc) (4.64 ml, 7.79 mmol) was added dropwise at 0° C. The reaction was warmed slowly to rt. After stirring for 14 h, the reaction mixture was diluted with EtOAc, washed with water, extracted again with EtOAc. The combined organic layers was washed with brine, dried over MgSO₄, filtered and concentrated. The crude material was purified by normal phase chromatography to give benzyl N-[(1S)-1-{[(2-{[(tert-butoxy)carbonyl]amino}-5-fluorophenyl)methyl]carbamoyl}but-3-en-1-yl]carbamate (0.969 g, 52.3%) as a white solid. MS (ESI) m/z: 472 (M+H)⁺. ¹H NMR (400 MHz, CDCl₃) δ 7.68 (dd, J=8.4, 5.1 Hz, 1H), 7.39-7.31 (m, 5H), 7.01-6.96 (m, 1H), 6.93-6.89 (m, 1H), 6.75-6.70 (m, 1H), 5.72-5.62 (m, 1H), 5.21-5.16 (m, 1H), 5.13-5.08 (m, 4H), 4.40-4.34 (m, 1H), 4.31 (br. s., 1H), 4.22 (d, J=6.9 Hz, 1H), 2.53 (t, J=6.7 Hz, 2H), 1.53 (s, 9H).

10D. Preparation of Benzyl N-[(1S)-1-{[(2-amino-5-fluorophenyl)methyl]carbamoyl}but-3-en-1-yl]carbamate

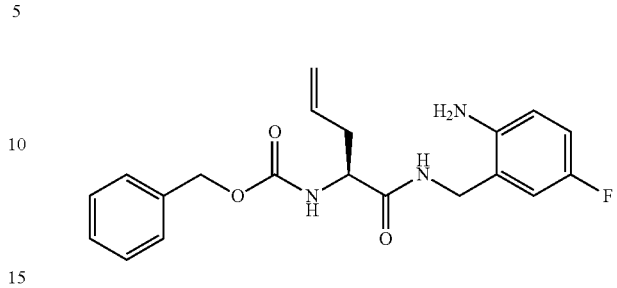

TFA (0.817 mL, 10.60 mmol) was added to a stirring solution of benzyl N-[(1S)-1-{[(2-{[(tert-butoxy)carbonyl]amino}-5-fluorophenyl)methyl]carbamoyl}but-3-en-1-yl]carbamate (0.500 g, 1.060 mmol) in DCM (10 ml). After 2 h, the reaction mixture was concentrated, dissolved in EtOAc, and neutralized with 1.5 M potassium phosphate solution. The organic layer was washed with brine, dried over Na₂SO₄, filtered, and concentrated to give (S)-benzyl (1-((2-amino-5-fluorobenzyl)amino)-1-oxopent-4-en-2-yl)carbamate (0.373 g, 95%) as a white solid which was carried forward to the next step. MS (ESI) m/z: 372 (M+H)⁺. ¹H NMR (400 MHz, DMSO-d6) δ 8.38 (t, J=5.9 Hz, 1H), 7.47 (d, J=8.1 Hz, 1H), 7.39-7.29 (m, 5H), 6.83-6.75 (m, 2H), 6.60 (dd, J=8.6, 5.1 Hz, 1H), 5.79-5.69 (m, 1H), 5.11-5.01 (m, 4H), 4.87 (br. s., 2H), 4.13-4.05 (m, 3H), 2.47-2.40 (m, 1H), 2.35-2.26 (m, 1H).

10E. Preparation of Benzyl N-[(1 S)-1-[({5-fluoro-2-[(2R)-2-methylbut-3-enamido]-phenyl}methyl)carbamoyl]but-3-en-1-yl]carbamate

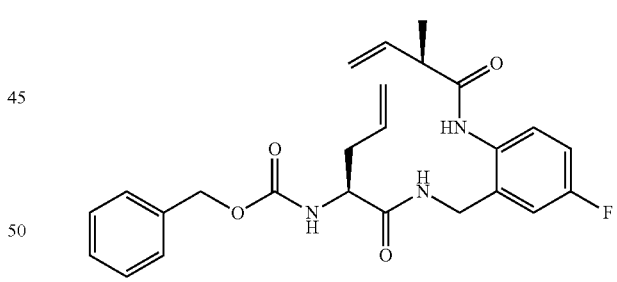

(R)-2-Methylbut-3-enoic acid (0.136 g, 1.357 mmol), benzyl N-[(1S)-1-{[(2-amino-5-fluorophenyl)methyl]carbamoyl}but-3-en-1-yl]carbamate (0.36 g, 0.97 mmol), pyridine (0.235 ml, 2.91 mmol) in EtOAc (10.31 ml) was cooled to 0° C., T3P (50% wt in EtOAc) (1.234 g, 1.94 mmol) was added, stirred at 0° C., then allowed to gradually warmed up to rt. After 5 h, the reaction mixture was concentrated and purified by normal phase chromatography to afford benzyl N-[(1 S)-1-[({5-fluoro-2-[(2R)-2-methylbut-3-enamido]-phenyl}methyl)carbamoyl]but-3-en-1-yl]carbamate (0.086 g, 19.6%) as a film. MS (ESI) m/z: 454 (M+H)⁺.

10F. Preparation of Benzyl N-[(3R,7S)-12-fluoro-3-methyl-2,8-dioxo-1,2,3,6,7,8,9,10-octahydro-1,9-benzodiazacyclododecin-7-yl]carbamate

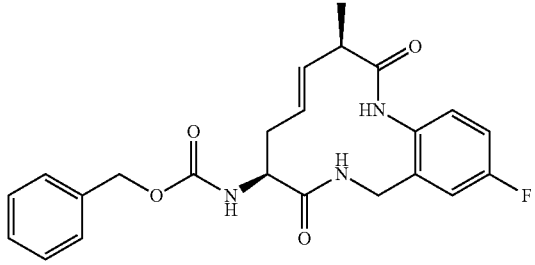 [SMILES: C[C@@H]1/C=C/C[C@H](NC(=O)OCc2ccccc2)C(=O)NCc2cc(F)ccc2NC1=O]

Benzyl N-[(1S)-1-[({5-fluoro-2-[(2R)-2-methylbut-3-enamido]-phenyl}methyl)carbamoyl]but-3-en-1-yl]carbamate (0.086 g, 0.190 mmol) was added to EtOAc (19 ml). The solution was degassed with a stream of Ar for 30 min. Grubbs II (0.065 g, 0.076 mmol) was added and the mixture heated at 60° C. for overnight. The reaction mixture was cooled to rt and absorbed onto silica gel. The crude material was purified by normal phase chromatography to benzyl N-[(3R,7S)-12-fluoro-3-methyl-2,8-dioxo-1,2,3,6,7,8,9,10-octahydro-1,9-benzodiazacyclododecin-7-yl]carbamate (0.0374 g, 0.088 mmol, 46.4%) as a beige solid. (ESI) m/z: 425 (M+H)$^+$.

10G. Preparation of (3R,7S)-7-Amino-12-fluoro-3-methyl-4,5,6,7,9,10-hexahydrobenzo-[b][1,5]diaza-cyclododecine-2,8(1H,3H)-dione

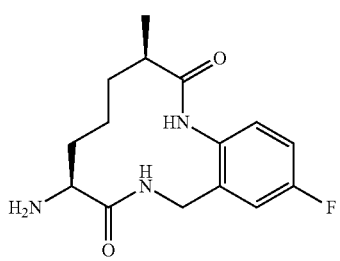 [SMILES: C[C@@H]1CCC[C@H](N)C(=O)NCc2cc(F)ccc2NC1=O]

10% Pd/C (4.63 mg, 0.043 mmol) and PtO$_2$ (9.87 mg, 0.043 mmol) was added to a solution of benzyl N-[(3R,7S)-12-fluoro-3-methyl-2,8-dioxo-1,2,3,6,7,8,9,10-octahydro-1,9-benzodiazacyclododecin-7-yl]carbamate (0.037 g, 0.087 mmol) in EtOH (2 mL)/THF (0.50 mL). The suspension was stirred under a hydrogen atmosphere (55 psi) for 3 h, then was filtered through a plug of Celite. The filtrate concentrated to give 3R,7S)-7-amino-12-fluoro-3-methyl-4,5,6,7,9,10-hexahydrobenzo-[b][1,5]diazacyclododecine-2,8(1H,3H)-dione (0.025 g, 0.085 mmol, 98% yield) as a brown film. (ESI) m/z: 294 (M+H)$^+$.

Example 11. Preparation of (3R,7S)-7-(4-(5-Chloro-2-(4-(trifluoromethyl)-1H-1,2,3-triazol-1-yl)phenyl)-6-oxopyrimidin-1(6H)-yl)-3-methyl-4,5,6,7,9,10-hexahydrobenzo[b][1,5]-diazacyclododecine-2,8(1H,3H)-dione

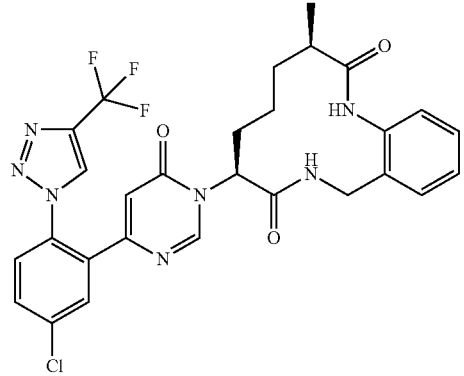 [SMILES: C[C@@H]1CCC[C@H](n2cnc(-c3cc(Cl)ccc3-n3cc(C(F)(F)F)nn3)cc2=O)C(=O)NCc2ccccc2NC1=O]

To an off-white suspension of 6-(5-chloro-2-(4-(trifluoromethyl)-1H-1,2,3-triazol-1-yl)phenyl)pyrimidin-4-ol (0.025 g, 0.073 mmol) and HATU (0.036 g, 0.094 mmol) in ACN (0.726 ml) was added dropwise DBU (0.016 ml, 0.109 mmol). The resulting yellow solution was stirred at rt. After 15 min, a solution of (3R,7S)-7-amino-3-methyl-4,5,6,7,9,10-hexahydrobenzo[b][1,5]-diazacyclododecine-2,8(1H,3H)-dione (0.020 g, 0.073 mmol) in DMF (0.726 ml) was added. After 3 h, the crude reaction mixture was purified by reverse phase chromatography and lyopholized to give (3R,7S)-7-(4-(5-chloro-2-(4-(trifluoromethyl)-1H-1,2,3-triazol-1-yl)phenyl)-6-oxopyrimidin-1(6H)-yl)-3-methyl-4,5,6,7,9,10-hexahydrobenzo[b][1,5]-diazacyclododecine-2,8(1H,3H)-dione (0.006 g, 13.2%) as a white solid. (ESI) m/z: 600 (M+H)$^+$. $^1$H NMR (400 MHz, DMSO-d6) δ 9.19 (d, J=0.7 Hz, 1H), 8.79 (s, 1H), 8.69 (d, J=6.6 Hz, 1H), 8.44 (s, 1H), 7.88 (d, J=2.2 Hz, 1H), 7.83-7.73 (m, 2H), 7.39 (d, J=7.5 Hz, 1H), 7.30-7.22 (m, 2H), 7.11-7.03 (m, 1H), 6.29 (s, 1H), 5.23 (t, J=8.5 Hz, 1H), 4.99 (dd, J=14.4, 6.7 Hz, 1H), 3.77 (d, J=14.3 Hz, 1H), 2.28-2.22 (m, 1H), 1.73 (br. s., 2H), 1.51-1.42 (m, 3H), 1.17 (s, 1H), 1.12-1.07 (m, 3H). Analytical HPLC (Method A) RT=8.03 min, purity=96%; Factor XIa Ki=18.7 nM, Plasma Kallikrein Ki=3,380 nM.

Example 12. Preparation of (3R,7S)-7-(4-(3-Chloro-6-(4-chloro-1H-1,2,3-triazol-1-yl)-2-fluorophenyl)-6-oxopyrimidin-1(6H)-yl)-3-methyl-4,5,6,7,9,10-hexahydrobenzo[b][1,5]diazacyclo-dodecine-2,8(1H,3H)-dione

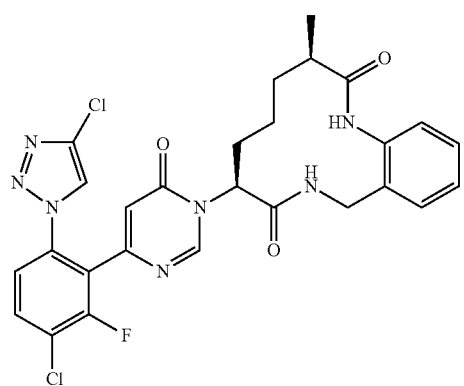 [SMILES: C[C@@H]1CCC[C@H](n2cnc(-c3c(-n4cc(Cl)nn4)ccc(Cl)c3F)cc2=O)C(=O)NCc2ccccc2NC1=O]

(3R,7S)-7-(4-(3-Chloro-6-(4-chloro-1H-1,2,3-triazol-1-yl)-2-fluorophenyl)-6-oxo pyrimidin-1(6H)-yl)-3-methyl-4,5,6,7,9,10-hexahydrobenzo[b][1,5]diazacyclo-dodecine-2,8(1H,3H)-dione (0.004 g, 8.95% yield) was prepared in a similar manner as the procedure described in Example 11, by replacing 6-(5-chloro-2-(4-(trifluoromethyl)-1H-1,2,3-triazol-1-yl)phenyl)pyrimidin-4-ol with 6-(3-chloro-6-(4-chloro-1H-1,2,3-triazol-1-yl)-2-fluorophenyl)pyrimidin-4-ol, prepare as described in Intermediate 3. (ESI) m/z: 584 (M+H)$^+$. $^1$H NMR: (400 MHz, DMSO-d6) δ 8.80 (s, 1H), 8.73-8.66 (m, 2H), 8.51 (s, 1H), 7.94 (t, J=8.3 Hz, 1H), 7.60 (dd, J=8.8, 1.3 Hz, 1H), 7.39 (d, J=7.5 Hz, 1H), 7.31-7.20 (m, 2H), 7.13-7.04 (m, 1H), 6.49 (s, 1H), 5.23 (t, J=8.6 Hz, 1H), 4.98 (dd, J=14.3, 6.6 Hz, 1H), 3.79 (d, J=14.3 Hz, 1H), 2.25 (d, J=4.0 Hz, 1H), 1.77 (br. s., 2H), 1.52-1.41 (m, 3H), 1.15-1.08 (m, 3H). Analytical HPLC (Method A) RT=7.79 min, purity=95%; Factor XIa Ki=2.0 nM, Plasma Kallikrein Ki=179 nM.

Example 13. Preparation of (3R,7S)-7-(4-(5-Chloro-2-(4-chloro-1H-1,2,3-triazol-1-yl)phenyl)-6-oxopyrimidin-1(6H)-yl)-3-methyl-4,5,6,7,9,10-hexahydrobenzo[b][1,5]diazacyclo-dodecine-2,8(1H,3H)-dione

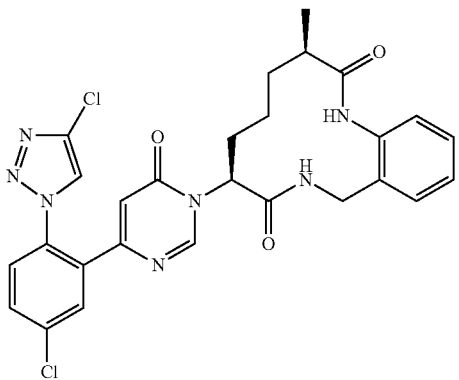 [SMILES: C[C@@H]1CCC[C@H](n2cnc(-c3cc(Cl)ccc3-n3cc(Cl)nn3)cc2=O)C(=O)NCc2ccccc2NC1=O]

(3R,7S)-7-(4-(5-Chloro-2-(4-chloro-1H-1,2,3-triazol-1-yl)phenyl)-6-oxopyrimidin-1(6H)-yl)-3-methyl-4,5,6,7,9,10-hexahydrobenzo[b][1,5]diazacyclo-dodecine-2,8(1H,3H)-dione (0.008 g, 18.5% yield) was prepared in a similar manner as the procedure described in Example 11, by replacing 6-(5-chloro-2-(4-(trifluoromethyl)-1H-1,2,3-triazol-1-yl)phenyl)pyrimidin-4-ol with 6-[5-chloro-2-(4-chloro-1H-1,2,3-triazol-1-yl)phenyl] pyrimidin-4-ol, prepared as described in Intermediate 2. (ESI) m/z: 584 (M+H)$^+$. $^1$H NMR (400 MHz, DMSO-d6) δ 8.79 (s, 1H), 8.70 (s, 2H), 8.50 (s, 1H), 7.85 (d, J=2.2 Hz, 1H), 7.77-7.73 (m, 1H), 7.69-7.65 (m, 1H), 7.39 (d, J=7.7 Hz, 1H), 7.29-7.23 (m, 2H), 7.11-7.03 (m, 1H), 6.18 (s, 1H), 5.25-5.19 (m, 1H), 4.98 (dd, J=14.5, 6.4 Hz, 1H), 3.78 (d, J=14.3 Hz, 1H), 2.29-2.22 (m, 1H), 1.75 (br. s., 2H), 1.51-1.40 (m, 4H), 1.11 (d, J=7.0 Hz, 3H). Analytical HPLC (Method X) RT=5.79 min, purity=95%; Factor XIa Ki=8.5 nM, Plasma Kallikrein Ki=1,230 nM.

Example 14. Preparation of (3R,7S)-7-(4-(3-Chloro-2-fluoro-6-(4-(trifluoromethyl)-1H-1,2,3-triazol-1-yl)phenyl)-6-oxopyrimidin-1(6H)-yl)-3-methyl-4,5,6,7,9,10-hexahydrobenzo[b][1,5]-diazacyclododecine-2,8(1H,3H)-dione

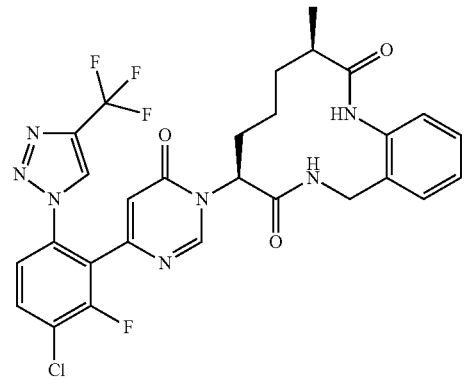 [SMILES: C[C@@H]1CCC[C@H](n2cnc(-c3c(-n4cc(C(F)(F)F)nn4)ccc(Cl)c3F)cc2=O)C(=O)NCc2ccccc2NC1=O]

(3R,7S)-7-(4-(3-Chloro-2-fluoro-6-(4-(trifluoromethyl)-1H-1,2,3-triazol-1-yl)phenyl)-6-oxopyrimidin-1(6H)-yl)-3-methyl-4,5,6,7,9,10-hexahydrobenzo[b][1,5]-diazacyclododecine-2,8(1H,3H)-dione (0.0042 g, 8.9% yield) was prepared in a similar manner as the procedure described in Example 11, by replacing 6-(5-chloro-2-(4-(trifluoromethyl)-1H-1,2,3-triazol-1-yl)phenyl)pyrimidin-4-ol with 6-(3-chloro-2-fluoro-6-(4-(trifluoromethyl)-1H-1,2,3-triazol-1-yl)phenyl)pyrimidin-4-ol, prepared as described in Intermediate 4. (ESI) m/z: 618 (M+H)$^+$. $^1$H NMR (400 MHz, DMSO-d6) δ 9.17 (d, J=0.7 Hz, 1H), 8.80 (s, 1H), 8.70 (d, J=6.4 Hz, 1H), 8.47 (s, 1H), 7.98 (dd, J=8.6, 7.9 Hz, 1H), 7.69 (dd, J=8.7, 1.4 Hz, 1H), 7.39 (d, J=7.7 Hz, 1H), 7.29-7.22 (m, 2H), 7.12-7.03 (m, 1H), 6.54 (s, 1H), 5.23 (t, J=8.6 Hz, 1H), 4.99 (dd, J=14.4, 6.7 Hz, 1H), 3.77 (d, J=14.3 Hz, 1H), 2.26-2.23 (m, 1H), 1.79-1.71 (m, 2H), 1.52-1.38 (m, 4H), 1.11 (d, J=7.0 Hz, 3H). Analytical HPLC (Method A) RT=8.5 min, purity=95%; Factor XIa Ki=4.3 nM, Plasma Kallikrein Ki=733 nM.

Example 15. Preparation of (3R,7S)-7-(4-(5-Chloro-2-(4-(difluoromethyl)-1H-1,2,3-triazol-1-yl)phenyl)-6-oxopyrimidin-1(6H)-yl)-3-methyl-4,5,6,7,9,10-hexahydrobenzo[b][1,5]diazacyclo-dodecine-2,8(1H,3H)-dione

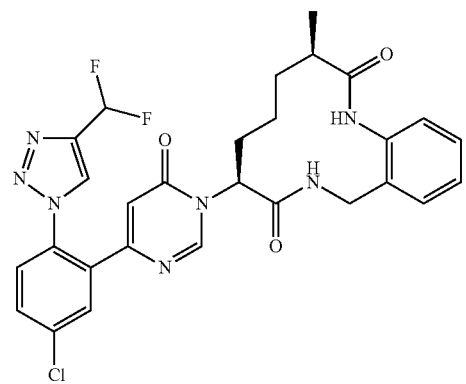 [SMILES: C[C@@H]1CCC[C@H](n2cnc(-c3cc(Cl)ccc3-n3cc(C(F)F)nn3)cc2=O)C(=O)NCc2ccccc2NC1=O]

(3R,7S)-7-(4-(5-Chloro-2-(4-(difluoromethyl)-1H-1,2,3-triazol-1-yl)phenyl)-6-oxopyrimidin-1(6H)-yl)-3-methyl-4,5,6,7,9,10-hexahydrobenzo[b][1,5]diazacyclo-dodecine-2,8(1H,3H)-dione (0.0076 g, 16.2% yield) was prepared in a similar manner as the procedure described in Example 11, by replacing 6-(5-chloro-2-(4-(trifluoromethyl)-1H-1,2,3-triazol-1-yl)phenyl)pyrimidin-4-ol with 6-(5-chloro-2-(4-(difluoromethyl)-1H-1,2,3-triazol-1-yl)phenyl)pyrimidin-4-ol prepared as described in Intermediate 6. (ESI) m/z: 582 (M+H)+. 1H NMR (400 MHz, DMSO-d6) δ 8.90-8.84 (m, 2H), 8.78 (d, J=6.6 Hz, 1H), 8.56 (s, 1H), 7.94 (d, J=2.2 Hz, 1H), 7.86-7.82 (m, 1H), 7.80-7.74 (m, 1H), 7.47 (d, J=7.3 Hz, 1H), 7.43-7.28 (m, 3H), 7.17-7.13 (m, 1H), 6.24 (s, 1H), 5.30 (t, J=8.6 Hz, 1H), 5.06 (dd, J=14.2, 6.9 Hz, 1H), 3.85 (d, J=14.5 Hz, 1H), 1.83 (br. s., 2H), 1.53 (d, J=7.7 Hz, 3H), 1.25 (s, 2H), 1.22-1.15 (m, 3H). Analytical HPLC (Method A) RT=7.6 min, purity=90%; Factor XIa Ki=34.8 nM, Plasma Kallikrein Ki=3,360 nM.

Example 16. Preparation of (3R,7S)-7-(4-(5-Chloro-2-(4-chloro-H-1,2,3-triazol-1-yl)phenyl)-2-oxo-5,6-dihydropyridin-1(2H)-yl)-3-methyl-4,5,6,7,9,10-hexahydrobenzo[b][1,5]diazacyclododecine-2,8(1H,3H)-dione

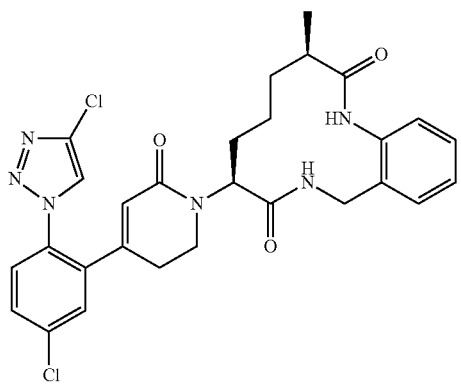 [SMILES: C[C@@H]1CCC[C@H](N2CCC(c3cc(Cl)ccc3-n3cc(Cl)nn3)=CC2=O)C(=O)NCc2ccccc2NC1=O]

16A. Preparation of Diethyl (2-((3-(5-chloro-2-(4-chloro-1H-1,2,3-triazol-1-yl)phenyl)-3-oxopropyl)((3R,7S)-3-methyl-2,8-dioxo-1,2,3,4,5,6,7,8,9,10-decahydrobenzo[b][1,5]diazacyclodo-decin-7-yl) amino)-2-oxoethyl)phosphonate To a round bottom flask was added (3R,7S)-7-amino-3-methyl-4,5,6,7,9,10-hexahydrobenzo[b][1,5]diazacyclododecine-2,8(1H,3H)-dione hydrochloride (0.030 g, 0.096 mmol), DCM (3.32 ml), DIEA (0.118 ml, 0.673 mmol) and 1-(5-chloro-2-(4-chloro-1H-1,2,3-triazol-1-yl)phenyl)prop-2-en-1-one (0.026 g, 0.096 mmol). The reaction was stirred at rt for 1 h. The reaction was then cooled to 0° C., then pyridine (0.039 ml, 0.481 mmol) and 2-(diethoxyphosphoryl)acetic acid (0.057 g, 0.289 mmol) were added, respectively. Afterwards, POCl₃ (0.018 ml, 0.192 mmol) was added dropwise and the complete mixture stirred at 0° C. After 30 min, the reaction was diluted with DCM (15 ml) and washed with sat NaHCO₃ (10 ml). The organic layer was separated, washed with water (10 ml) and brine (10 ml), dried over MgSO₄, filtered and concentrated. The residue was purified by normal phase chromatography to give diethyl (2-((3-(5-chloro-2-(4-chloro-1H-1,2,3-triazol-1-yl)phenyl)-3-oxopropyl)((3R,7R)-3-meth yl-2,8-dioxo-1,2,3,4,5,6,7,8,9,10-decahydrobenzo[b][1,5]diazacyclododecin-7-yl)amino)-2-oxoethyl)phosphonate (0.0538 g, 0.075 mmol, 77% yield) as a light brown film. (ESI) m/z: 721.4 (M+H)+.

16B. Preparation of (3R,7S)-7-(4-(5-Chloro-2-(4-chloro-1H-1,2,3-triazol-1-yl)phenyl)-2-oxo-5,6-dihydropyridin-1(2H)-yl)-3-methyl-4,5,6,7,9,10-hexahydrobenzo[b][1,5]diazacyclododecine-2,8(1H,3H)-dione To a solution of diethyl (2-((3-(5-chloro-2-(4-chloro-1H-1,2,3-triazol-1-yl)phenyl)-3-oxopropyl)((3R,7S)-3-methyl-2,8-dioxo-1,2,3,4,5,6,7,8,9,10-decahydrobenzo[b][1,5]diazacyclododecin-7-yl)amino)-2-oxoethyl)phosphonate (53.8 mg, 0.075 mmol) in MeOH (2.0 ml) was added 0.5 M NaOMe in MeOH (0.085 ml, 0.373 mmol) at rt. After 1 h, the reaction quenched with 1.0 N HCl (aq) (0.5 ml). The reaction mixture was concentrated and the residue purified by reverse phase chromatography to give (3R,7S)-7-(4-(5-chloro-2-(4-chloro-1H-1,2,3-triazol-1-yl)phenyl)-2-oxo-5,6-dihydropyridin-1(2H)-yl)-3-methyl-4,5,6,7,9,10-hexahydrobenzo[b][1,5]diazacyclododecine-2,8(1H,3H)-dione (15.7 mg, 35.3%) as a white solid. (ESI) m/z: 567.3 (M+H)+. 1H NMR (400 MHz, DMSO-d6) δ 8.77 (s, 1H), 8.68 (d, J=1.3 Hz, 1H), 8.26 (d, J=6.4 Hz, 1H), 7.70-7.59 (m, 3H), 7.39 (d, J=7.9 Hz, 1H), 7.26-7.19 (m, 2H), 7.09-7.02 (m, 1H), 5.55 (s, 1H), 4.87 (dd, J=14.2, 6.5 Hz, 1H), 4.77 (dd, J=11.3, 4.7 Hz, 1H), 3.83-3.71 (m, 2H), 2.27 (d, J=7.3 Hz, 1H), 2.14-2.02 (m, 2H), 1.65-1.56 (m, 1H), 1.48-1.40 (m, 3H), 1.35-1.25 (m, 2H), 1.11-1.02 (m, 3H). Analytical HPLC (Method A) RT=8.09 min, purity=95%; Factor XIa Ki=4.0 nM, Plasma Kallikrein Ki=60.7 nM.

Example 17. Preparation of (3R,7S)-7-(4-(3-Chloro-2,6-difluorophenyl)-2-oxo-56-dihydropyridin-1(2H)-yl)-3-methy 1-4,5,6,7,9,10-hexahydrobenzo[b][1,5]diazacyclododecine-2,8(1H,3H)-dione

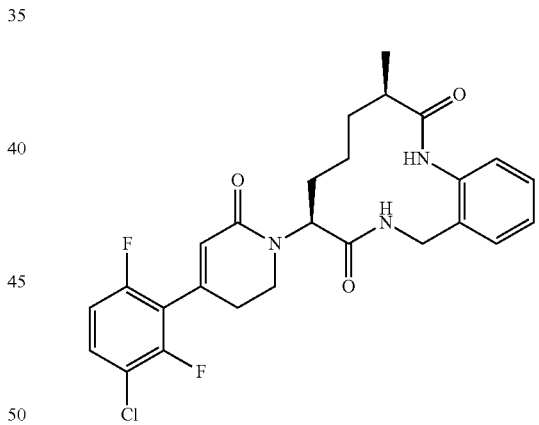

((3R,7S)-7-(4-(3-Chloro-2,6-difluorophenyl)-2-oxo-5,6-dihydropyridin-1(2H)-yl)-3-methyl-4,5,6,7,9,10-hexahydrobenzo[b][1,5]diazacyclododecine-2,8(1H,3H)-dione (0.0154 g, 41% yield) was prepared in a similar manner as the procedure described in Example 16, by replacing 1-(5-chloro-2-(4-chloro-1H-1,2,3-triazol-1-yl)phenyl)prop-2-en-1-one with 1-(3-chloro-2,6-difluorophenyl)prop-2-en-1-one, prepare as described in Intermediate 7. (ESI) m/z: 502 (M+H)+. 1H NMR (400 MHz, DMSO-d6) δ 8.71 (s, 1H), 8.31 (d, J=5.1 Hz, 1H), 7.62 (td, J=8.7, 5.7 Hz, 1H), 7.42 (d, J=7.5 Hz, 1H), 7.26-7.17 (m, 3H), 7.09-7.02 (m, 1H), 5.94 (s, 1H), 4.91-4.81 (m, 2H), 3.93 (dt, J=12.5, 6.2 Hz, 1H), 3.83 (d, J=13.6 Hz, 1H), 2.62-2.49 (m, 2H), 2.32-2.26 (m, 1H), 1.70-1.64 (m, 1H), 1.61-1.55 (m, 1H), 1.50-1.43 (m, 1H), 1.35 (d, J=4.8 Hz, 2H), 1.09 (d, J=7.0 Hz, 3H). Analytical HPLC (Method A) RT=8.48 min, purity=95%; Factor XIa Ki=112 nM, Plasma Kallikrein Ki=558 nM.

Example 18. Preparation of (3R,7S)-7-(4-(5-Chloro-2-(4-(trifluoromethyl)-1H-1,2,3-triazol-1-yl)phenyl)-2-oxo-5,6-dihydropyridin-1(2H)-yl)-3-methyl-4,5,6,7,9,10-hexahydrobenzo[b][1,5]diazacyclododecine-2,8(1H,3H)-dione

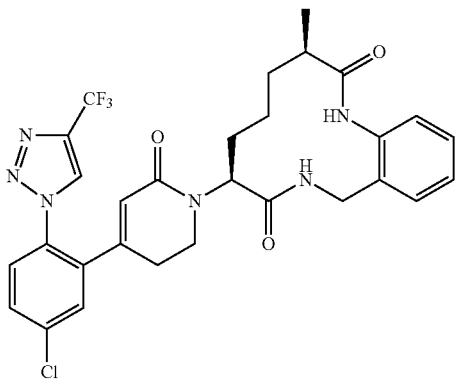 [SMILES: C[C@@H]1CCC[C@H](N2CCC(c3cc(Cl)ccc3-n3cc(C(F)(F)F)nn3)=CC2=O)C(=O)NCc2ccccc2NC1=O]

(3R,7S)-7-(4-(5-Chloro-2-(4-(trifluoromethyl)-1H-1,2,3-triazol-1-yl)phenyl)-2-oxo-5,6-dihydropyridin-1(2H)-yl)-3-methyl-4,5,6,7,9,10-hexahydrobenzo[b][1,5]diazacyclododecine-2,8(1H,3H)-dione (0.018 g, 39% yield) was prepared in a similar manner as the procedure described in Example 16, by replacing 1-(5-chloro-2-(4-chloro-1H-1,2,3-triazol-1-yl)phenyl)prop-2-en-1-one with 1-(5-chloro-2-(4-(trifluoromethyl)-1H-1,2,3-triazol-1-yl)phenyl)prop-2-en-1-one, prepare as described in Intermediate 5. (ESI) m/z: 601 (M+H)$^+$. $^1$H NMR (400 MHz, DMSO-d6) δ 9.27 (d, J=0.9 Hz, 1H), 8.68 (s, 1H), 8.26 (d, J=6.2 Hz, 1H), 7.72-7.68 (m, 3H), 7.39 (d, J=7.7 Hz, 1H), 7.25-7.18 (m, 2H), 7.08-7.02 (m, 1H), 5.51 (s, 1H), 4.87 (dd, J=14.4, 6.7 Hz, 1H), 4.76 (dd, J=11.3, 4.7 Hz, 1H), 3.81-3.72 (m, 2H), 3.33-3.26 (m, 1H), 2.30-2.24 (m, 1H), 2.16-2.05 (m, 2H), 1.62-1.55 (m, 1H), 1.48-1.41 (m, 2H), 1.34-1.26 (m, 2H), 1.07 (d, J=7.0 Hz, 3H). Analytical HPLC (Method A) RT=8.73 min, purity=94%; Factor XIa Ki=3.1 nM, Plasma Kallikrein Ki=103 nM.

Example 18. Preparation of (3R,7S)-7-(4-(5-Chloro-2-(4-chloro-H-1,2,3-triazol-1-yl)phenyl)-2-oxopyridin-1(2H)-yl)-3-methyl-4,5,6,7,9,10-hexahydrobenzo[b][1,5]diazacyclododecine-2,8(1H,3H)-dione

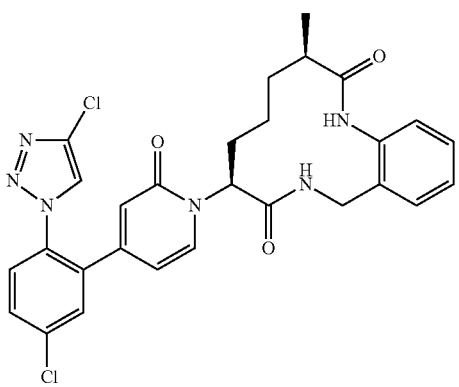 [SMILES: C[C@@H]1CCC[C@H](n2ccc(-c3cc(Cl)ccc3-n3cc(Cl)nn3)cc2=O)C(=O)NCc2ccccc2NC1=O]

To a suspension of (3R,7S)-7-(4-(5-chloro-2-(4-chloro-1H-1,2,3-triazol-1-yl)phenyl)-2-oxo-5,6-dihydropyridin-1(2H)-yl)-3-methyl-4,5,6,7,9,10-hexahydrobenzo[b][1,5]diazacyclododecine-2,8(1H,3H)-dione in DMF (0.5 mL) was added K$_2$CO$_3$ (0.024 g, 0.176 mmol). Pearlman's Catalyst (2.475 mg, 0.018 mmol) and tert-butyl hydroperoxide (70% in water) (0.024 mL, 0.176 mmol) were then added, respectively and the resulting reaction mixture was stirred at rt. An additional equivalent of Pearlman's Catalyst and tert-butyl hydroperoxide were added in two successive days. After 30 days, the crude reaction mixture was purified by reverse phase chromatography and lyopholized to give the desired product (0.0015 g, 13.6%) as a light yellow solid. (ESI) m/z: 565.3 (M+H)$^+$. 1H NMR (500 MHz, DMSO-d6) δ 8.77 (s, 1H), 8.66-8.59 (m, 2H), 7.84 (d, J=7.2 Hz, 1H), 7.73-7.69 (m, 2H), 7.67-7.65 (m, 1H), 7.38 (d, J=7.2 Hz, 1H), 7.27-7.22 (m, 2H), 7.08-7.04 (m, 1H), 6.08 (d, J=1.9 Hz, 1H), 5.83 (dd, J=7.2, 2.2 Hz, 1H), 5.31-5.25 (m, 1H), 4.96 (dd, J=14.3, 6.9 Hz, 1H), 3.76 (d, J=14.3 Hz, 1H), 2.29 (dd, J=3.9, 1.9 Hz, 1H), 1.65 (d, J=5.2 Hz, 2H), 1.50-1.45 (m, 2H), 1.10 (d, J=7.2 Hz, 3H). Analytical HPLC (Method A) RT=7.90 min, purity=90%; Factor XIa Ki=10.1 nM, Plasma Kallikrein Ki=259 nM.

Example 19. Preparation of (3R,7S)-7-(4-(5-Chloro-2-(4-(trifluoromethyl)-1H-1,2,3-triazol-1-yl)phenyl)-6-oxopyrimidin-1(6H)-yl)-12-fluoro-3-methyl-4,5,6,7,9,10-hexahydrobenzo[b][1,5]diazacyclododecine-2,8(1H,3H)-dione

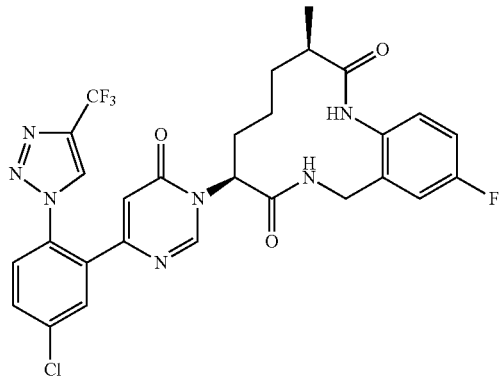 [SMILES: C[C@@H]1CCC[C@H](n2cnc(-c3cc(Cl)ccc3-n3cc(C(F)(F)F)nn3)cc2=O)C(=O)NCc2cc(F)ccc2NC1=O]

(3R,7S)-7-(4-(5-Chloro-2-(4-(trifluoromethyl)-1H-1,2,3-triazol-1-yl)phenyl)-6-oxopyrimidin-1(6H)-yl)-12-fluoro-3-methyl-4,5,6,7,9,10-hexahydrobenzo[b][1,5]diazacyclododecine-2,8(1H,3H)-dione was prepared in a similar manner as the procedure described in Example 11, by replacing (3R,7S)-7-amino-3-methyl-4,5,6,7,9,10-hexahydrobenzo[b][1,5]-diazacyclododecine-2,8(1H,3H)-dione with (3R,7S)-7-amino-12-fluoro-3-methyl-4,5,6,7,9,10-hexahydrobenzo[b][1,5]diazacyclododecine-2,8(1H,3H)-dione, prepare as described in Intermediate 10. (ESI) m/z: 618.3 (M+H)$^+$. $^1$H NMR (400 MHz, DMSO-d6) δ 9.20 (s, 1H), 8.84 (s, 1H), 8.75 (d, J=6.2 Hz, 1H), 8.43 (s, 1H), 7.88 (d, J=2.2 Hz, 1H), 7.82-7.73 (m, 2H), 7.36 (dd, J=8.8, 5.5 Hz, 1H), 7.19 (dd, J=9.5, 3.1 Hz, 1H), 7.09 (td, J=8.6, 3.1 Hz, 1H), 6.30 (s, 1H), 5.20 (t, J=8.5 Hz, 1H), 4.96 (dd, J=14.5, 6.6 Hz, 1H), 3.77 (d, J=13.9 Hz, 1H), 3.23 (s, 2H), 1.79-1.70 (m, 2H), 1.49-1.40 (m, 3H), 1.11 (d, J=7.0 Hz, 3H). Analytical HPLC (Method A) RT=8.28 min, purity=95%; Factor XIa Ki=18.7 nM, Plasma Kallikrein Ki=13,000 nM.

Example 20. Preparation of (3R,7S)-7-(4-(5-Chloro-2-(4-(trifluoromethyl)-1H-1,2,3-triazol-1-yl)phenyl)-2-oxo-5,6-dihydropyridin-1(2H)-yl)-12-fluoro-3-methyl-4,5,6,7,9,10-hexahydrobenzo[b][1,5]diazacyclododecine-2,8(1H,3H)-dione

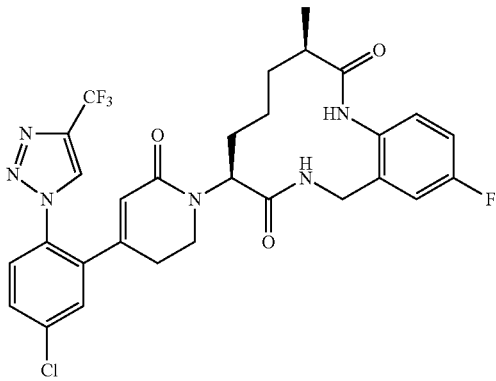 [SMILES: C[C@@H]1CCC[C@H](N2CCC(c3cc(Cl)ccc3-n3cc(C(F)(F)F)nn3)=CC2=O)C(=O)NCc2cc(F)ccc2NC1=O]

(3R,7S)-7-(4-(5-Chloro-2-(4-(trifluoromethyl)-1H-1,2,3-triazol-1-yl)phenyl)-2-oxo-5,6-dihydropyridin-1(2H)-yl)-12-fluoro-3-methyl-4,5,6,7,9,10-hexahydrobenzo[b][1,5]diazacyclododecine-2,8(1H,3H)-dione was prepared in a similar manner as the procedure described in Example 18, by replacing (3R,7S)-7-amino-3-methyl-4,5,6,7,9,10-hexahydrobenzo[b][1,5]-diazacyclododecine-2,8(1H,3H)-dione with (3R,7S)-7-amino-12-fluoro-3-methyl-4,5,6,7,9,10-hexahydrobenzo[b][1,5]diazacyclododecine-2,8(1H,3H)-dione, prepare as described in Intermediate 10. (ESI) m/z: 619.3 (M+H)⁺. ¹H NMR (400 MHz, DMSO-d6) δ 9.27 (s, 1H), 8.72 (s, 1H), 8.31 (d, J=6.4 Hz, 1H), 7.73-7.65 (m, 3H), 7.36 (dd, J=8.9, 5.6 Hz, 1H), 7.14 (dd, J=9.5, 2.9 Hz, 1H), 7.07-7.01 (m, 1H), 5.51 (s, 1H), 4.86 (dd, J=14.9, 6.7 Hz, 1H), 4.78-4.70 (m, 1H), 3.79-3.75 (m, 1H), 2.30-2.24 (m, 1H), 2.16-2.07 (m, 2H), 1.62-1.57 (m, 1H), 1.45-1.39 (m, 3H), 1.36-1.31 (m, 1H), 1.28-1.22 (m, 1H), 1.07 (d, J=7.0 Hz, 3H), 0.78 (d, J=7.3 Hz, 1H). Analytical HPLC (Method A) RT=8.44 min, purity=95%; Factor XIa Ki=7.0 nM, Plasma Kallikrein Ki=268 nM.

Example 21. Preparation of (3R,7S)-7-(4-(5-chloro-2-(4-(trifluoromethyl)-1H-1,2,3-triazol-1-yl)phenyl)-6-oxo-3,6-dihydropyridin-1(2H)-yl)-3,10-dimethyl-4,5,6,7,9,10-hexahydrobenzo[b][1,5]diazacyclododecine-2,8(1H,3H)-dione (diastereomer A)

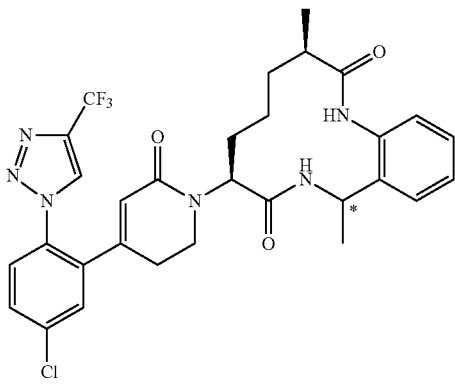

diastereomer A

21A. Preparation of (E)-1-(2-Nitrophenyl)ethanone O-methyl oxime

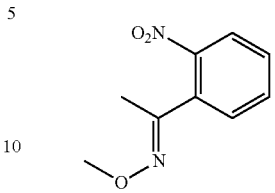

To a solution of 1-(2-nitrophenyl)ethanone (2.0 g, 12.11 mmol) and O-methylhydroxylamine hydrochloride (1.011 g, 12.11 mmol) in pyridine (40 ml)/EtOH (40 ml) was added molecular sieves (~1 g). The mixture was heated to reflux overnight. The reaction mixture was filtered through a plug of Celite® and filtrate concentrated to give (E)-1-(2-nitrophenyl)ethanone O-methyl oxime as an oil which slowly solidified. The material carried forward to the next reaction without further purification. (ESI) m/z: 195.1 (M+H)⁺.

21B. Preparation of 1-(2-Nitrophenyl)ethanamine

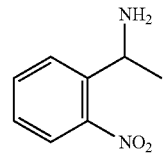

A solution of (E)-1-(2-nitrophenyl)ethanone O-methyl oxime (2.2 g, 11.33 mmol) in THF (10 ml) was cooled to 0° C., to this was added borane-THF complex (34.0 ml, 34.0 mmol) and the resulting solution was then heated at reflux for 6 h. The reaction was cooled to −20° C. and water (3 ml) was added slowly followed by aq. 20% KOH solution (3 ml) over 20 min. The resulting mixture was then heated at reflux for a further 2 h and then poured into DCM. The separated organics were washed with brine, and dried over MgSO₄, filtered, and concentrated. The resulting oil was used immediately in subsequent reaction without further purification. (ESI) m/z: 167.3 (M+H)⁺.

21C. Preparation of tert-Butyl ((2 S)-1-((1-(2-nitrophenyl)ethyl)amino)-1-oxopent-4-en-2-yl)carbamate

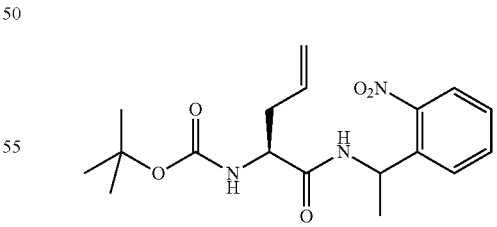

4-Methylmorpholine (2.49 ml, 22.63 mmol) was added to a stirring solution of commercially available (S)-2-((tert-butoxycarbonyl)amino)pent-4-enoic acid (2.44 g, 11.31 mmol), 1-(2-nitrophenyl)ethanamine (1.88 g, 11.31 mmol), and HATU (6.45 g, 16.97 mmol) in DMF (45.3 ml) at rt. After 14 h, the reaction mixture was partition between EtOAc and water. The organic layer was washed with brine, dried over Na₂SO₄, filtered, and concentrated. The crude material was purified by normal phase chromatography to give tert-butyl ((2S)-1-((1-(2-nitrophenyl)ethyl)amino)-1-oxopent-4-en-2-yl)carbamate (4.0 g, 97%). (ESI) m/z: 364.4 (M+H)+.

21D. Preparation of tert-Butyl ((2S)-1-((1-(2-aminophenyl)ethyl)amino)-1-oxopent-4-en-2-yl)carbamate

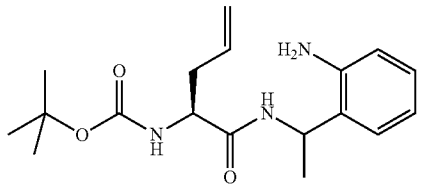 [SMILES: C=CC[C@H](NC(=O)OC(C)(C)C)C(=O)NC(C)c1ccccc1[N+](=O)[O-]]

tert-Butyl ((2S)-1-((1-(2-nitrophenyl)ethyl)amino)-1-oxopent-4-en-2-yl)carbamate (4.0 g, 11.01 mmol) was dissolved in acetone (78 ml) and H₂O (15.55 ml), cooled to 0° C., and zinc (7.20 g, 110 mmol) and NH₄Cl (2.94 g, 55.0 mmol) were added. The solution was allowed to gradually come to rt. After 14 h, the reaction was filtered through a pad of Celite® and filtrate concentrated. The residue was partitioned with H₂O (50 ml) and EtOAc (100 ml). The aqueous layer was extracted with EtOAc (2×50 mL). The combined organic layer was washed with brine (50 ml), dried (MgSO₄), filtered, and concentrated to give tert-butyl ((2S)-1-((1-(2-aminophenyl)ethyl)amino)-1-oxopent-4-en-2-yl)carbamate as a pinkish oil. This material was carried forward as is. (ESI) m/z: 334 (M+H)+.

21E. Preparation of tert-Butyl ((2S)-1-((1-(2-((R)-2-methylbut-3-enamido)phenyl)-ethyl)amino)-1-oxopent-4-en-2-yl)carbamate

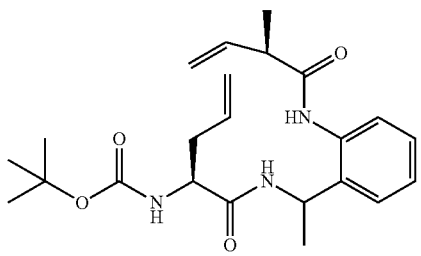 [SMILES: C=CC[C@H](NC(=O)OC(C)(C)C)C(=O)NC(C)c1ccccc1NC(=O)[C@H](C)C=C]

To a solution of (R)-2-methylbut-3-enoic acid (1.32 g, 13.21 mmol), tert-butyl ((2S)-1-((1-(2-aminophenyl)ethyl)amino)-1-oxopent-4-en-2-yl)carbamate (3.67 g, 11.01 mmol), pyridine (2.23 ml, 27.5 mmol) in EtOAc (117 ml) at 0° C. was added T3P (50% wt in EtOAc) (13.10 ml, 22.01 mmol). After stirring at rt for 14 h, the reaction was quenched with 1.5 M potassium phosphate and extracted with EtOAc (2×). The organic layer was washed with brine, dried over Na₂SO₄, filtered, and concentrated. The crude material was purified by normal phase chromatography to give the desired product (2.05 g, 45%) as a white foam. (ESI) m/z: 416 (M+H)+. ¹H NMR (400 MHz, DMSO-d6) δ 9.56 (d, J=9.7 Hz, 1H), 8.34 (d, J=7.7 Hz, 1H), 7.49 (d, J=7.7 Hz, 1H), 7.42-7.35 (m, 1H), 7.21 (dtd, J=5.6, 3.9, 2.0 Hz, 1H), 7.16-7.12 (m, 1H), 6.77 (t, J=7.2 Hz, 1H), 6.01-5.93 (m, 1H), 5.72-5.61 (m, 1H), 5.26-5.18 (m, 1H), 5.12-5.07 (m, 2H), 5.03-4.98 (m, 1H), 4.90 (d, J=10.1 Hz, 1H), 3.99-3.93 (m, 1H), 3.36-3.28 (m, 1H), 2.36-2.22 (m, 2H), 1.41-1.31 (m, 12H), 1.22 (dd, J=6.8, 4.4 Hz, 3H).

21F. Preparation of tert-Butyl ((3R,7S,E)-3,10-dimethyl-2,8-dioxo-1,2,3,6,7,8,9,10-octahydrobenzo[b][1,5]diazacyclododecin-7-yl)carbamate (diastereomeric mixture)

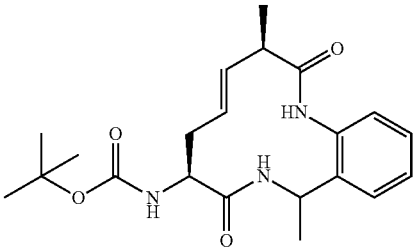 [SMILES: CC1NC(=O)[C@@H](NC(=O)OC(C)(C)C)C/C=C/[C@@H](C)C(=O)Nc2ccccc21]

tert-Butyl ((2 S)-1-((1-(2-((R)-2-methylbut-3-enamido)phenyl)ethyl)amino)-1-oxopent-4-en-2-yl)carbamate (2.0 g, 4.81 mmol) was added to EtOAc (600 ml) and degassed with a stream of argon for 30 min. Grubbs II (1.64 g, 1.93 mmol) was added and the mixture heated at 60° C. overnight. The crude material was washed with 1.5 M potassium phosphate solution, brine, dried over sodium sulfate, filtered, and concentrated. (ESI) m/z: 388 (M+H)+.

21G. Preparation of tert-Butyl ((3R,7S,E)-3,10-dimethyl-2,8-dioxo-1,2,3,6,7,8,9,10-octahydrobenzo[b][1,5]diazacyclododecin-7-yl)carbamate (diastereomer A)

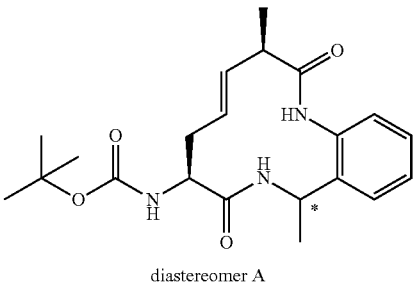 [SMILES: CC1NC(=O)[C@@H](NC(=O)OC(C)(C)C)C/C=C/[C@@H](C)C(=O)Nc2ccccc21]

diastereomer A tert-Butyl ((3R,7S,E)-3,10-dimethyl-2,8-dioxo-1,2,3,6,7,8,9,10-octahydrobenzo[b][1,5]-diazacyclododecin-7-yl)carbamate (diastereomeric mixture) (0.600 g, 0.619 mmol) was dissolved in DMF and purified by reverse phase chromatography to give tert-butyl ((3R,7S,E)-3,10-dimethyl-2,8-dioxo-1,2,3,6,7,8,9,10-octahydrobenzo[b][1,5]diazacyclododecin-7-yl)carbamate (diastereomer A) (0.082 g, 34% yield) as the early eluting isomer (more polar peak). (ESI) m/z: 388 (M+H)+. ¹H NMR (400 MHz, CD₃OD) δ 7.73 (d, J=7.5 Hz, 1H), 7.51 (d, J=7.5 Hz, 1H), 7.40-7.36 (m, 2H), 7.28-7.24 (m, 1H), 6.06-6.00 (m, 1H), 5.85-5.80 (m, 1H), 5.09-5.04 (m, 1H), 3.23-3.19 (m, 1H), 2.72-2.67 (m, 1H), 2.40-2.34 (m, 2H), 1.61-1.58 (m, 3H), 1.44 (s, 9H), 1.33 (d, J=7.3 Hz, 3H)

21H. Preparation of tert-Butyl ((3R,7S,E)-3,10-dimethyl-2,8-dioxo-1,2,3,6,7,8,9,10-octahydrobenzo[b][1,5]diazacyclododecin-7-yl)carbamate (diastereomer B)

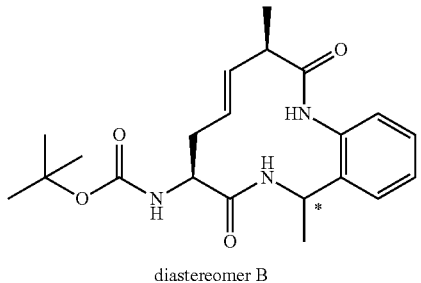 [SMILES: CC1NC(=O)[C@@H](NC(=O)OC(C)(C)C)C/C=C/[C@@H](C)C(=O)Nc2ccccc21]

diastereomer B tert-Butyl ((3R,7S,E)-3,10-dimethyl-2,8-dioxo-1,2,3,6,7,8,9,10-octahydrobenzo[b][1,5]-diazacyclododecin-7-yl)carbamate (diastereomeric mixture) purified by reverse phase chromatography in 21G to gave tert-butyl ((3R,7S,E)-3,10-dimethyl-2,8-dioxo-1,2,3,6,7,8,9,10-octahydrobenzo[b][1,5]-diazacyclododecin-7-yl)carbamate (diastereomer B) (0.078 g, 33% yield) as the late eluting isomer (less polar peak). (ESI) m/z: 388 (M+H)$^+$. $^1$H NMR (400 MHz, CD$_3$OD) δ 7.56-7.44 (m, 2H), 7.37-7.19 (m, 3H), 6.06-5.94 (m, 1H), 5.67-5.60 (m, 1H), 5.04-4.97 (m, 1H), 3.26-3.19 (m, 1H), 2.46-2.36 (m, 2H), 1.65-1.55 (m, 3H), 1.46 (s, 9H), 1.38-1.31 (m, 3H).

21I. Preparation of (3R,7S)-7-Amino-3,10-dimethyl-4,5,6,7,9,10-hexahydrobenzo[b][1,5]-diazacyclododecine-2,8(1H,3H)-dione (diastereomer A)

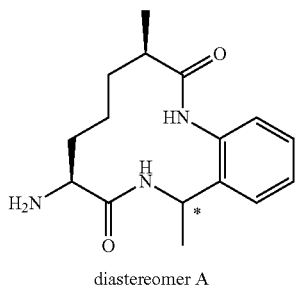 [SMILES: CC1NC(=O)[C@@H](N)CCC[C@@H](C)C(=O)Nc2ccccc21]

diastereomer A

PtO$_2$ (9.61 mg, 0.042 mmol) was added to a stirring solution of tert-butyl ((3R,7S,E)-3,10-dimethyl-2,8-dioxo-1,2,3,6,7,8,9,10-octahydrobenzo[b][1,5]diazacyclododecin-7-yl)carbamate (0.082 g, 0.212 mmol) in EtOH (10 ml) and subjected to a H$_2$ atmosphere (55 psi). After 5 h, the catalyst was filtered off through a plug of Celite® and the filtrate concentrated. The residue was dissolved in MeOH (5 ml) and treated with HCl (4.0 M in dioxane) (0.529 ml, 2.116 mmol). After stirring overnight, the reaction mixture was concentrated to dryness. The residue was dissolved in MeOH, passed through a NaHCO$_3$ resin cartridge (StratoSpheres® SPE, 500 mg), and filtrate concentrated. The free based residue was carried forward to the next reaction without further purification. (ESI) m/z: 290 (M+H)$^+$.

21J. Preparation of Diethyl (2-((3-(5-chloro-2-(4-(trifluoromethyl)-1H-1,2,3-triazol-1-yl)phenyl)-3-oxopropyl)((3R,7S)-3,10-dimethyl-2,8-dioxo-1,2,3,4,5,6,7,8,9,10-decahydrobenzo[b][1,5]diazacyclododecin-7-yl)amino)-2-oxoethyl) phosphonate

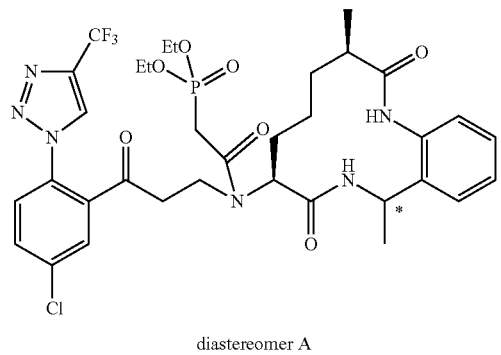 [SMILES: CCOP(=O)(CC(=O)N(CCC(=O)c1cc(Cl)ccc1-n1cc(C(F)(F)F)nn1)[C@H]1CCC[C@@H](C)C(=O)Nc2ccccc2C(C)NC1=O)OCC]

diastereomer A

To (3R,7S)-7-amino-3,10-dimethyl-4,5,6,7,9,10-hexahydrobenzo[b][1,5]diazacyclododecine-2,8(1H,3H)-dione (diastereomer A) (0.025 g, 0.086 mmol) in DCM (1.25 ml), cooled to –20° C., was added DIEA (0.106 ml, 0.605 mmol), then 1-(5-chloro-2-(4-(trifluoromethyl)-1H-1,2,3-triazol-1-yl)phenyl)prop-2-en-1-one (0.026 g, 0.086 mmol) in DCM (0.5 ml) was slowly added. After 1 h, 2-(diethoxyphosphoryl)acetic acid (0.051 g, 0.259 mmol), pyridine (0.056 ml, 0.691 mmol) and a DCM solution of POCl$_3$ (8.05 µl, 0.086 mmol) were added, respectively. After 30 min, the reaction was quenched with water (5 ml) and extracted with DCM (3×10 ml). The combined organic layers were washed with brine and dried (MgSO$_4$), filtered and concentrated. (ESI) m/z: 769 (M+H)$^+$.

21k. Preparation of (3R,7S)-7-(4-(5-Chloro-2-(4-(trifluoromethyl)-1H-1,2,3-triazol-1-yl)phenyl)-2-oxo-5,6-dihydropyridin-1(2H)-yl)-3,10-dimethyl-4,5,6,7,9,10-hexahydrobenzo[b][1,5]diazacyclododecine-2,8(1H,3H)-dione (diastereomer A)

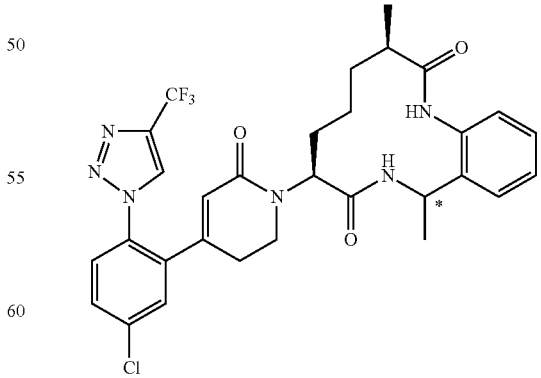

diastereomer A

To diethyl (2-((3-(5-chloro-2-(4-(trifluoromethyl)-1H-1,2,3-triazol-1-yl)phenyl)-3-oxopropyl)((3R,7S)-3,10-dimethyl-2,8-dioxo-1,2,3,4,5,6,7,8,9,10-decahydro benzo[b][1,5]diazacyclo-dodecin-7-yl)amino)-2-oxoethyl)phosphonate (diastereomer A)(0.066 g, 0.086 mmol) in MeOH (50 ml), cooled to 0° C., was added excess NaOMe (0.074 g, 0.343 mmol). After 30 min, the reaction mixture was quenched with 1.0 N HCl solution (0.2 ml) and concentrated. The residue was purified by reverse phase chromatography and freeze-dried to give the desired product (4 mg, 7.2%) as a white solid. (ESI) m/z: 615.3 (M+H)+. $^1$H NMR (400 MHz, CD$_3$OD) δ 8.89-8.82 (m, 1H), 7.58-7.41 (m, 4H), 7.30-7.15 (m, 3H), 5.61-5.53 (m, 1H), 5.16 (dt, J=13.6, 7.0 Hz, 1H), 3.97-3.86 (m, 1H), 3.46-3.38 (m, 1H), 2.70-2.60 (m, 1H), 2.44-2.28 (m, 2H), 2.22-2.13 (m, 1H), 2.05 (dt, J=17.4, 5.3 Hz, 1H), 1.80-1.68 (m, 2H), 1.62-1.48 (m, 3H), 1.46-1.41 (m, 3H), 1.15-1.06 (m, 3H). Analytical HPLC (Method A) RT=9.14 min, purity=95%; Factor XIa Ki=93 nM, Plasma Kallikrein Ki=2,830 nM.

Example 22. Preparation of (3R,7S)-7-(4-(5-Chloro-2-(4-(trifluoromethyl)-1H-1,2,3-triazol-1-yl)phenyl)-2-oxo-5,6-dihydropyridin-1(2H)-yl)-3,10-dimethyl-4,5,6,7,9,10-hexahydrobenzo[b][1,5]diazacyclododecine-2,8(1H,3H)-dione (diastereomer B)

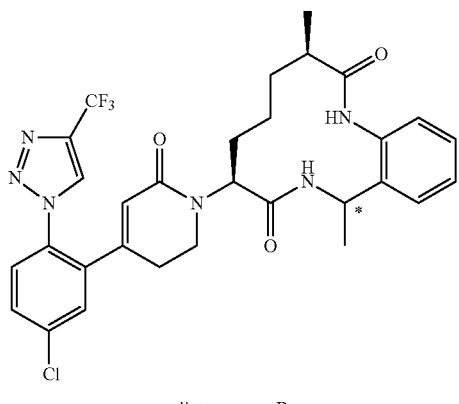

diastereomer B

Preparation of (3R,7S)-7-(4-(5-chloro-2-(4-(trifluoromethyl)-1H-1,2,3-triazol-1-yl)phenyl)-2-oxo-5,6-dihydropyridin-1(2H)-yl)-3,10-dimethyl-4,5,6,7,9,10-hexahydrobenzo[b][1,5]diazacyclo-dodecine-2,8(1H,3H)-dione (diastereomer B) (4 mg, 7.2%) was prepared in a similar manner as the procedure described in Example 21, by replacing tert-butyl ((3R,7S,E)-3,10-dimethyl-2,8-dioxo-1,2,3,6,7,8,9,10-octahydrobenzo[b][1,5]diazacyclododecin-7-yl)carbamate (diastereomer A) with tert-butyl ((3R,7S,E)-3,10-dimethyl-2,8-dioxo-1,2,3,6,7,8,9,10-octahydrobenzo[b][1,5]diazacyclododecin-7-yl)carbamate (diastereomer B). (ESI) m/z: 615.3 (M+H)+. $^1$H NMR (400 MHz, CD$_3$OD) δ 8.97 (s, 1H), 8.47 (d, J=7.3 Hz, 1H), 7.71-7.65 (m, 3H), 7.55 (t, J=8.5 Hz, 2H), 7.36 (t, J=7.0 Hz, 1H), 7.31-7.25 (m, 1H), 5.74 (s, 1H), 5.34 (t, J=6.7 Hz, 1H), 4.73 (dd, J=12.0, 4.3 Hz, 1H), 4.24-4.13 (m, 1H), 3.93-3.85 (m, 1H), 3.57-3.49 (m, 1H), 2.37 (td, J=7.3, 3.6 Hz, 1H), 2.30-2.24 (m, 2H), 1.91-1.82 (m, 1H), 1.75 (d, J=7.9 Hz, 1H), 1.70-1.62 (m, 2H), 1.60-1.55 (m, 4H), 1.33 (d, J=7.3 Hz, 3H). Analytical HPLC (Method A) RT=9.18 min, purity=95%; Factor XIa Ki=3,680 nM, Plasma Kallikrein Ki=>13,000 nM.

Example 23. Preparation of 1-(3-chloro-2-fluorophenyl)-N-((3R,7S)-3-methyl-2,8-dioxo-1,2,3,4,5,6,7,8,9,10-decahydrobenzo[b][1,5]diazacyclododecin-7-yl)-1H-1,2,3-triazole-4-carboxamide

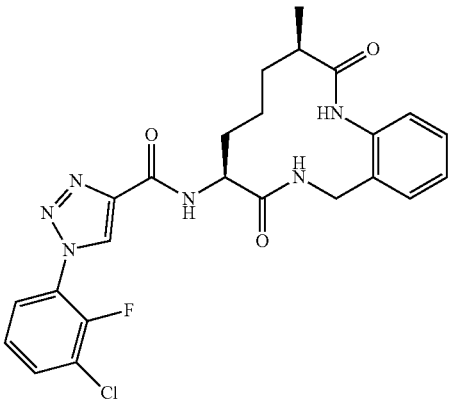 [SMILES: C[C@@H]1CCC[C@H](NC(=O)c2cn(-c3cccc(Cl)c3F)nn2)C(=O)NCc2ccccc2NC1=O]

23A. Preparation of 1-(3-chloro-2-fluorophenyl)-1H-1,2,3-triazole-4-carboxylic acid

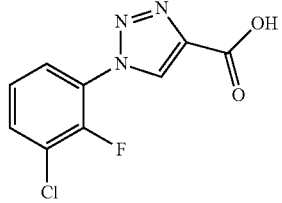 [SMILES: O=C(O)c1cn(-c2cccc(Cl)c2F)nn1]

To a solution of 3-chloro-2-fluoroaniline (1.2 g, 8.24 mmol) in TFA (4 ml), H$_2$O (2 ml) was added and the mixture was cooled to 0° C. NaNO$_2$ (1.12 g, 16.24 mmol) in H$_2$O (2 ml) was added dropwise (temperature kept <5° C.). After 0.5 h, NaN$_3$ (0.585 g, 9.0 mmol) was added portionwise. After stirring at rt overnight, the reaction was quenched with H$_2$O (100 ml), extracted with EtOAc (2×50 ml), dried over Na$_2$SO$_4$, and concentrated to give a solid mass. To a solution of the solid dissolved in DMSO (5 ml), L-proline (0.02 g), Cu(OAc)$_2$ (0.1 g) K$_2$CO$_3$ (1.5 g), sodium ascorbate (0.1 g), and excess t-butyl propiolate (3 ml) were added and the mixture heated at 75° C. overnight. The reaction was quenched with H$_2$O (100 ml), extracted with EtOAc (2×100 ml), washed with brine (50 ml), dried (MgSO$_4$), filtered, and concentrated. The crude product was purified by normal phase chromatography to give the t-butyl ester intermediate. An aliquot of this material (0.2 g) was dissolved in DCM (2 ml) and treated with TFA (1 ml) at rt. After stirring overnight, the reaction was quenched with H$_2$O (50 ml), extracted with EtOAc (2×100 ml), dried (MgSO$_4$), filtered, and evaporated to give a brown solid mass. This material was carried forward as is without further purification.). (ESI) m/z: 342.1 (M+H)+. 342.1 (M+H). $^1$H NMR (400 MHz, CD$_3$OD/CDCl3) δ 8.20 (s, 1H), 7.60-7.55 (dt, 1H), 7.42-7.37 (dt, 1H), 7.28-7.23 (dt, 1H).

23B. Preparation of 1-(3-chloro-2-fluorophenyl)-N-((3R,7S)-3-methyl-2,8-dioxo-1,2,3,4,5,6,7,8,9,10-decahydrobenzo[b][1,5]diazacyclododecin-7-yl)-1H-1,2,3-triazole-4-carboxamide A solution of 1-(3-chloro-2-fluorophenyl)-1H-1,2,3-triazole-4-carboxylic acid (0.018 g, 0.073 mmol), (3R,7S)-7-amino-3-methyl-4,5,6,7,9,10-hexahydrobenzo[b][1,5]diazacyclododecine-2,8(1H,3H)-dione (0.020 g, 0.073 mmol), EDC (0.028 g, 0.145 mmol), HOBT (0.022 g, 0.145 mmol), and Hunig's Base (0.063 ml, 0.363 mmol) in DMF (1.5 ml) was stirred. After stirring for 3 h, the crude reaction mixture was purified by reverse phase chromatography and freeze-dried to give the desired product (0.005 g, 13%) as a white solid. m/z: 499.3 (M+H)$^+$. $^1$H NMR (400 MHz, DMSO-d6) δ 9.04 (d, J=1.8 Hz, 1H), 8.86 (s, 1H), 8.26-8.19 (m, 2H), 7.82-7.75 (m, 2H), 7.50 (d, J=7.7 Hz, 1H), 7.42 (td, J=8.2, 1.4 Hz, 1H), 7.28-7.20 (m, 2H), 7.09-7.02 (m, 1H), 4.46-4.31 (m, 3H), 1.78 (d, J=7.7 Hz, 1H), 1.71-1.62 (m, 1H), 1.51-1.23 (m, 5H), 1.07 (d, J=6.8 Hz, 3H). Analytical HPLC (Method A) RT=8.02 min, purity=>95%; Factor XIa Ki=8, 730 nM, Plasma Kallikrein Ki=13,000 nM.

Example 24. Preparation of 1-(3-chloro-2-fluorophenyl)-5-methyl-N-((3R,7S)-3-methyl-2,8-dioxo-1,2,3,4,5,6,7,8,9,10-decahydrobenzo[b][1,5]diazacyclododecin-7-yl)-1H-imidazole-4-carboxamide

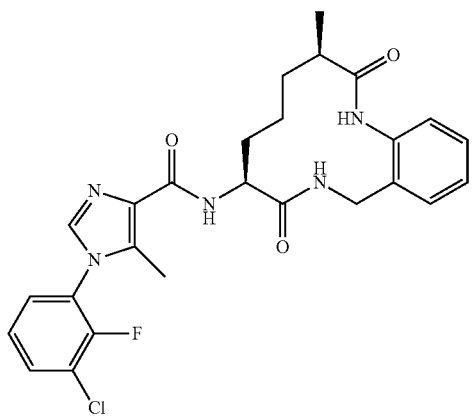 [SMILES: Cc1c(C(=O)N[C@H]2CCC[C@@H](C)C(=O)Nc3ccccc3CNC2=O)ncn1-c1cccc(Cl)c1F]

24A. Preparation of Ethyl 3-((3-chloro-2-fluorophenyl)amino)-2-nitrobut-2-enoate

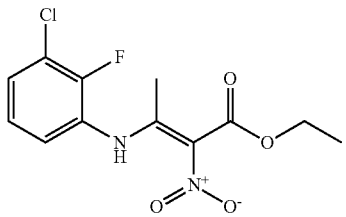 [SMILES: CCOC(=O)/C(=C(\C)Nc1cccc(Cl)c1F)[N+](=O)[O-]]

Using a modified procedure described by Gomez-Sanchez. (Reference: Gomez-Sanchez, A; Hidalgo-Garcia, F. J.; Chiara, J. L; Bellanato, J.; Anales De Quimica, 1985, 81(2), 139.) A clear, faint yellow solution of ethyl nitroacetate (4.17 ml, 37.6 mmol) and triethylorthoacetate (6.93 ml, 37.6 mmol) in toluene (9.39 mL) was heated to 110° C. A Dean-Stark trap was used to azeotrope the ethanol. Approximately every 30 min, the solvent was removed from the Dean-Stark and additional toluene (6 mL) was added to the reaction flask. Over the course of the reaction the color became a clear, dull yellow color. After 7.5 h, the reaction was stopped and it was cooled to rt. Excess solvent and starting materials were removed by distillation (5 mm Hg at 100° C.) leaving ethyl 3-ethoxy-2-nitrobut-2-enoate (5.46 g) as an orange liquid. An orange solution of 3-chloro-2-fluoroaniline (5.86 g, 40.2 mmol) and ethyl 3-ethoxy-2-nitrobut-2-enoate (5.45 g, 26.8 mmol) in ethanol (13.41 mL) was stirred at rt. After 7 h, the reaction was stopped and concentrated to give an orange oil. The orange oil was diluted with EtOAc and washed with 1.0 N HCl (2×), saturated NaHCO3, brine, dried over sodium sulfate, filtered and concentrated to give an orange oil. Purification by normal phase chromatography gave the desired intermediate (2.90 g, 36%) as a viscous orange-yellow oil. $^1$HNMR indicated a 1:1 E:Z mixture. MS (ESI) m/z: 325.0 (M+H)+.

24B. Preparation of Ethyl 1-(3-chloro-2-fluorophenyl)-5-methyl-1H-imidazole-4-carboxylate Using a modified procedure described by Gomez-Sanchez. (Reference: Gomez-Sanchez, A.; Hidalgo, F. J.; Chiara, J. L.; J. Heterocyclic Chem., 1987, 24, 1757.) A clear, yellow solution of 24A (2.90 g, 9.58 mmol) in triethylorthoformate (96 ml) was degassed with argon for 20 min. Next, platinum on carbon (0.935 g, 0.479 mmol) was added. The flask was equipped with a reflux condenser and the reaction was purged with hydrogen (balloon) for several minutes. The reaction was stirred under a hydrogen atmosphere and the reaction was warmed to 75° C. After a total of 4 h, the reaction was cooled to rt. The reaction was placed under vacuum for several minutes and then backfilled with argon. The process was repeated a total of 5 times. Next, Celite® was added and the reaction was filtered, washing with ethanol. The filtrate was concentrated to give a clear, yellow-brown oil weighing 3.17 g. Purification by normal phase chromatography provided the desired product (1.64 g, 61%) as a white solid. MS (ESI) m/z: 283.0 (M+H)+.

24C. Preparation of 1-(3-Chloro-2-fluorophenyl)-5-methyl-1H-imidazole-4-carboxylic acid, HCl

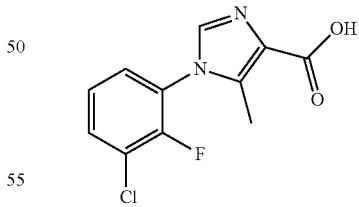

To a clear, colorless solution 24B (1.64 g, 5.80 mmol) in methanol (29.0 ml) was added 1.0 M NaOH (17.40 ml, 17.40 mmol). The reaction was stirred at rt. After 20 h, the reaction was concentrated under high vacuum with minimal heating to give a white solid. The solid was suspended in water and 1.0 N HCl was added until the mixture was at a pH=1-2. The solid was collected by filtration and rinsed with water, air-dried, and dried under high vacuum to give 24C (1.44 g, 81%) as a white solid. MS (ESI) m/z: 255.0 (M+H)$^+$ and 257.0 (M+2+H)$^+$. $^1$H NMR (500 MHz, DMSO-d$_6$) δ

7.91 (d, J=0.5 Hz, 1H), 7.83 (ddd, J=8.3, 6.9, 1.7 Hz, 1H), 7.63 (td, J=7.5, 1.5 Hz, 1H), 7.46 (td, J=8.1, 1.4 Hz, 1H), 2.32 (s, 3H).

24D. Preparation of 1-(3-chloro-2-fluorophenyl)-5-methyl-N-((3R,7S)-3-methyl-2,8-dioxo-1,2,3,4,5,6,7,8,9,10-decahydrobenzo[b][1,5]diazacyclododecin-7-yl) 1H-imidazole-4-carboxamide A solution of 1-(3-chloro-2-fluorophenyl)-5-methyl-1H-imidazole-4-carboxylic acid (0.018 g, 0.073 mmol), (3R,7S)-7-amino-3-methyl-4,5,6,7,9,10-hexahydrobenzo[b][1,5]diazacyclododecine-2,8(1H,3H)-dione (0.020 g, 0.073 mmol), EDC (0.028 g, 0.145 mmol), HOBT (0.022 g, 0.145 mmol), and Hunig's Base (0.063 ml, 0.363 mmol) in DMF (1.5 ml) was stirred at RT for 2 h, 55° C. for 2 h. The crude reaction mixture was purified by reverse phase chromatography and freeze-dried to give the desired product. MS (ESI) m/z: 512.4 (M+H)⁺. ¹H NMR (400 MHz, CD₃OD) δ 7.69-7.59 (m, 2H), 7.54 (d, J=8.1 Hz, 1H), 7.38-7.22 (m, 5H), 7.12-7.05 (m, 1H), 4.59 (d, J=14.5 Hz, 1H), 4.41-4.30 (m, 2H), 2.48-2.40 (m, 1H), 2.27 (s, 3H), 1.92 (d, J=5.1 Hz, 1H), 1.78-1.68 (m, 1H), 1.63-1.55 (m, 1H), 1.46 (br. s., 2H), 1.35-1.27 (m, 1H), 1.15 (d, J=7.0 Hz, 3H). Analytical HPLC (Method A) RT=7.94 min, purity=>95%; Factor XIa Ki=7, 410 nM, Plasma Kallikrein Ki=4,360 nM.

Example 25. Preparation of (S)-1-(3-chloro-2-fluorophenyl)-N-(2,9-dioxo-1,2,3,4,5,6,7,8,9,10-decahydrobenzo[b][1,4]diazacyclododecin-3-yl)-1H-1,2,3-triazole-4-carboxamide

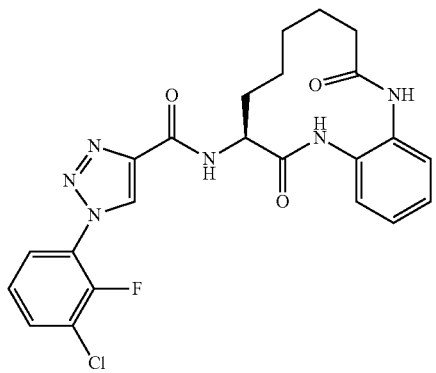 [SMILES: O=C1CCCCC[C@H](NC(=O)c2cn(-c3cccc(Cl)c3F)nn2)C(=O)Nc2ccccc2N1]

25A. Preparation of (S)-tert-butyl (1-((2-aminophenyl)amino)-1-oxopent-4-en-2-yl)carbamate

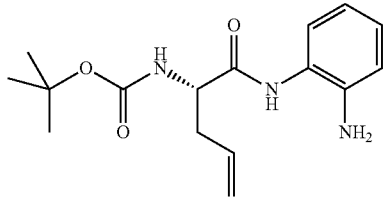 [SMILES: C=CC[C@H](NC(=O)OC(C)(C)C)C(=O)Nc1ccccc1N]

1-Propanephosphonic acid cyclic anhydride (50% in EtOAc) (1.064 g, 1.673 mmol) was added to a solution of (S)—N-Boc-allylglycine (0.300 g, 1.394 mmol), benzene-1,2-diamine (0.181 g, 1.673 mmol), and DIPEA (0.730 ml, 4.18 mmol) in EtOAc (13.94 ml). After 14 h, the reaction mixture was diluted further with EtOAc (20 mL), washed with saturated NaHCO₃, dried over Na₂SO₄, filtered, and concentrated. The crude material was purified by normal phase column chromatography to give (S)-tert-butyl (1-((2-aminophenyl)amino)-1-oxopent-4-en-2-yl)carbamate (0.364 g, 86% yield) as a white foam. MS (ESI) m/z: 306.3 (M+H)⁺.

25B. Preparation of (S)-tert-butyl (1-oxo-1-((2-(pent-4-enamido)phenyl)amino)pent-4-en-2-yl)carbamate

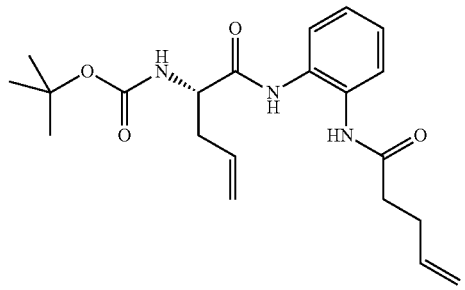 [SMILES: C=CCCC(=O)Nc1ccccc1NC(=O)[C@H](CC=C)NC(=O)OC(C)(C)C]

4-Pentenoyl chloride (0.198 mL, 1.793 mmol) was added to a stirring mixture of (S)-tert-butyl (1-((2-aminophenyl)amino)-1-oxopent-4-en-2-yl)carbamate (0.365 g, 1.195 mmol) and DIPEA (0.626 ml, 3.59 mmol) in DCM (20 ml) at 0° C. under nitrogen. The reaction was allowed to come to rt. After 1 h, the reaction mixture was washed with 1.0M HCl solution, saturated NH₄Cl, and brine, Na₂SO₄, filtered, and concentrated. The crude material was purified by normal phase column chromatography to give (S)-tert-butyl (1-oxo-1-((2-(pent-4-enamido)phenyl)amino)pent-4-en-2-yl)carbamate (0.383 g, 83%) as a white foam. MS (ESI) m/z: 388 (M+H)⁺.

25C. Preparation of (S)-tert-butyl (2,9-dioxo-1,2,3,4,5,6,7,8,9,10-decahydrobenzo[b][1,4]diazacyclododecin-3-yl)carbamate

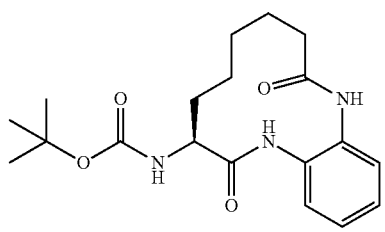 [SMILES: CC(C)(C)OC(=O)N[C@H]1CCCCCC(=O)Nc2ccccc2NC1=O]

(S)-tert-butyl (1-oxo-1-((2-(pent-4-enamido)phenyl)amino)pent-4-en-2-yl)carbamate (0.100 g, 0.258 mmol) was dissolved in anhydrous DCE (12 ml) and degassed with a stream of Ar. After 15 minutes, Grubbs II (0.088 g, 0.103 mmol) was added and the mixture irradiated at 120° C. in a microwave for 30 min. The reaction mixture was concentrated. The residue was dissolved in EtOH (10 mL), treated with PtO₂ (5.86 mg, 0.026 mmol), and subjected to a H₂ atmosphere (50 psi) overnight. The reaction mixture was filtered through a pad of Celite®, concentrated, and purified by reverse phase chromatography to give the desired product (0.0472 g, 51%). MS (ESI) m/z: 362.3 (M+H)+. 1H NMR (400 MHz, DMSO-d6) δ 9.64 (s, 1H), 9.04 (s, 1H), 7.30-7.24 (m, 2H), 7.22-7.19 (m, 1H), 7.18-7.13 (m, 1H), 6.79 (d, J=7.7 Hz, 1H), 4.22-4.15 (m, J=3.8 Hz, 1H), 2.28-2.22 (m, J=2.2 Hz, 2H), 1.88-1.69 (m, 2H), 1.66-1.55 (m, 2H), 1.45-1.36 (m, 12H), 1.33-1.24 (m, 1H).

25D. Preparation of (S)-1-(3-chloro-2-fluorophenyl)-N-(2,9-dioxo-1,2,3,4,5,6,7,8,9,10-decahydrobenzo[b][1,4]diazacyclododecin-3-yl)-1H-1,2,3-triazole-4-carboxamide (S)-tert-butyl (2,9-dioxo-1,2,3,4,5,6,7,8,9,10-decahydrobenzo[b][1,4]diazacyclo-dodecin-3-yl)carbamate 25C (0.015 g, 0.042 mmol) was dissolved in THF (1 ml) and treated with HCl (4.0M in dioxane) (1.0 ml, 4.00 mmol). After 2 h, the reaction mixture was concentrated to dryness. The amine HCl salt was dissolved in DMF (1 ml) and treated with 1-(3-chloro-2-fluorophenyl)-1H-1,2,3-triazole-4-carboxylic acid (10.03 mg, 0.042 mmol), DIPEA (0.072 ml, 0.415 mmol), and T3P (50% in EtOAc) (0.030 ml, 0.050 mmol), respectively. After 14 h, the crude reaction mixture was purified reverse phase chromatography and freeze-dried to give (S)-1-(3-chloro-2-fluorophenyl)-N-(2,9-dioxo-1,2,3, 4,5,6,7,8,9,10-decahydrobenzo[b][1,4]diazacyclododecin-3-yl)-1H-1,2,3-triazole-4-carboxamide (0.004 g, 7.59 µmol, 18.29% yield) as a off-white solid. MS (ESI) m/z: 485.1 (M+H)+. 1H NMR (500 MHz, DMSO-d6) δ 9.79 (s, 1H), 9.35 (s, 1H), 9.17 (d, J=1.7 Hz, 1H), 8.34 (d, J=7.4 Hz, 1H), 7.88 (dddd, J=8.1, 6.6, 4.7, 1.5 Hz, 2H), 7.51 (td, J=8.2, 1.5 Hz, 1H), 7.35-7.21 (m, 3H), 7.18 (dd, J=7.3, 1.8 Hz, 1H), 4.79 (td, J=6.9, 4.0 Hz, 1H), 2.33-2.23 (m, 2H), 1.99-1.85 (m, 3H), 1.72-1.63 (m, 1H), 1.54-1.39 (m, 4H). Analytical HPLC (Method X) RT=6.086 min, purity=92%; Factor XIa Ki=6,000 nM, Plasma Kallikrein Ki>13,000 nM.

Example 26. Preparation of (S)-3-(1-(3-chloro-2-fluorophenyl)-5-methyl-1H-pyrazole-4-carboxamido)-2,9-dioxo-1,2,3,4,5,6,7,8,9,10-decahydrobenzo[b][1,4]diazacyclododecine-12-carboxylic acid

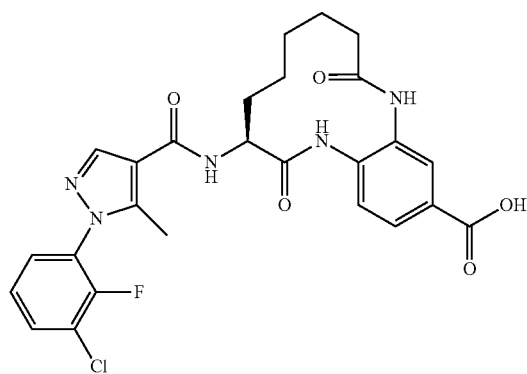 [SMILES: Cc1c(C(=O)N[C@H]2CCCCCC(=O)Nc3cc(C(=O)O)ccc3NC2=O)cnn1-c1cccc(Cl)c1F]

26A. Preparation of methyl 4-amino-3-(pent-4-enamido)benzoate

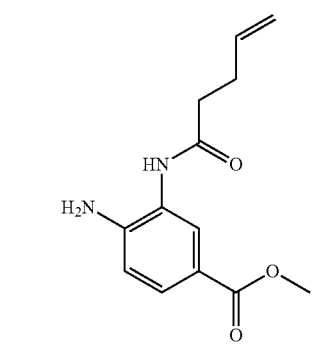 [SMILES: C=CCCC(=O)Nc1cc(C(=O)OC)ccc1N]

4-Pentenoyl chloride (0.844 ml, 7.64 mmol) was added to a stirring mixture of methyl 3-amino-4-nitrobenzoate (0.500 g, 2.55 mmol) and DIPEA (1.336 ml, 7.65 mmol) in DCM (20 mL) at 0° C. under nitrogen. The reaction was allowed to come to ambient temperature. THF (20 mL) and DMF (0.5 mL) were added to aid dissolution. After 14 h, the reaction mixture was diluted further with DCM, washed with 1.0M HCl solution, saturated NH4Cl, and brine, dried over Na2SO4, filtered, and concentrated. The crude material was purified by normal phase column chromatography. The nitro intermediate was dissolved in MeOH (25 ml), treated with Zn (1.666 g, 25.5 mmol) followed by NH4Cl (0.273 g, 5.10 mmol), and heated at 65° C. overnight. The suspension was filtered hot through a plug of Celite® and the filtercake washed with hot MeOH. The filtrate was concentrated and dried under vacuum to give a yellow solid. Carried forward as is without further purification. MS (ESI) m/z: 249.0 (M+H)+.

26B. Preparation of (S)-methyl 4-(2-((tert-butoxycarbonyl)amino)pent-4-enamido)-3-(pent-4-enamido)benzoate

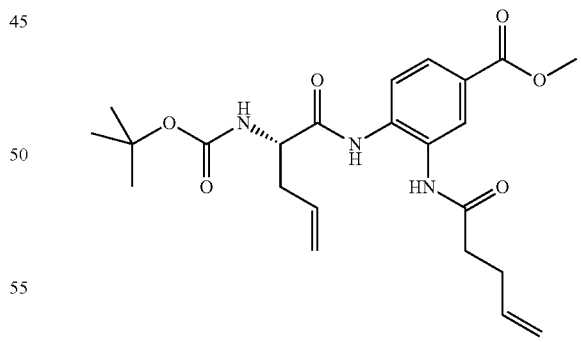

POCl3 (0.391 g, 2.55 mmol) was added dropwise to a solution of (S)-2-((tert-butoxycarbonyl)amino)pent-4-enoic acid (0.549 g, 2.55 mmol) and methyl 4-amino-3-(pent-4-enamido)benzoate (0.633 g, 2.55 mmol) in pyridine (10.20 ml) at −15° C. under a blanket of argon. After stirring at rt for 3 h, the reaction was quenched with water and extracted with EtOAc. The organic layer was washed with 1.0M HCl solution, water, brine, dried over sodium sulfate, filtered, and concentrated. The crude product was purified by normal phase chromatography to give (S)-methyl 4-(2-((tert-butoxycarbonyl)amino)pent-4-enamido)-3-(pent-4-enamido)benzoate (0.220 g, 0.494 mmol, 19.37% yield) as a solid. MS (ESI) m/z: 446.1 (M+H)$^+$.

26C. Preparation of (S)-methyl 3-((tert-butoxycarbonyl)amino)-2,9-dioxo-1,2,3,4,5,6,7,8,9,10-decahydrobenzo[b][1,4]diazacyclododecine-12-carboxylate

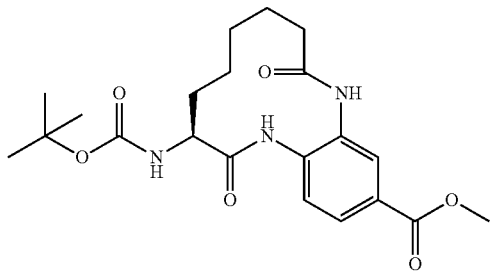 [SMILES: COC(=O)c1ccc2c(c1)NC(=O)CCCCC[C@H](NC(=O)OC(C)(C)C)C(=O)N2]

(S)-methyl 4-(2-((tert-butoxycarbonyl)amino)pent-4-enamido)-3-(pent-4-enamido)benzoate 26B (0.084 g, 0.189 mmol) was added to DCE (12.57 ml) and degassed with a stream of argon for 30 minutes. Grubbs II was added and the mixture irradiated at 120° C. for 25 minutes. The crude material purified by reverse phase chromatography to give the desired RCM product intermediate as brown oil. The olefin was dissolved in EtOH (10 ml), treated with PtO$_2$ (0.043 g, 0.189 mmol), and subjected to a H$_2$ atmosphere (55 psi). After 14 h, the reaction mixture was filtered through a plug of Celite®, filtered, concentrated and carried forward as is without further purification. (ESI) m/z: 418.2 (M+H)$^+$.

26D. Preparation of Ethyl 1-(3-chloro-2-fluorophenyl)-5-methyl-1H-pyrazole-4-carboxylate

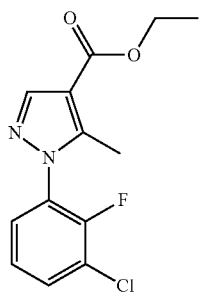 [SMILES: CCOC(=O)c1cnn(-c2cccc(Cl)c2F)c1C]

A solution of ethyl 2-((dimethylamino) methylene)-3-oxobutanoate (0.517 g, 2.79 mmol), (3-chloro-2-fluorophenyl)hydrazine hydrochloride (0.500 g, 2.54 mmol) in EtOH (2.54 ml) and TEA (0.707 ml, 5.08 mmol) was stirred at rt. After 10 min, the reaction mixture was concentrated and purified by normal phase chromatography. The desired product, ethyl 1-(3-chloro-2-fluorophenyl)-5-methyl-1H-pyrazole-4-carboxylate (200 mg, 28%), was obtained as an off white solid. MS (ESI) m/z: 283.1 (M+H)$^+$.

26E. Preparation of 1-(3-Chloro-2-fluorophenyl)-5-methyl-1H-pyrazole-4-carboxylic acid

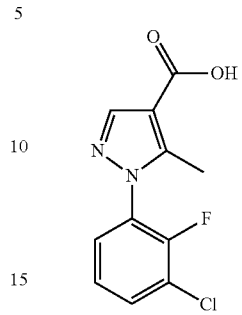

1-(3-Chloro-2-fluorophenyl)-5-methyl-1H-pyrazole-4-carboxylic acid: To a solution of (50 mg, 0.177 mmol) in MeOH (0.884 mL) was added 1 N NaOH (aqueous) (1.061 ml, 1.061 mmol) and the reaction was stirred at 50° C. in a sealed vial for 3 h. The reaction mixture was then cooled to rt and concentrated. The residue was then partitioned between 1 N HCl (aqueous) and EtOAc. The layers were separated and the aqueous layer was extracted with EtOAc. The organic layers were combined, washed with brine, and concentrated to give 27C as an off-white solid (48 mg, 107%). MS (ESI) m/z: 255.0 (M+H)$^+$.

26F. Preparation of (S)-3-(1-(3-chloro-2-fluorophenyl)-5-methyl-1H-pyrazole-4-carboxamido)-2,9-dioxo-1,2,3,4,5,6,7,8,9,10-decahydrobenzo[b][1,4]-diazacyclododecine-12-carboxylic acid HCl (4.0M in dioxane) (1001 µl, 4.01 mmol) was added to a solution of (S)-methyl 3-((tert-butoxycarbonyl)amino)-2,9-dioxo-1,2,3,4,5,6,7,8,9,10-decahydrobenzo[b][1,4]diazacyclododecine-12-carboxylate 27A (24 mg, 0.057 mmol) in MeOH (0.5 mL) at rt. After 2 hours, the reaction mixture was concentrated to dryness and placed under vacuum. The residue, 1-(3-chloro-2-fluorophenyl)-5-methyl-1H-pyrazole-4-carboxylic acid 27C (14.57 mg, 0.057 mmol), EDC (13.16 mg, 0.069 mmol), 1-Hydroxybenzotriazole hydrate (10.51 mg, 0.069 mmol), and DIPEA (50.0 µl, 0.286 mmol) were added to DMF (1.0 ml). After 14 h, the reaction mixture was partitioned between water and EtOAc. The aqueous layer was extracted with additional EtOAc. The combined organic layers were washed with 1.0M HCl solution, water, brine, dried over sodium sulfate, filtered, and concentrated. The ester was hydrolyzed by dissolution in THF/MeOH/H$_2$O (1/1/1 mL) and treatment with LiOH monohydrate (12.00 mg, 0.286 mmol) and heating to 50° C. for 2 hours. The organics were removed and the remaining aqueous layer acidified with 1.0M HCl solution. The solution was extracted with EtOAc (3×5 mL). The combined organic layers were washed were concentrated and purified by reverse phase chromatography and freeze-dried to give the desired product a white solid. MS (ESI) m/z: 542.1 (M+H)$^+$. $^1$H NMR (400 MHz, CD$_3$OD) δ 8.20 (s, 1H), 8.04-7.97 (m, 1H), 7.88 (s, 1H), 7.73 (t, J=6.9 Hz, 1H), 7.56-7.36 (m, 3H), 4.80-4.70 (m, 1H), 2.53-2.39 (m, 4H), 2.08-1.94 (m, 3H), 1.89-1.76 (m, 2H), 1.71-1.57 (m, 3H). Analytical HPLC (Method X) RT=5.88 min, purity=95%; Factor XIa Ki=1,738 nM, Plasma Kallikrein Ki=765 nM.

Example 27. Preparation of methyl (S)-3-(4-(5-chloro-2-(4-(trifluoromethyl)-1H-1,2,3-triazol-1-yl)phenyl)-6-oxopyrimidin-1(6H)-yl)-2,9-dioxo-1,2,3,4,5,6,7,8,9,10-decahydrobenzo[b][1,4]diazacyclododecine-12-carboxylate

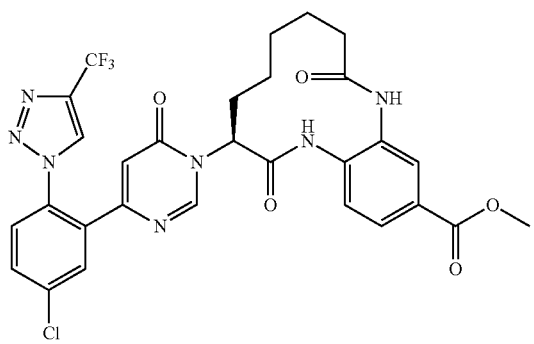 [SMILES: COC(=O)c1ccc2c(c1)NC(=O)CCCCC[C@H](n1cnc(-c3cc(Cl)ccc3-n3cc(C(F)(F)F)nn3)cc1=O)C(=O)N2]

27A. Preparation of Methyl (S)-3-amino-2,9-dioxo-1,2,3,4,5,6,7,8,9,10-decahydrobenzo[b][1,4]diazacyclododecine-12-carboxylate

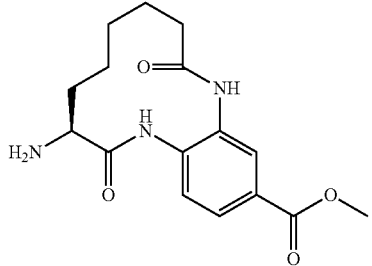 [SMILES: COC(=O)c1ccc2c(c1)NC(=O)CCCCC[C@H](N)C(=O)N2]

TFA (0.364 ml, 4.72 mmol) was added to a solution of (S)-methyl 3-((tert-butoxycarbonyl)amino)-2,9-dioxo-1,2,3,4,5,6,7,8,9,10-decahydrobenzo[b][1,4]-diazacyclododecine-12-carboxylate (0.099 g, 0.236 mmol) in DCM (2 ml). After 2 h, the reaction mixture was concentrated to dryness. The residue was neutralized by dissolving in MeOH, passing through a NaHCO$_3$ cartridge, and the filtrate concentrated to dryness. The resulting tan solid carried forward to the next reaction. MS (ESI) m/z: 320.1 (M+H)$^+$.

27B. Preparation of methyl (S)-3-(4-(5-chloro-2-(4-(trifluoromethyl)-1H-1,2,3-triazol-1-yl)phenyl)-6-oxopyrimidin-1(6H)-yl)-2,9-dioxo-1,2,3,4,5,6,7,8,9,10-decahydrobenzo[b][1,4]diazacyclododecine-12-carboxylate To an off-white suspension of 6-(5-chloro-2-(4-(trifluoromethyl)-1H-1,2,3-triazol-1-yl)phenyl)pyrimidin-4-ol (0.064 g, 0.188 mmol) and HATU (0.093 g, 0.244 mmol) in ACN (1.879 ml) was added dropwise DBU (0.042 ml, 0.282 mmol). The resulting yellow solution was stirred at rt. After 15 min, a solution of (S)-methyl 3-amino-2,9-dioxo-1,2,3,4,5,6,7,8,9,10-decahydrobenzo[b][1,4]diazacyclododecine-12-carboxylate (0.060 g, 0.188 mmol) in DMF (1.879 ml) was added. After 14 h, the crude reaction mixture was purified by reverse phase chromatography and freeze-dried to give the desired product (0.045 g, 35%) as a white solid. MS (ESI) m/z: 644.1 (M+H)$^+$. $^1$H NMR (500 MHz, DMSO-d6) δ 9.98 (s, 1H), 9.63 (s, 1H), 9.28 (s, 1H), 8.36 (s, 1H), 7.98 (d, J=2.2 Hz, 1H), 7.90-7.82 (m, 3H), 7.77 (d, J=1.9 Hz, 1H), 7.52 (d, J=8.3 Hz, 1H), 6.54 (s, 1H), 5.41 (dd, J=10.6, 3.4 Hz, 1H), 3.86 (s, 3H), 2.42-2.36 (m, 1H), 2.32-2.25 (m, 1H), 2.15-2.07 (m, 1H), 1.86-1.76 (m, 2H), 1.73-1.68 (m, 1H), 1.64-1.55 (m, 2H), 1.53-1.48 (m, 1H), 1.44-1.38 (m, 1H). Analytical HPLC (Method A) RT=8.80 min, purity=95%; Factor XIa Ki=561 nM, Plasma Kallikrein Ki>13,000 nM.

Example 28. Preparation of (S)-3-(4-(5-chloro-2-(4-(trifluoromethyl)-1H-1,2,3-triazol-1-yl)phenyl)-6-oxopyrimidin-1(6H)-yl)-2,9-dioxo-1,2,3,4,5,6,7,8,9,10-decahydrobenzo[b][1,4]diazacyclododecine-12-carboxylic acid

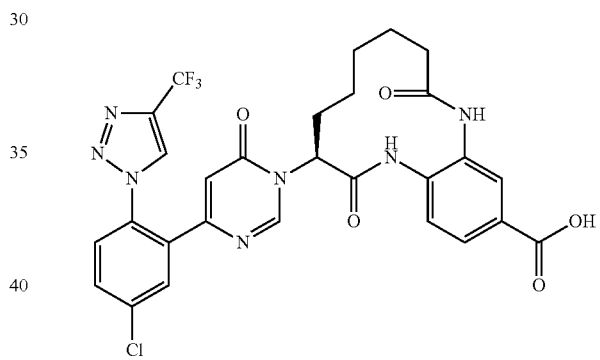

LiOH monohydrate (0.013 g, 0.311 mmol) was added to a stirring solution of (S)-methyl 3-(4-(5-chloro-2-(4-(trifluoromethyl)-1H-1,2,3-triazol-1-yl)phenyl)-6-oxopyrimidin-1(6H)-yl)-2,9-dioxo-1,2,3,4,5,6,7,8,9,10-decahydrobenzo[b][1,4]-diazacyclododecine-12-carboxylate (0.040 g, 0.062 mmol) in THF (0.466 ml)/H2O (0.155 ml) and heated at 50° C. After 4 h, the reaction mixture was cooled to 0° C., acidified using 1.0N HCl solution, extracted with EtOAc, and concentrated. The crude material was purified by reverse phase chromatography and freeze-dried to give the desired product (1.5 mg, 3.3%) as a white solid. MS (ESI) m/z: 630.1 (M+H)$^+$. $^1$H NMR (400 MHz, CD$_3$OD) δ 8.74 (s, 1H), 8.31 (s, 1H), 7.88 (d, J=8.1 Hz, 1H), 7.82-7.75 (m, 2H), 7.66 (dd, J=8.4, 2.4 Hz, 1H), 7.59 (d, J=8.4 Hz, 1H), 7.32 (d, J=8.4 Hz, 1H), 6.37 (s, 1H), 5.44 (br. s., 1H), 2.53-2.44 (m, 2H), 2.28-2.19 (m, 2H), 1.81 (br. s., 2H), 1.63 (d, J=6.4 Hz, 1H), 1.25-1.14 (m, 4H). Analytical HPLC (Method X) RT=5.81 min, purity=90%; Factor XIa Ki=173 nM, Plasma Kallikrein Ki=11,600 nM.

What is claimed is:

1. A compound of Formula (I):

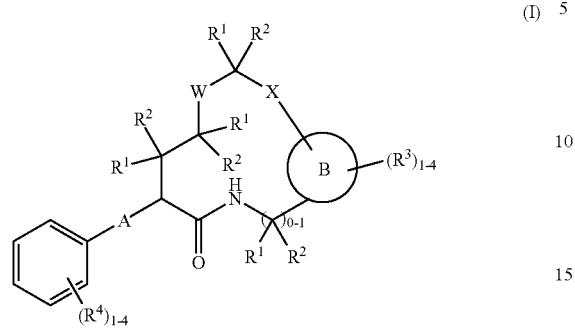

or a stereoisomer, a tautomer, a pharmaceutically acceptable salt thereof, wherein:

A is independently selected from

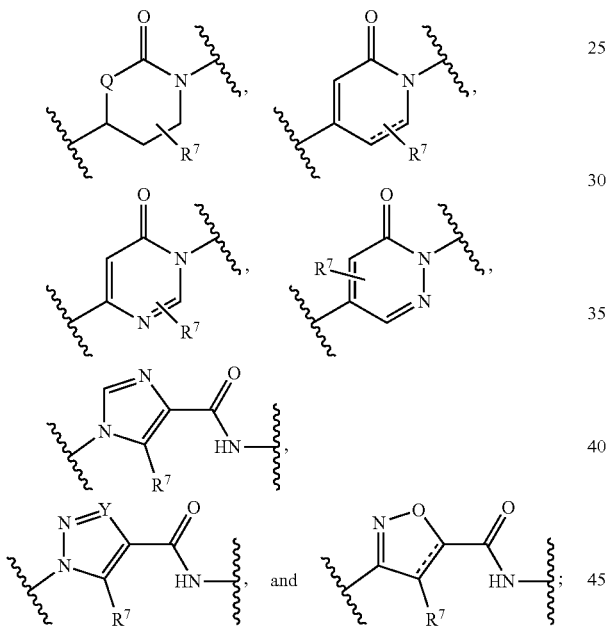

---- is an optional bond;

Ring B is independently selected from aryl and 5- to 10-membered heterocyclyl;

Q is independently selected from O, NH, and CH$_2$;

W is independently selected from (CR$^1$R$^2$)$_{1-2}$, O, NH, and N(C$_{1-4}$ alkyl);

X is independently selected from —CR$^8$NH—, —NHC(=O)- and —C(=O)NH—; provided when W is O, NH, and N(C$_{1-4}$ alkyl), X is not —NHC(=O)-;

Y is independently selected from N and CR$^7$;

R$^1$ and R$^2$ are independently selected from H, halogen, C$_{1-4}$ alkyl substituted with 0-4 R$^e$, OR$^b$, and C$_{3-5}$ cycloalkyl substituted with 1-4 R$^6$;

R$^3$ is independently selected from H, NO$_2$, =O, halogen, C$_{1-4}$ alkyl substituted with 1-5 R$^5$, C$_{2-4}$ alkenyl substituted with 1-5 R$^5$, C$_{2-4}$ alkynyl substituted with 1-5 R$^5$, CN, —(CH$_2$)$_n$—OR$^b$, —(CH$_2$)$_n$—NR$^a$R$^a$, —(CH$_2$)$_n$—C(=O)R$^b$, —(CH$_2$)$_n$—C(=O)OR$^b$, —(CH$_2$)$_n$—NR$^a$C(=O)OR$^b$, —(CH$_2$)$_n$—NR$^a$C(=O)R$^b$, —(CH$_2$)$_n$—NR$^a$C(N—CN)NR$^a$R$^a$, —(CH$_2$)$_n$—NR$^a$C(NH)NR$^a$R$^a$, —(CH$_2$)$_n$—N=CR$^b$NR$^a$R$^a$, —(CH$_2$)$_n$—NR$^a$C(=O)NR$^a$R$^a$, —(CH$_2$)$_n$—C(=O)NR$^a$R$^a$, —(CH$_2$)$_n$—NR$^a$C(=S)NR$^a$C(=O)R$^b$, —(CH$_2$)$_n$—S(=O)$_p$R$^c$, —(CH$_2$)$_n$—S(=O)$_p$NR$^a$R$^a$, —(CH$_2$)$_n$—NR$^a$S(=O)$_p$NR$^a$R$^a$, —(CH$_2$)$_n$—NR$^a$S(=O)$_p$R$^c$, —(CR$_d$R$_d$)$_n$—C$_{3-10}$ carbocyclyl substituted with 1-5 R$^5$, and —(CR$_d$R$_d$)$_n$-4- to 10-membered heterocyclyl substituted with 1-5 R$^5$; optionally, two adjacent R$^3$ groups on the carbocyclyl and heterocyclyl may form a ring substituted with 1-5 R$^5$;

R$^4$ is independently selected from H, halogen, CN, —(CH$_2$)$_n$NR$^a$R$^a$, C$_{1-6}$ alkyl substituted with 1-5 R$^{10}$, —(CH$_2$)$_n$OR$^b$, —(CH$_2$)$_n$C(=O)R$^b$, —(CH$_2$)$_n$C(=O)OR$^b$, —(CH$_2$)$_n$—NR$^a$C(=O)OR$^b$, —(CH$_2$)$_n$—NR$^a$C(=O)R$^b$, —(CH$_2$)$_n$—NR$^a$C(N—CN)NR$^a$R$^a$, —(CH$_2$)$_n$—NR$^a$C(NH)NR$^a$R$^a$, —(CH$_2$)$_n$—N=CR$^b$NR$^a$R$^a$, —(CH$_2$)$_n$—NR$^a$C(=O)NR$^a$R$^a$, —(CH$_2$)$_n$—C(=O)NR$^a$R$^a$, —(CH$_2$)$_n$—NR$^a$C(=S)NR$^a$C(=O)R$^b$, —(CH$_2$)$_n$—S(=O)$_p$R$^c$, —(CH$_2$)$_n$—S(=O)$_p$NR$^a$R$^a$, —(CH$_2$)$_n$—NR$^a$S(=O)$_p$NR$^a$R$^a$, —(CH$_2$)$_n$—NR$^a$S(=O)$_p$R$^c$, —(CH$_2$)$_n$-aryl substituted with 1-5 R$^{10}$, —(CH$_2$)$_n$—C$_{3-6}$ cycloalkyl substituted with 1-5 R$^{10}$, and —(CH$_2$)$_n$-4-6 membered heterocyclyl substituted with 1-5 R$^{10}$;

R$^5$, at each occurrence, is independently selected from H, D, —(CH$_2$)$_n$—OR$^b$, =O, —(CH$_2$)$_n$NH$_2$, —(CH$_2$)$_n$CN, halogen, C$_{1-6}$ alkyl, —(CH$_2$)$_n$—C(=O)OR$^b$, —(CH$_2$)$_n$—OR$^b$, —(CH$_2$)$_n$—C$_{3-10}$ carbocyclyl substituted with 0-5 R$^e$, —(CH$_2$)$_n$-4- to 10-membered heterocyclyl substituted with 0-5 R$^e$, and —O-4- to 10-membered heterocyclyl substituted with 0-5 R$^e$;

R$^6$ is independently selected from H, OH, =O, —(CH$_2$)$_n$NH$_2$, —(CH$_2$)$_n$CN, halogen, C$_{1-6}$ alkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, —(CH$_2$)$_n$—C$_{3-10}$ carbocycle substituted with 0-5 R$^e$, —(CH$_2$)$_n$-4- to 10-membered heterocycle substituted with 0-5 R$^e$, and —(CH$_2$)$_n$-4- to 10-membered heterocycle substituted with 0-5 R$^e$;

R$^7$ is independently selected from H, CN, OR$^b$, halogen, NR$^a$R$^a$, and C$_{1-3}$ alkyl substituted with 0-5 R$^e$;

R$^8$ is independently selected from H, C$_{1-4}$ alkyl substituted with 0-3 R$^e$, CO$_2$H, —(CH$_2$)$_n$CO$_2$(C$_{1-4}$ alkyl), —(CH$_2$)$_n$CO$_2$NH$_2$, —CONH(C$_{1-4}$ alkoxy), —CO$_2$(CH$_2$)$_2$O(C$_{1-4}$ alkyl), —CO$_2$(CH$_2$)$_2$N(C$_{1-4}$ alkyl)$_2$, —CONH(CH$_2$)$_2$O(C$_{1-4}$ alkyl), —CONH(CH$_2$)$_2$N(C$_{1-4}$ alkyl)$_2$, —CON(C$_{1-4}$ alkyl)(CH$_2$)$_2$O(C$_{1-4}$ alkyl), —CON(C$_{1-4}$ alkyl)(CH$_2$)$_2$N(C$_{1-4}$ alkyl)$_2$, —CONHBn, —CONH(OBn), —(CO)$_{0-1}$(CH$_2$)$_{0-3}$—C$_{3-6}$ carbocycle, and —(CH$_2$)$_{0-1}$-(CO)$_{0-1}$-(V)$_{0-1}$—(CH$_2$)$_{0-2}$-(4- to 6-membered heterocycle comprising carbon atoms and 1-4 heteroatoms selected from N, NH, N(C$_{1-4}$ alkyl), O, and S(O)$_p$); wherein said carbocycle and heterocycle are substituted with 1-2 R$^9$; V is independently selected from O, NH and N(C$_{1-4}$ alkyl);

R$^9$ is independently selected from H, halogen, OH, CHF$_2$, CF$_3$, C$_{1-4}$ alkoxy, CH$_2$OH, CO$_2$H, CO$_2$(C$_{1-4}$ alkyl), CONH$_2$, and C$_{1-4}$ alkyl;

R$^{10}$, at each occurrence, is independently selected from H, halogen, CN, NO$_2$, =O, C(=O)NR$^a$R$^a$, C(=O)OR$^b$, Si(C$_{1-4}$ alkyl)$_3$, —(CH$_2$)$_n$—OR$^b$, —(CH$_2$)$_n$—NR$^a$R$^a$, C(=NOH)NH$_2$, C$_{1-6}$ alkyl substituted with 0-5 R$^e$, C$_{2-6}$ alkenyl substituted with 0-5 R$^e$, C$_{2-6}$ alkynyl substituted with 0-5 $R^e$, aryl substituted with 0-5 $R^e$, —$(CH_2)_n$—$C_{3-6}$ cycloalkyl substituted with 0-5 $R^e$, —$(CH_2)_n$—O-4- to 10-membered heterocyclyl substituted with 0-5 $R^e$;

$R^a$, at each occurrence, is independently selected from H, $C_{1-6}$ alkyl substituted with 0-5 $R^e$, $C_{2-6}$ alkenyl substituted with 0-5 $R_e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R_e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^d$, at each occurrence, is independently selected from H and $C_{1-4}$alkyl substituted with 0-5 $R^e$;

$R^e$, at each occurrence, is independently selected from F, Cl, Br, CN, $NO_2$, =O, $C_{1-6}$ alkyl substituted with 0-5 $R^f$, $C_{2-6}$ alkenyl, $C_{2-6}$ alkynyl, —$(CH_2)_n$—$C_{3-6}$ cycloalkyl, —$(CH_2)_n$-aryl, —$(CH_2)_n$-heterocyclyl, $CO_2H$, —$(CH_2)_nOR^f$, $SR^f$, and —$(CH_2)_nNR^fR^f$;

$R^f$, at each occurrence, is independently selected from H, $C_{1-5}$ alkyl optionally substituted with F, Cl, Br, $C_{3-6}$ cycloalkyl, and phenyl, or $R^f$ and $R^f$ together with the nitrogen atom to which they are both attached form a heterocyclic ring optionally substituted with $C_{1-4}$alkyl;

n, at each occurrence, is an integer independently selected from 0, 1, 2, 3, and 4; and p, at each occurrence, is an integer independently selected from 0, 1, and 2.

2. The compound of claim 1, or a stereoisomer, a tautomer, a pharmaceutically acceptable salt thereof, wherein:
A is independently selected from

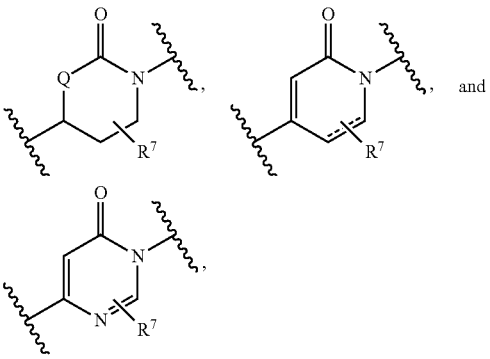

Ring B is independently selected from aryl and 5- to 6-membered heterocyclyl;
Q is independently selected from O, NH, and $CH_2$;
W is independently selected from $(CR^1R^2)_{1-2}$, O, NH, and $N(C_{1-4}$ alkyl);
X is independently selected from —$CH_2NH$—, —NHC(=O)- and —C(=O)NH—;

$R^1$ and $R^2$ are independently selected from H, halogen, $C_{1-4}$ alkyl, $OR^b$, and $C_{3-5}$ cycloalkyl;

$R^3$ is independently selected from H, $NO_2$, =O, halogen, $C_{1-4}$ alkyl substituted with 1-5 $R^5$, $C_{2-4}$ alkenyl substituted with 1-5 $R^5$, $C_{2-4}$ alkynyl substituted with 1-5 $R^5$, CN, —$OR^b$, —$NR^aR^a$, —$C(=O)R^b$, —$C(=O)OR^b$, —$NR^aC(=O)OR^b$, —$NR^aC(=O)R^b$, —$NR^aC(N=CN)NHR^a$, —$NR^aC(NH)NHR^a$, —N=$CR^bNR^aR^a$, —$NR^aC(=O)NR^aR^a$, —$C(=O)NR^aR^a$, —$NR^aC(=S)NR^aC(=O)R^b$, —$S(=O)_pR^c$, —$S(=O)_pNR^aR^a$, —$NR^aS(=O)_pNR^aR^a$, —$NR^aS(=O)_pR^c$, —$(CH_2)_n$—$C_{3-10}$ carbocyclyl substituted with 1-5 $R^5$, and —$(CH_2)_n$-4- to 10-membered heterocyclyl substituted with 1-5 $R^5$; optionally, two adjacent $R^3$ groups on the carbocyclyl and heterocyclyl may form a ring substituted with 1-5 $R^5$;

$R^4$ is independently selected from H, halogen, CN, $C_{1-6}$ alkyl substituted with 1-5 $R^{10}$, —$OR^b$, —$(CH_2)_n$-aryl substituted with 1-5 $R^{10}$, —$(CH_2)_n$—$C_{3-6}$ cycloalkyl substituted with 1-5 $R^{10}$, and —$(CH_2)_n$-4-6 membered heterocyclyl substituted with 1-5 $R^{10}$;

$R^5$, at each occurrence, is independently selected from H, D, —$(CH_2)_n$—$OR^b$, =O, —$(CH_2)_nNH_2$, —$(CH_2)_nCN$, halogen, $C_{1-6}$ alkyl, —$(CH_2)_n$—$C(=O)OR^b$, —$(CH_2)_n$—$OR^b$, —$(CH_2)_n$—$C_{3-10}$ carbocyclyl substituted with 0-5 $R^e$, —$(CH_2)_n$-4- to 10-membered heterocyclyl substituted with 0-5 $R^e$, and —O-4- to 10-membered heterocyclyl substituted with 0-5 $R^e$;

$R^7$ is independently selected from H, $OR^b$, halogen, $NR^aR^a$, and $C_{1-3}$ alkyl;

$R^{10}$, at each occurrence, is independently selected from H, halogen, CN, $NO_2$, =O, $C(=O)NR^aR^a$, $C(=O)OR^b$, $Si(C_{1-4}$ alkyl$)_3$, —$(CH_2)_n$—$OR^b$, —$(CH_2)_n$—$NR^aR^a$, $C(=NOH)NH_2$, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, aryl substituted with 0-5 $R^e$, —$(CH_2)_n$—$C_{3-6}$ cycloalkyl substituted with 0-5 $R^e$, —$(CH_2)_n$—O-4- to 10-membered heterocyclyl substituted with 0-5 $R^e$;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^e$, at each occurrence, is independently selected from F, Cl, Br, CN, $NO_2$, =O, $C_{1-6}$ alkyl substituted with 0-5 $R^f$, $C_{2-6}$ alkenyl, $C_{2-6}$ alkynyl, —$(CH_2)_n$—$C_{3-6}$ cycloalkyl, —$(CH_2)_n$-aryl, —$(CH_2)_n$-heterocyclyl, $CO_2H$, —$(CH_2)_nOR^f$, $SR^f$, and —$(CH_2)_nNR^fR^f$;

$R^f$, at each occurrence, is independently selected from H, $C_{1-5}$ alkyl optionally substituted with F, Cl, Br, $C_{3-6}$ cycloalkyl, and phenyl, or $R^f$ and $R^f$ together with the nitrogen atom to which they are both attached form a heterocyclic ring optionally substituted with $C_{1-4}$alkyl;

n, at each occurrence, is an integer independently selected from 0, 1, 2, 3, and 4; and p, at each occurrence, is an integer independently selected from 0, 1, and 2.

3. The compound having Formula (II):

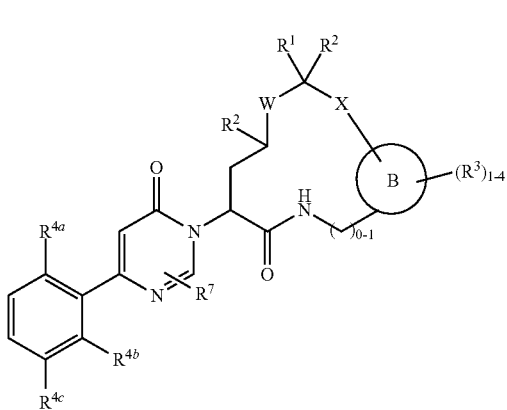

(II)

or a stereoisomer, a tautomer, a pharmaceutically acceptable salt thereof, wherein:

Ring B is independently selected from aryl and 5- to 6-membered heterocyclyl;

W is independently selected from $(CHR^{1a})_{1-2}$, O, NH, and $N(C_{1-4}\text{ alkyl})$;

X is independently selected from —NHC(=O)- and —C(=O)NH—;

$R^1$ is independently selected from H and $C_{1-4}$ alkyl;

$R^{1a}$ is independently selected from H, F, $CH_3$, and OH;

$R^2$ is independently selected from H and OH;

$R^3$ is independently selected from H, =O, halogen, $C_{1-4}$ alkyl substituted with 1-5 $R^5$, CN, —$OR^b$, —$NR^aR^a$, —C(=O)$R^b$, —C(=O)$OR^b$, —$NR^aC(=O)OR^b$, —$NR^aC(=O)R^b$, —$NR^aC(=O)NR^aR^a$, —C(=O)$NR^aR^a$, —$S(=O)_pR^c$, —$(CH_2)_n$—$C_{3-10}$ carbocyclyl substituted with 1-5 $R^5$, and —$(CH_2)_n$-4- to 10-membered heterocyclyl substituted with 1-5 $R^5$; optionally, two adjacent $R^3$ groups on the carbocyclyl and heterocyclyl may form a ring substituted with 1-5 $R^5$;

$R^{4a}$ is independently selected from H, halogen, CN, $OCH_3$, $OCF_3$, $CH_3$, C(=O)$CH_3$, $CHF_2$, $CF_3$, $CCH_3F_2$, $OCHF_2$, aryl, $C_{3-6}$ cycloalkyl, and 4-6 membered heterocycle, wherein said aryl, cycloalkyl and heterocycle is optionally substituted with $R^{10}$;

$R^{4b}$ is independently selected from H and halogen;

$R^{4c}$ is independently selected from H, F, Cl, methyl, ethyl, isopropyl, and $OCH_3$;

$R^5$, at each occurrence, is independently selected from H, D, —$(CH_2)_n$—$OR^b$, =O, —$(CH_2)_nNH_2$, —$(CH_2)_nCN$, halogen, $C_{1-6}$ alkyl, —$(CH_2)_n$—C(=O)$OR^b$, —$(CH_2)_n$—$OR^b$, —$(CH_2)_n$—$C_{3-10}$ carbocyclyl substituted with 0-5 $R^e$, —$(CH_2)_n$-4- to 10-membered heterocyclyl substituted with 0-5 $R^e$, and —O-4- to 10-membered heterocyclyl substituted with 0-5 $R^e$;

$R^7$ is independently selected from H, $OR^b$, halogen, $NR^aR^a$, and $C_{1-3}$ alkyl;

$R^{10}$, at each occurrence, is independently selected from H, halogen, CN, $NO_2$, =O, C(=O)$NR^aR^a$, C(=O)$OR^b$, $Si(C_{1-4}\text{ alkyl})_3$, —$(CH_2)_n$—$OR^b$, —$(CH_2)_n$—$NR^aR^a$, C(=NOH)$NH_2$, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, aryl substituted with 0-5 $R^e$, —$(CH_2)_n$—$C_{3-6}$ cycloalkyl substituted with 0-5 $R^e$, —$(CH_2)_n$—O-4- to 10-membered heterocyclyl substituted with 0-5 $R^e$;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^e$, at each occurrence, is independently selected from F, Cl, Br, CN, $NO_2$, =O, $C_{1-6}$ alkyl substituted with 0-5 $R^f$, $C_{2-6}$ alkenyl, $C_{2-6}$ alkynyl, —$(CH_2)_n$—$C_{3-6}$ cycloalkyl, —$(CH_2)_n$-aryl, —$(CH_2)_n$-heterocyclyl, $CO_2H$, —$(CH_2)_nOR^f$, $SR^f$, and —$(CH_2)_nNR^fR^f$;

$R^f$, at each occurrence, is independently selected from H, $C_{1-5}$ alkyl optionally substituted with F, Cl, Br, $C_{3-6}$ cycloalkyl, and phenyl, or $R^f$ and $R^f$ together with the nitrogen atom to which they are both attached form a heterocyclic ring optionally substituted with $C_{1-4}$alkyl;

n, at each occurrence, is an integer independently selected from 0, 1, 2, 3, and 4; and p, at each occurrence, is an integer independently selected from 0, 1, and 2.

4. The compound of claim 3, or a stereoisomer, a tautomer, a pharmaceutically acceptable salt thereof, wherein: ring B is independently selected from

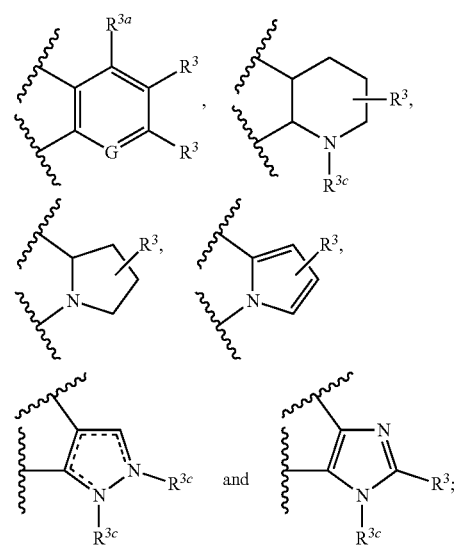

G is independently selected from N and $CR^{3b}$;

$R^3$ is independently selected from H, =O, halogen, $C_{1-4}$ alkyl substituted with 1-5 $R^5$, CN, —$OR^b$, —$NR^aR^a$, —C(=O)$R^b$, —C(=O)$OR^b$, —$NR^aC(=O)OR^b$, —$NR^aC(=O)R^b$, —$NR^aC(=O)NR^aR^a$, —C(=O)

NR$^a$R$^a$, —S(=O)$_p$R$^c$, —(CH$_2$)$_n$—C$_{3-10}$ carbocyclyl substituted with 1-5 R$^5$, and —(CH$_2$)$_n$-4- to 10-membered heterocyclyl substituted with 1-5 R$^5$;

R$^{3a}$ is independently selected from H and halogen;

R$^{3b}$ is independently selected from H, halogen, methyl, and CN;

R$^{3c}$ is independently selected from H, C$_{1-4}$alkyl substituted with 1-4 R$^5$, —(CH$_2$)$_n$—C(=O)R$^b$, —(CH$_2$)$_n$—C(=O)OR$^b$; provided when one R$^{3c}$ is present, the other is absent;

R$^{4a}$ is independently selected from H, F, Cl, Br, CN, OCH$_3$, OCF$_3$, CH$_3$, C(=O)CH$_3$, CHF$_2$, CF$_3$, CCH$_3$F$_2$, OCHF$_2$, phenyl, C$_{3-6}$ cycloalkyl, and 4-6 membered heterocycle, wherein said phenyl, cycloalkyl and heterocycle is optionally substituted with R$^{10}$;

R$^{4b}$ is independently selected from H and F;

R$^{4c}$ is independently selected from H, F, Cl, methyl, ethyl, isopropyl, and OCH$_3$;

R$^5$, at each occurrence, is independently selected from H, D, —OR$^b$, —NH$_2$, —CN, halogen, C$_{1-6}$ alkyl, —C(=O)OR$^b$, C$_{3-10}$ carbocyclyl substituted with 0-5 R$^e$, -4- to 10-membered heterocyclyl substituted with 0-5 R$^e$, and —O-4- to 10-membered heterocyclyl substituted with 0-5 R$^e$; and R$^{10}$, at each occurrence, is independently selected from H, halogen, CN, NO$_2$, =O, C(=O)NR$^a$R$^a$, C(=O)OR$^b$, Si(C$_{1-4}$ alkyl)$_3$, —(CH$_2$)$_n$—OR$^b$, —(CH$_2$)$_n$—NR$^a$R$^a$, C(=NOH)NH$_2$, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, aryl substituted with 0-5 R$^e$, —(CH$_2$)$_n$—C$_{3-6}$ cycloalkyl substituted with 0-5 R$^e$, —(CH$_2$)$_n$—O-4- to 10-membered heterocyclyl substituted with 0-5 R$^e$.

5. The compound of claim 4, or a stereoisomer, a tautomer, a pharmaceutically acceptable salt thereof, wherein:

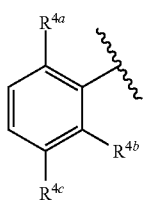

is independently selected from

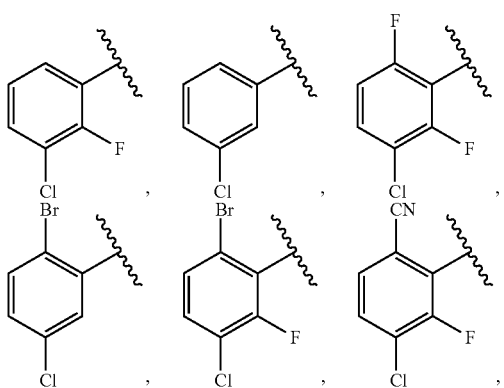

-continued

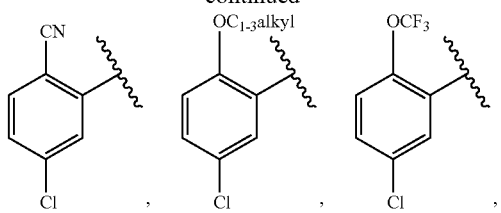

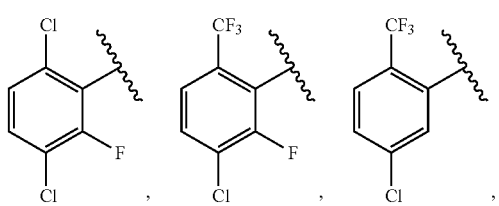

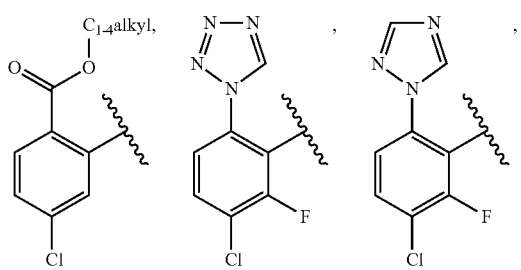

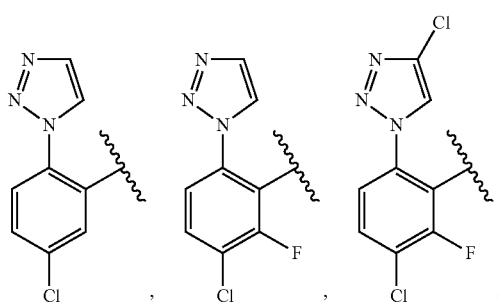

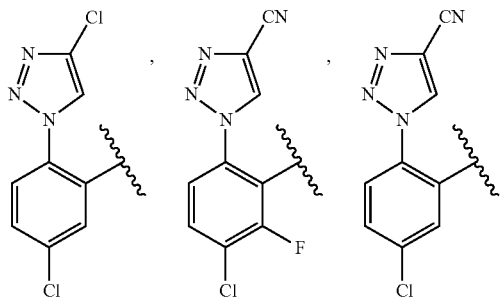

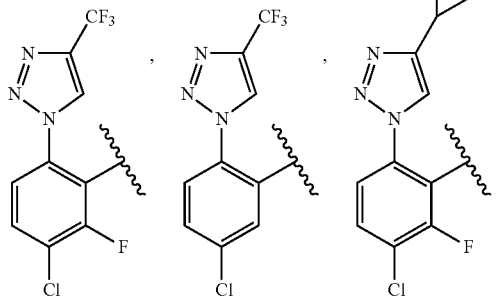

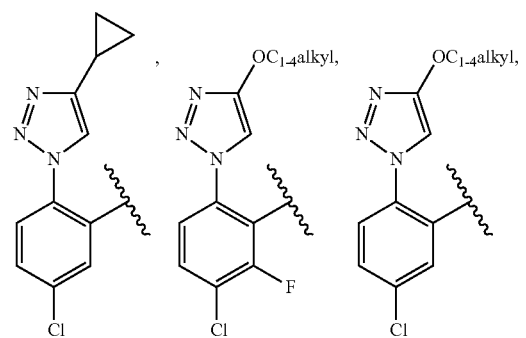
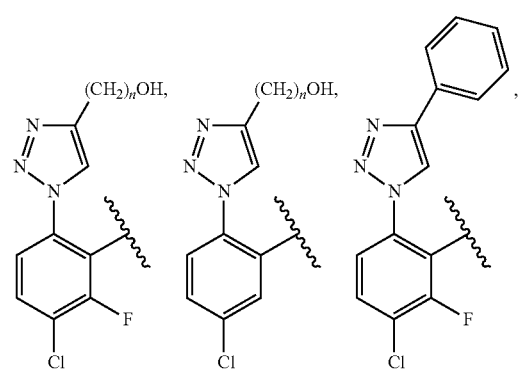
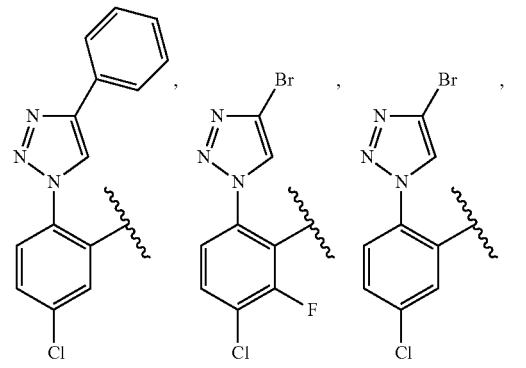
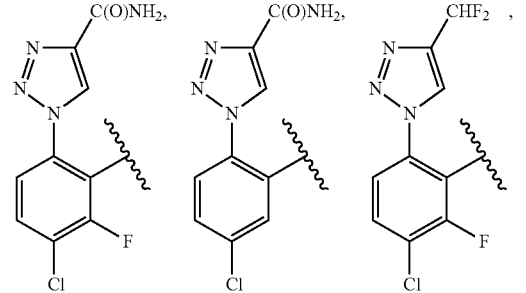
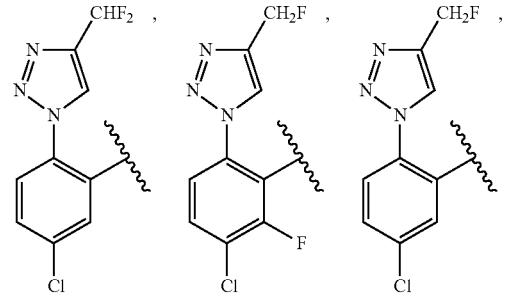
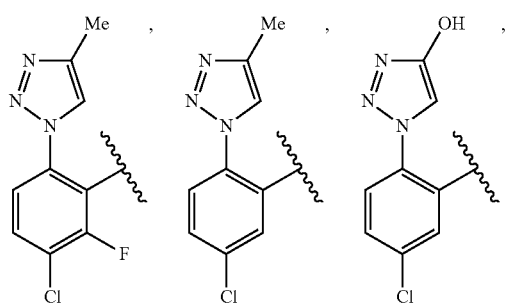
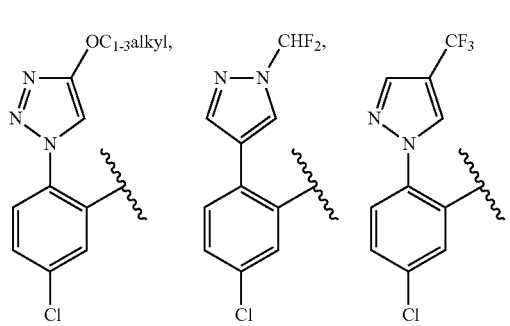
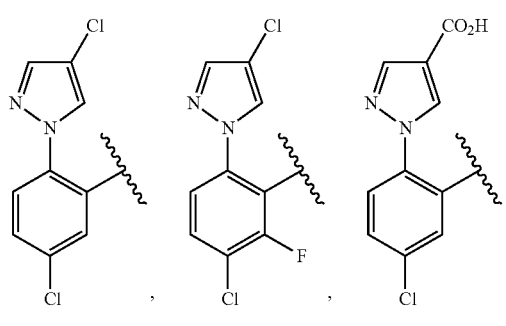
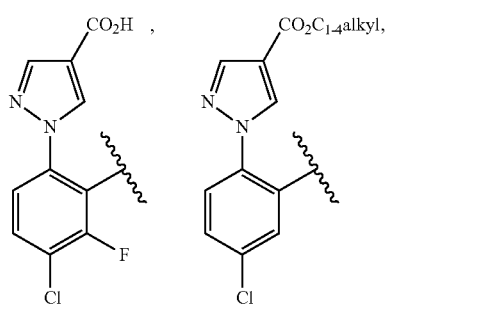
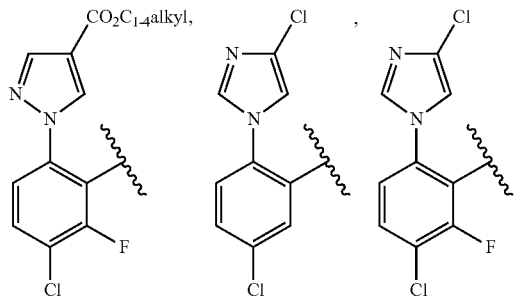

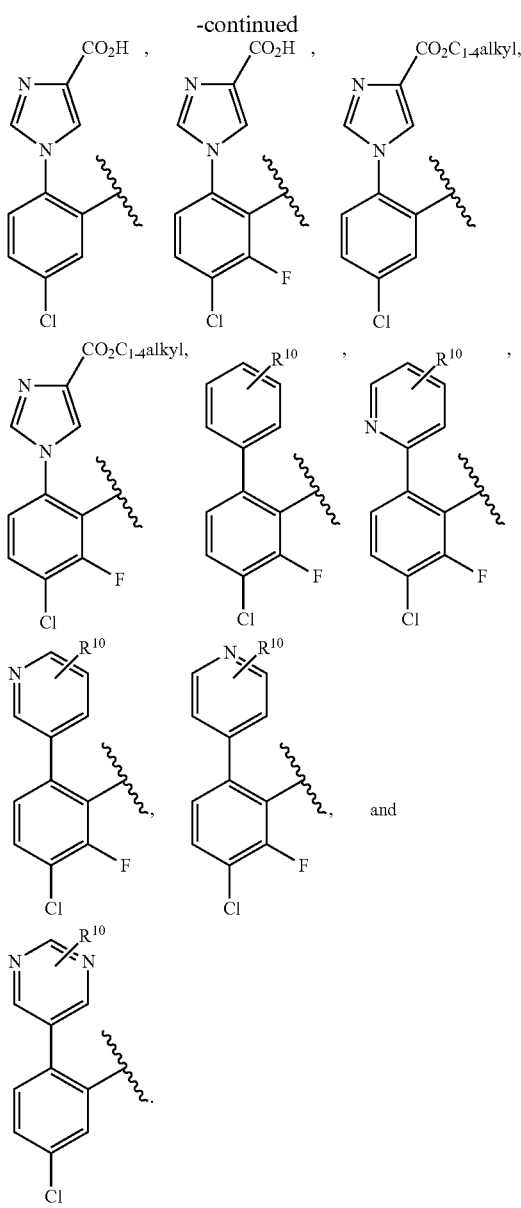

6. The compound of claim 5, having Formula (III):

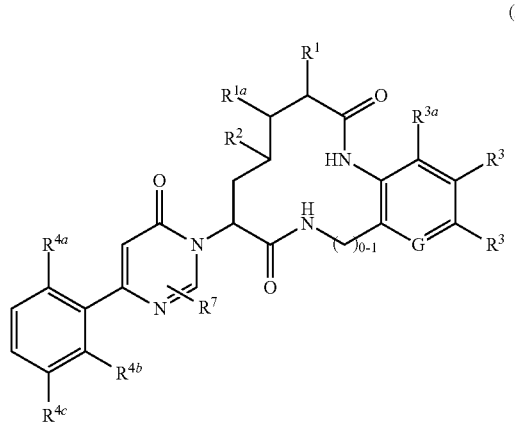

or a stereoisomer, a tautomer, a pharmaceutically acceptable salt thereof, wherein:

G is independently selected from N and $CR^{3b}$;

$R^1$ is independently selected from H and $CH_3$;

$R^{1a}$ is independently selected from H, F, $CH_3$, and OH;

$R^2$ is independently selected from H and OH;

$R^{3a}$ is independently selected from H and halogen;

$R^{3b}$ is independently selected from H, halogen, methyl, and CN;

$R^3$ is independently selected from H, halogen, $C_{1-4}$ alkyl substituted with 1-5 $R^5$, CN, —$OR^b$, —$NR^aR^a$, —C(=O)$R^b$, —C(=O)$OR^b$, —$NR^aC(=O)OR^b$, —$NR^aC(=O)R^b$, —$NR^aC(=O)NR^aR^a$, —C(=O)$NR^aR^a$, —S(=O)$_pR^c$, —$(CH_2)_n$—$C_{3-10}$ carbocyclyl substituted with 1-5 $R^5$, and —$(CH_2)_n$-4- to 10-membered heterocyclyl substituted with 1-5 $R^5$;

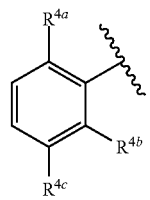

is independently selected from

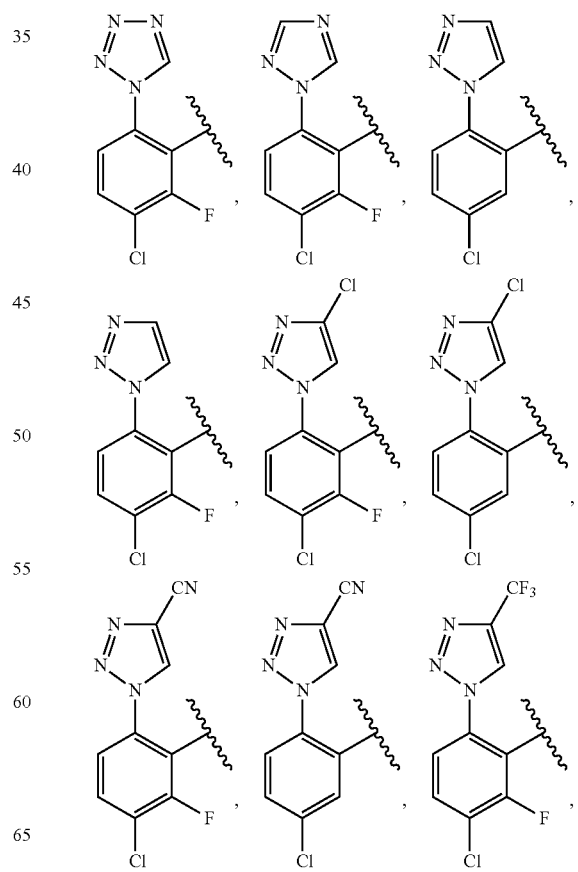

-continued

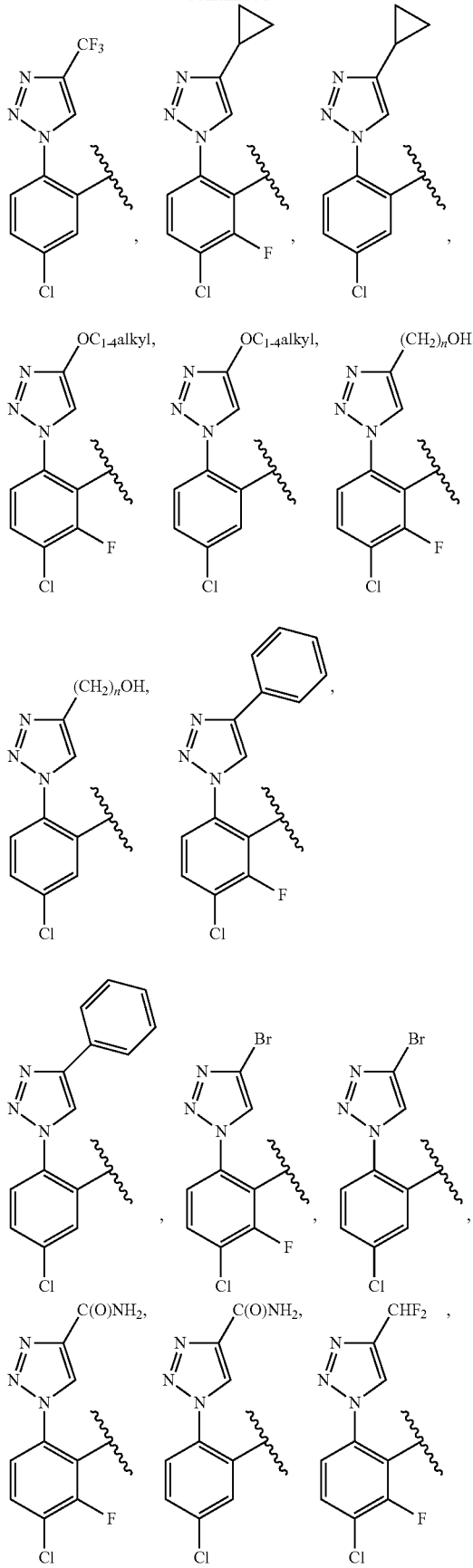

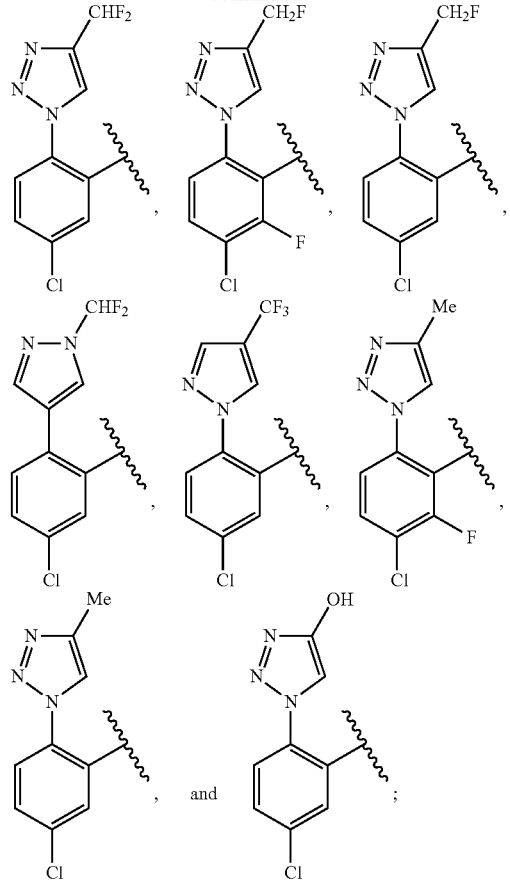

R[5], at each occurrence, is independently selected from H, D, —OR[b], —NH$_2$, —CN, halogen, C$_{1-6}$ alkyl, —C(═O)OR[b], C$_{3-10}$ carbocyclyl substituted with 0-5 R[e], -4- to 10-membered heterocyclyl substituted with 0-5 R[e], and —O-4- to 10-membered heterocyclyl substituted with 0-5 R[e];

R[7] is independently selected from H, OH, halogen, NR[a]R[a], and C$_{1-3}$ alkyl;

R[a], at each occurrence, is independently selected from H, C$_{1-6}$ alkyl substituted with 0-5 R[e], C$_{2-6}$ alkenyl substituted with 0-5 R[e], C$_{2-6}$ alkynyl substituted with 0-5 R[e], —(CH$_2$)$_n$—C$_{3-10}$carbocyclyl substituted with 0-5 R[e], and —(CH$_2$)$_n$-heterocyclyl substituted with 0-5 R[e]; or R[a] and R[a] together with the nitrogen atom to which they are both attached form a heterocyclic ring substituted with 0-5 R[e];

R[b], at each occurrence, is independently selected from H, C$_{1-6}$ alkyl substituted with 0-5 R[e], C$_{2-6}$ alkenyl substituted with 0-5 R[e], C$_{2-6}$ alkynyl substituted with 0-5 R[e], —(CH$_2$)$_n$—C$_{3-10}$carbocyclyl substituted with 0-5 R[e], and —(CH$_2$)$_n$-heterocyclyl substituted with 0-5 R[e];

R[c], at each occurrence, is independently selected from C$_{1-6}$ alkyl substituted with 0-5 R[e], C$_{2-6}$alkenyl substituted with 0-5 R[e], C$_{2-6}$ alkynyl substituted with 0-5 R[e], C$_{3-6}$carbocyclyl, and heterocyclyl;

R[e], at each occurrence, is independently selected from F, Cl, Br, CN, NO$_2$, ═O, C$_{1-6}$ alkyl substituted with 0-5 R[f], C$_{2-6}$ alkenyl, C$_{2-6}$ alkynyl, —(CH$_2$)$_n$—C$_{3-6}$ cycloalkyl, —(CH$_2$)$_n$-aryl, —(CH$_2$)$_n$-heterocyclyl, CO$_2$H, —(CH$_2$)$_n$OR[f], SR[f], and —(CH$_2$)$_n$NR[f]R[f];

$R^f$, at each occurrence, is independently selected from H, $C_{1-5}$ alkyl optionally substituted with F, Cl, Br, $C_{3-6}$ cycloalkyl, and phenyl, or $R^f$ and $R^f$ together with the nitrogen atom to which they are both attached form a heterocyclic ring optionally substituted with $C_{1-4}$ alkyl;

n, at each occurrence, is an integer independently selected from 0, 1, 2, 3, and 4;

p, at each occurrence, is an integer independently selected from 0, 1, and 2.

7. The compound of claim 6, or a stereoisomer, a tautomer, a pharmaceutically acceptable salt thereof, wherein:

G is $CR^{3b}$;

$R^1$ is independently selected from H and $CH_3$;

$R^{1a}$ is independently selected from H, F, $CH_3$, and OH;

$R^2$ is independently selected from H and OH;

$R^{3a}$ is H;

$R^{3b}$ is independently selected from H, halogen, methyl, and CN;

$R^3$ is independently selected from H, =O, F, $CHF_2$, $CF_3$, $OCF_3$, $OCHF_2$, $CH_3$, CN, —$(CH_2)_{0-2}$—OH, $OC_{1-4}$ alkyl, $C(=O)C_{1-4}$ alkyl, —$(CH_2)_{0-1}$—$C(=O)OH$, —$C(=O)OC_{1-4}$ alkyl, —$S(=O)_2C_{1-4}$ alkyl, and —$NHC(=O)OC_{1-4}$ alkyl;

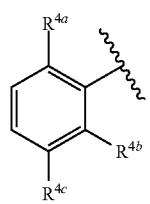

is independently selected from

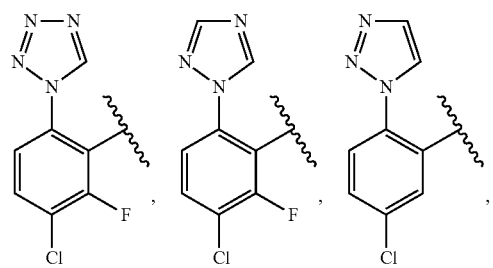

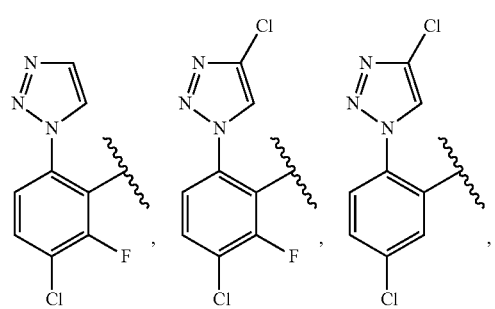

-continued

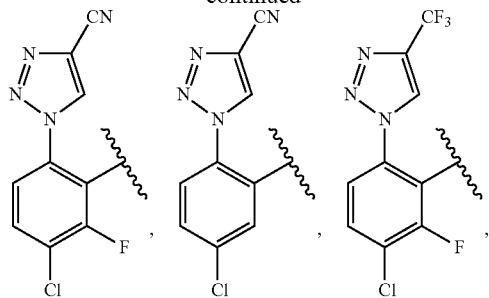

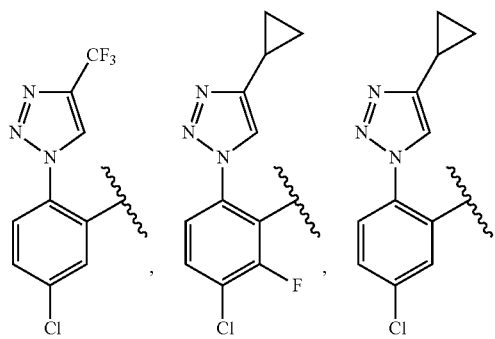

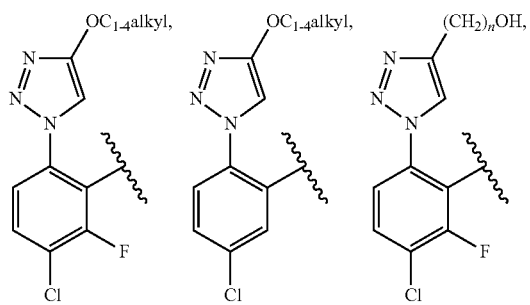

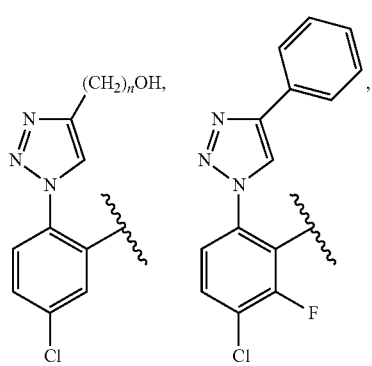

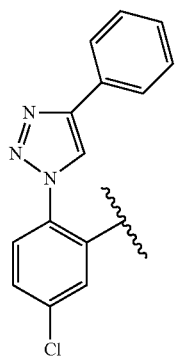

-continued

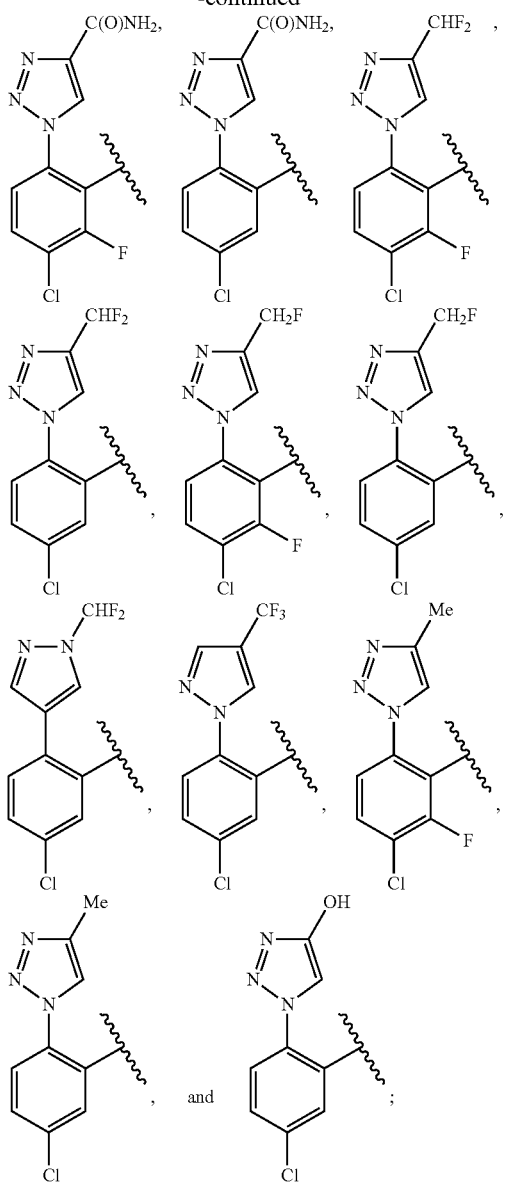

, and ;

R[7] is independently selected from H, OH, halogen, and $C_{1-3}$ alkyl;

R[a], at each occurrence, is independently selected from H, $C_{1-6}$ alkyl substituted with 0-5 R[e], $C_{2-6}$ alkenyl substituted with 0-5 R[e], $C_{2-6}$ alkynyl substituted with 0-5 R[e], —$(CH_2)_n$—$C_{3-10}$carbocyclyl substituted with 0-5 R[e], and —$(CH_2)_n$-heterocyclyl substituted with 0-5 R[e]; or R[a] and R[a] together with the nitrogen atom to which they are both attached form a heterocyclic ring substituted with 0-5 R[e];

R[b], at each occurrence, is independently selected from H, $C_{1-6}$ alkyl substituted with 0-5 R[e], $C_{2-6}$ alkenyl substituted with 0-5 R[e], $C_{2-6}$ alkynyl substituted with 0-5 R[e], —$(CH_2)_n$—$C_{3-10}$carbocyclyl substituted with 0-5 R[e], and —$(CH_2)_n$-heterocyclyl substituted with 0-5 R[e];

R[c], at each occurrence, is independently selected from $C_{1-6}$ alkyl substituted with 0-5 R[e], $C_{2-6}$alkenyl substituted with 0-5 R[e], $C_{2-6}$alkynyl substituted with 0-5 R[e], $C_{3-6}$carbocyclyl, and heterocyclyl;

R[e], at each occurrence, is independently selected from F, Cl, Br, CN, $NO_2$, =O, $C_{1-6}$ alkyl substituted with 0-5 R[f], $C_{2-6}$ alkenyl, $C_{2-6}$ alkynyl, —$(CH_2)_n$—$C_{3-6}$cycloalkyl, —$(CH_2)_n$-aryl, —$(CH_2)_n$-heterocyclyl, $CO_2H$, —$(CH_2)_nOR^f$, $SR^f$, and —$(CH_2)_nNR^fR^f$;

R[f], at each occurrence, is independently selected from H, $C_{1-5}$ alkyl optionally substituted with F, Cl, Br, $C_{3-6}$ cycloalkyl, and phenyl, or R[f] and R[f] together with the nitrogen atom to which they are both attached form a heterocyclic ring optionally substituted with $C_{1-4}$alkyl;

n, at each occurrence, is an integer independently selected from 0, 1, 2, 3, and 4; and p, at each occurrence, is an integer independently selected from 0, 1, and 2.

8. The compound of claim 4, or a stereoisomer, a tautomer, a pharmaceutically acceptable salt thereof, wherein:

G is $CR^{3b}$;
R[1] is independently selected from H and $CH_3$;
$R^{1a}$ is H;
R[2] is H;
$R^{3a}$ is H;
$R^{3b}$ is H;
R[3] is independently selected from H, F, Cl, CN, $C_{1-4}$alkyl substituted with 1-4 R[5], $C(=O)R^b$, $C(=O)OR^b$, —$S(=O)_2R^c$, and —$NHC(=O)OR^b$;

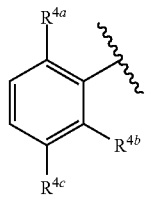

is independently selected from

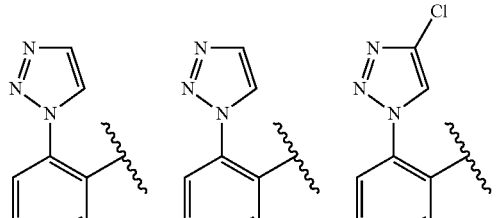

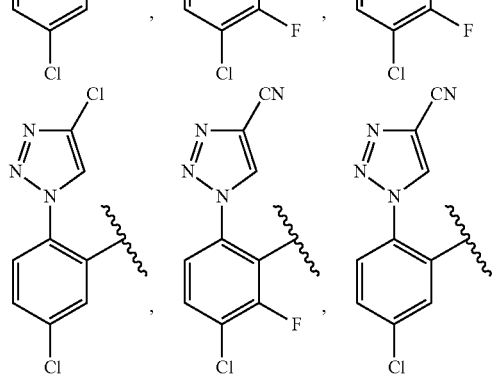

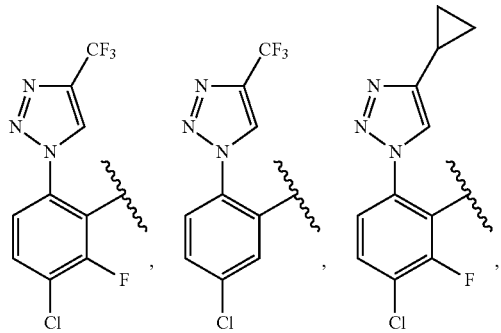

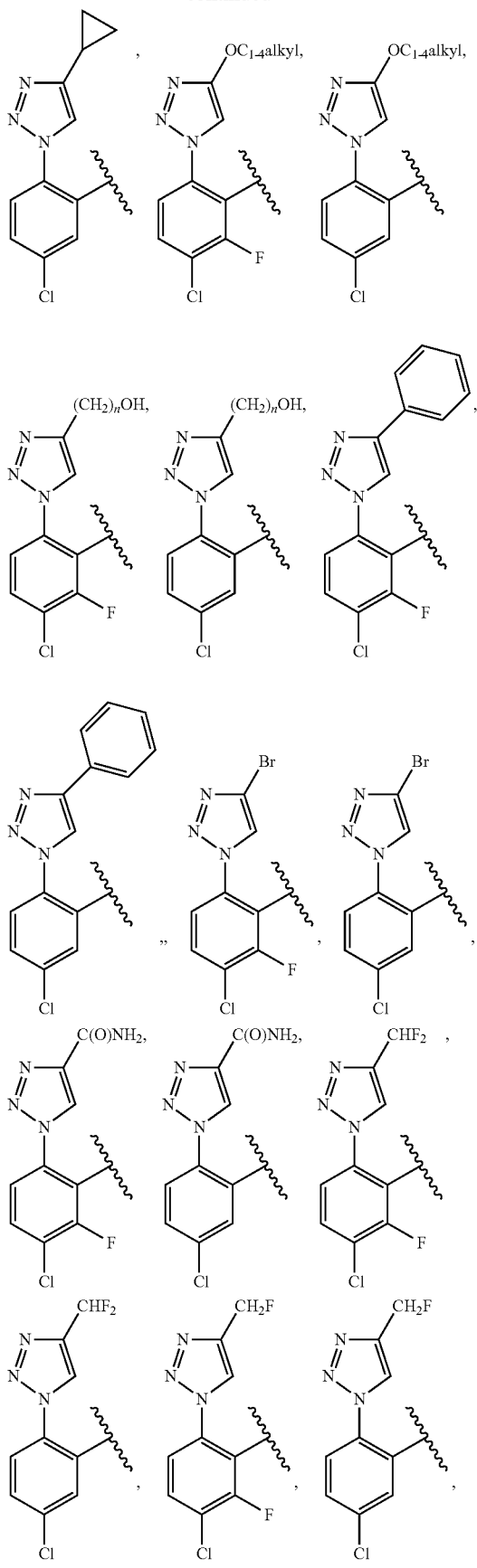

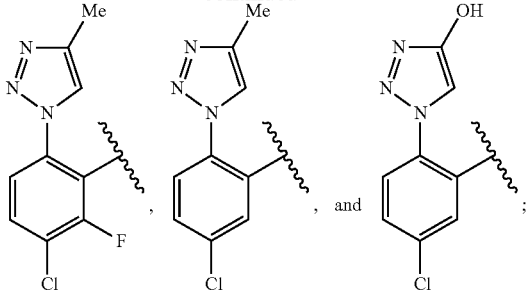

R[5], at each occurrence, is independently selected from H, D, —OR[b], —NH$_2$, —CN, halogen, C$_{1-6}$ alkyl, —C(=O)OR[b], C$_{3-10}$ carbocyclyl substituted with 0-5 R[e], -4- to 10-membered heterocyclyl substituted with 0-5 R[e], and —O-4- to 10-membered heterocyclyl substituted with 0-5 R[e];

R[7] is H;

R[b], at each occurrence, is independently selected from H and C$_{1-6}$ alkyl substituted with 0-5 R[e];

R[c], at each occurrence, is C$_{1-6}$ alkyl substituted with 0-5 R[e];

R[e], at each occurrence, is independently selected from F, Cl, Br, CN, NO$_2$, =O, C$_{1-6}$ alkyl substituted with 0-5 R[f], C$_{2-6}$ alkenyl, C$_{2-6}$ alkynyl, —(CH$_2$)$_n$—C$_{3-6}$ cycloalkyl, —(CH$_2$)$_n$-aryl, —(CH$_2$)$_n$-heterocyclyl, CO$_2$H, —(CH$_2$)$_n$OR[f], SR[f], and —(CH$_2$)$_n$NR[f]R[f];

R[f], at each occurrence, is independently selected from H, C$_{1-5}$ alkyl optionally substituted with F, Cl, Br, C$_{3-6}$ cycloalkyl, and phenyl;

n, at each occurrence, is an integer independently selected from 0, 1, 2, 3, and 4; and p, at each occurrence, is an integer independently selected from 0, 1, and 2.

9. The compound of claim 4, having Formula (IV):

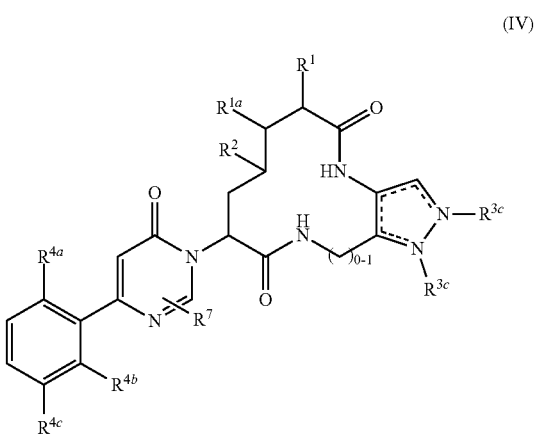

(IV)

or a stereoisomer, a tautomer, a pharmaceutically acceptable salt thereof, wherein:

R[1] is independently selected from H and CH$_3$;

R[1a] is independently selected from H, F, CH$_3$, and OH;

R[2] is independently selected from H and OH;

R[3c] is independently selected from H, and C$_{1-4}$ alkyl substituted with 1-4 R[5]; provided when one R[3c] is present, the other is absent;

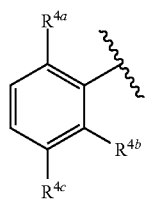
is independently selected from
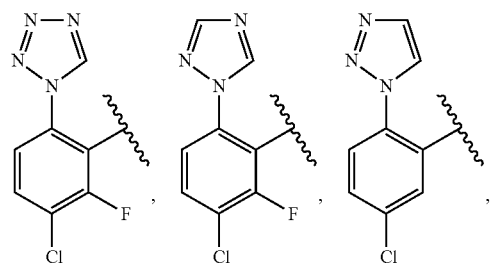
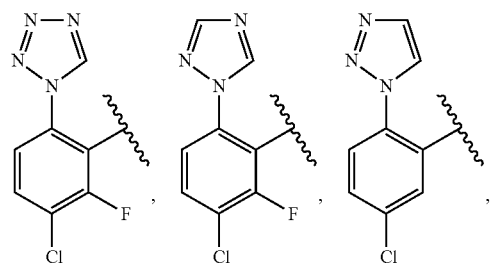
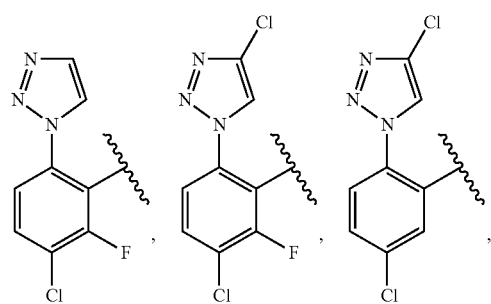
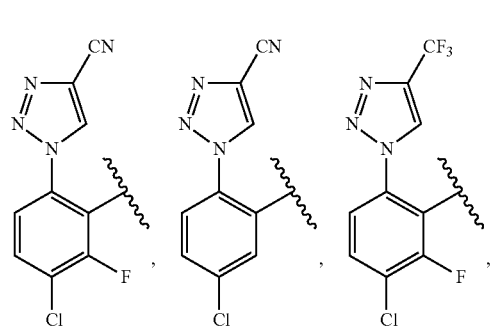
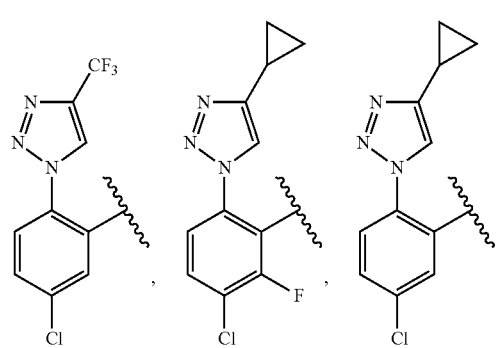
-continued
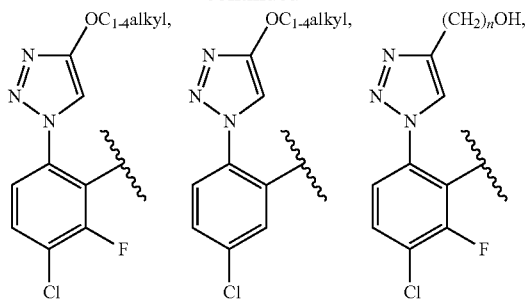
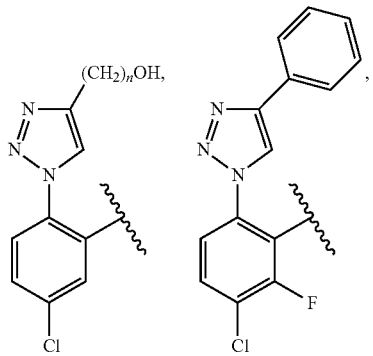
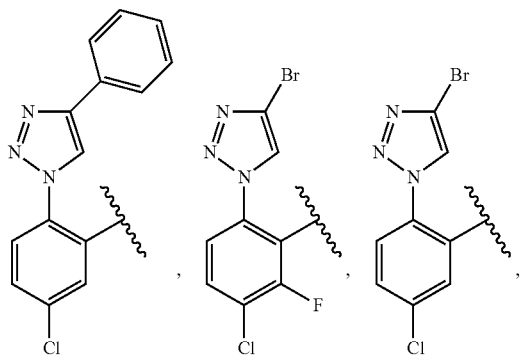
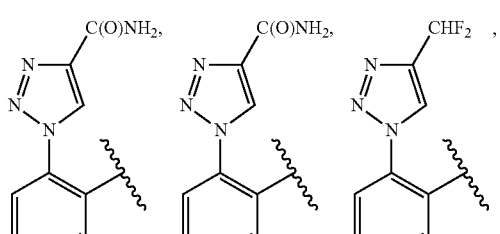
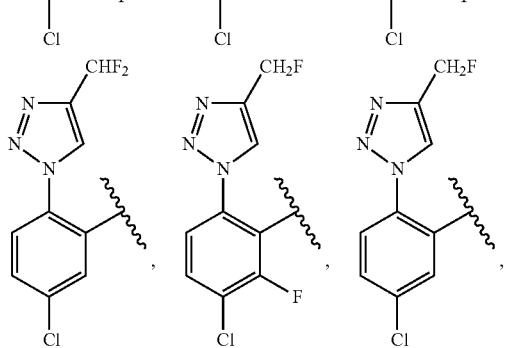

145

-continued

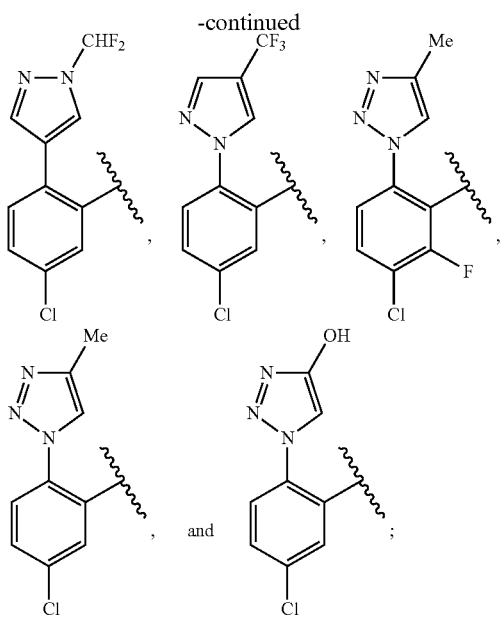

, and ;

R⁵, at each occurrence, is independently selected from H, D, —OR$^b$, —NH$_{12}$, —CN, F, Cl, Br, C$_{1-6}$ alkyl, —C(=O)OR$^b$, C$_{3-10}$ carbocyclyl substituted with 0-5 R$^e$, -4- to 10-membered heterocyclyl substituted with 0-5 R$^e$, and —O-4- to 10-membered heterocyclyl substituted with 0-5 R$^e$;

R⁷ is independently selected from H, OR$^b$, halogen, NR$^a$R$^a$, and C$_{1-3}$ alkyl;

R$^a$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^c$, at each occurrence, is independently selected from C$_{1-6}$ alkyl substituted with 0-5 R$^e$, C$_{2-6}$alkenyl substituted with 0-5 R$^e$, C$_{2-6}$alkynyl substituted with 0-5 R$^e$, C$_{3-6}$carbocyclyl, and heterocyclyl;

R$^e$, at each occurrence, is independently selected from F, Cl, Br, CN, NO$_2$, =O, C$_{1-6}$ alkyl substituted with 0-5 R$^f$, C$_{2-6}$ alkenyl, C$_{2-6}$ alkynyl, —(CH$_2$)$_n$—C$_{3-6}$ cycloalkyl, —(CH$_2$)$_n$-aryl, —(CH$_2$)$_n$-heterocyclyl, CO$_2$H, —(CH$_2$)$_n$OR$^f$, SR$^f$, and —(CH$_2$)$_n$NR$^f$R$^f$;

R$^f$, at each occurrence, is independently selected from H, C$_{1-5}$ alkyl optionally substituted with F, Cl, Br, C$_{3-6}$ cycloalkyl, and phenyl, or R$^f$ and R$^f$ together with the nitrogen atom to which they are both attached form a heterocyclic ring optionally substituted with C$_{1-4}$alkyl; and n, at each occurrence, is an integer independently selected from 0, 1, 2, 3, and 4.

146

10. The compound of claim 4, having Formula (V):

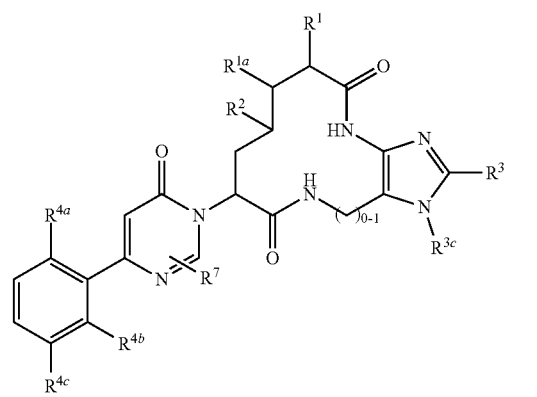

(V)

or a stereoisomer, a tautomer, a pharmaceutically acceptable salt thereof, wherein:

R$^1$ is independently selected from H and CH$_3$;

R$^{1a}$ is independently selected from H, F, CH$_3$, and OH;

R$^2$ is independently selected from H and OH;

R$^{3c}$ is independently selected from H, C$_{1-4}$alkyl substituted with 1-4 R$^5$, —(CH$_2$)$_n$—C(=O)R$^b$, —(CH$_2$)$_n$—C(=O)OR$^b$; provided when one R$^{3c}$ is present, the other is absent;

R$^3$ is independently selected from H, halogen, C$_{1-4}$ alkyl substituted with 1-5 R$^5$, CN, —OR$^b$, —NR$^a$R$^a$, —C(=O)R$^b$, —C(=O)OR$^b$, —NR$^a$C(=O)OR$^b$, —NR$^a$C(=O)R$^b$, —NR$^a$C(=O)NR$^a$R$^a$, —C(=O)NR$^a$R$^a$, —S(=O)$_p$R$^c$, —(CH$_2$)$_n$—C$_{3-10}$ carbocyclyl substituted with 1-5 R$^5$, and —(CH$_2$)$_n$-4- to 10-membered heterocyclyl substituted with 1-5 R$^5$;

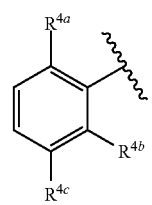

is independently selected from

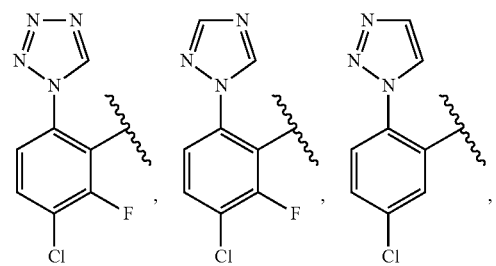

,

,

,

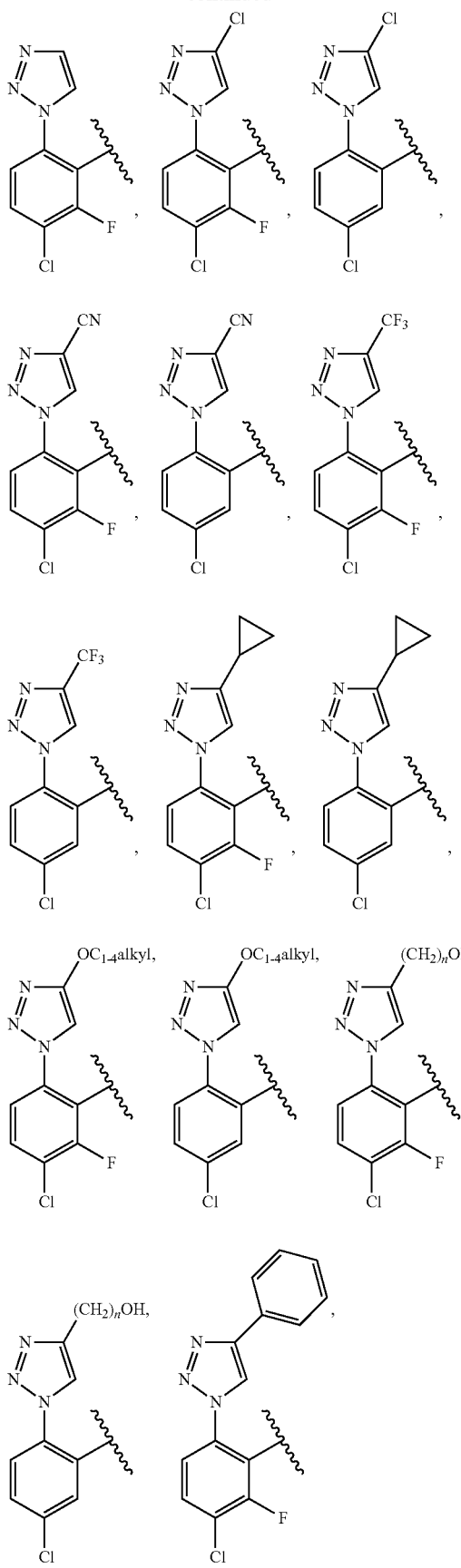
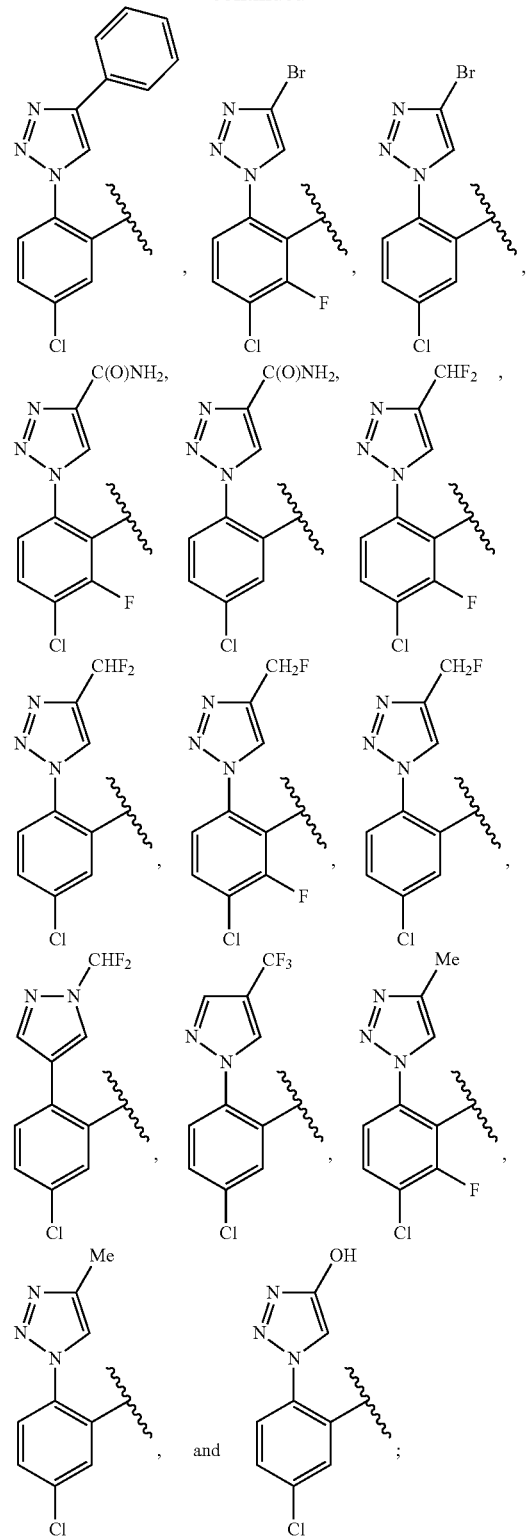
R[5], at each occurrence, is independently selected from H, —OR[b], —NH$_2$, —CN, halogen, C$_{1-6}$ alkyl, —C(=O)OR[b], C$_{3-10}$ carbocyclyl substituted with 0-5 R[e], -4- to 10-membered heterocyclyl substituted with 0-5 R[e], and —O-4- to 10-membered heterocyclyl substituted with 0-5 R[e];

R⁷ is independently selected from H, OR$^b$, halogen, NR$^a$R$^a$, and C$_{1-3}$ alkyl;

R$^a$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^c$, at each occurrence, is independently selected from C$_{1-6}$ alkyl substituted with 0-5 R$^e$, C$_{2-6}$alkenyl substituted with 0-5 R$^e$, C$_{2-6}$alkynyl substituted with 0-5 R$^e$, C$_{3-6}$carbocyclyl, and heterocyclyl;

R$^e$, at each occurrence, is independently selected from F, Cl, Br, CN, NO$_2$, =O, C$_{1-6}$ alkyl substituted with 0-5 R$^f$, C$_{2-6}$ alkenyl, C$_{2-6}$ alkynyl, —(CH$_2$)$_n$—C$_{3-6}$ cycloalkyl, —(CH$_2$)$_n$-aryl, —(CH$_2$)$_n$-heterocyclyl, CO$_2$H, —(CH$_2$)$_n$OR$^f$, SR$^f$, and —(CH$_2$)$_n$NR$^f$R$^f$;

R$^f$, at each occurrence, is independently selected from H, C$_{1-5}$ alkyl optionally substituted with F, Cl, Br, C$_{3-6}$ cycloalkyl, and phenyl, or R$^f$ and R$^f$ together with the nitrogen atom to which they are both attached form a heterocyclic ring optionally substituted with C$_{1-4}$alkyl; and n, at each occurrence, is an integer independently selected from 0, 1, 2, 3, and 4.

11. A pharmaceutical composition comprising one or more compounds according to claim 1 and a pharmaceutically acceptable carrier or diluent.

12. A method for the treatment of a thromboembolic disorder comprising administering to a patient in need thereof a therapeutically effective amount of a compound of claim 1.

13. The method of claim 12 wherein the thromboembolic disorder is selected from VTE, arterial cardiovascular thromboembolic disorders, venous cardiovascular thromboembolic disorders, and thromboembolic disorders in the chambers of the heart or in the peripheral circulation.

14. The compound of claim 1, selected from
(3R,7S)-7-(4-(5-Chloro-2-(4-(trifluoromethyl)-1H-1,2,3-triazol-1-yl)phenyl)-6-oxopyrimidin-1(6H)-yl)-3-methyl-4,5,6,7,9,10-hexahydrobenzo[b][1,5]-diazacyclododecine-2,8(1H,3H)-dione,
(3R,7S)-7-(4-(3-Chloro-6-(4-chloro-1H-1,2,3-triazol-1-yl)-2-fluorophenyl)-6-oxopyrimidin-1 (6H)-yl)-3-methyl-4,5,6,7,9,10-hexahydrobenzo[b][1,5]diazacyclo-dodecine-2,8(1H,3H)-dione,
(3R,7 S)-7-(4-(5-Chloro-2-(4-chloro-1H-1,2,3-triazol-1-yl)phenyl)-6-oxopyrimidin-1(6H)-yl)-3-methyl-4,5,6,7,9,10-hexahydrobenzo[b][1,5]diazacyclo-dodecine-2,8(1H,3H)-dione,
(3R,7S)-7-(4-(3-Chloro-2-fluoro-6-(4-(trifluoromethyl)-1H-1,2,3-triazol-1-yl)phenyl)-6-oxopyrimidin-1(6H)-yl)-3-methyl-4,5,6,7,9,10-hexahydrobenzo[b][1,5]-diazacyclododecine-2,8(1H,3H)-dione,
(3R,7S)-7-(4-(5-Chloro-2-(4-(difluoromethyl)-1H-1,2,3-triazol-1-yl)phenyl)-6-oxopyrimidin-1(6H)-yl)-3-methyl-4,5,6,7,9,10-hexahydrobenzo[b][1,5]diazacyclo-dodecine-2,8(1H,3H)-dione,
(3R,7S)-7-(4-(5-Chloro-2-(4-chloro-1H-1,2,3-triazol-1-yl)phenyl)-2-oxo-5,6-dihydropyridin-1(2H)-yl)-3-methyl-4,5,6,7,9,10-hexahydrobenzo[b][1,5]diazacyclododecine-2,8(1H,3H)-dione,
(3R,7 S)-7-(4-(3-Chloro-2,6-difluorophenyl)-2-oxo-5,6-dihydropyridin-1(2H)-yl)-3-methyl-4,5,6,7,9,10-hexahydrobenzo[b][1,5]diazacyclododecine-2,8(1H,3H)-dione,
(3R,7S)-7-(4-(5-Chloro-2-(4-(trifluoromethyl)-1H-1,2,3-triazol-1-yl)phenyl)-2-oxo-5,6-dihydropyridin-1(2H)-yl)-3-methyl-4,5,6,7,9,10-hexahydrobenzo[b][1,5]diazacyclododecine-2,8(1H,3H)-dione,
(3R,7 S)-7-(4-(5-Chloro-2-(4-chloro-1H-1,2,3-triazol-1-yl)phenyl)-2-oxopyridin-1(2H)-yl)-3-methyl-4,5,6,7,9,10-hexahydrobenzo[b][1,5]diazacyclododecine-2,8 (1H,3H)-dione,
(3R,7S)-7-(4-(5-Chloro-2-(4-(trifluoromethyl)-1H-1,2,3-triazol-1-yl)phenyl)-6-oxopyrimidin-1(6H)-yl)-12-fluoro-3-methyl-4,5,6,7,9,10-hexahydrobenzo[b][1,5] diazacyclododecine-2,8(1H,3H)-dione,
(3R,7S)-7-(4-(5-Chloro-2-(4-(trifluoromethyl)-1H-1,2,3-triazol-1-yl)phenyl)-2-oxo-5,6-dihydropyridin-1(2H)-yl)-12-fluoro-3-methyl-4,5,6,7,9,10-hexahydrobenzo[b][1,5]diazacyclododecine-2,8(1H,3H)-dione,
(3R,7S)-7-(4-(5-chloro-2-(4-(trifluoromethyl)-1H-1,2,3-triazol-1-yl)phenyl)-6-oxo-3,6-dihydropyridin-1(2H)-yl)-3,10-dimethyl-4,5,6,7,9,10-hexahydrobenzo[b][1,5]diazacyclododecine-2,8(1H, 3H)-dione,
(3R,7S)-7-(4-(5-Chloro-2-(4-(trifluoromethyl)-1H-1,2,3-triazol-1-yl)phenyl)-2-oxo-5,6-dihydropyridin-1(2H)-yl)-3,10-dimethyl-4,5,6,7,9,10-hexahydrobenzo[b][1,5]diazacyclododecine-2,8(1H, 3H)-dione,
1-(3-chloro-2-fluorophenyl)-N-((3R,7S)-3-methyl-2,8-dioxo-1,2,3,4,5,6,7,8,9,10-decahydrobenzo[b][1,5]diazacyclododecin-7-yl)-1H-1,2,3-triazole-4-carboxamide,
1-(3-chloro-2-fluorophenyl)-5-methyl-N-((3R,7 S)-3-methyl-2,8-dioxo-1,2,3,4,5,6,7,8,9,10-decahydrobenzo[b][1,5]diazacyclododecin-7-yl)-1H-imidazole-4-carboxamide,
(S)-1-(3-chloro-2-fluorophenyl)-N-(2,9-dioxo-1,2,3,4,5,6,7,8,9,10-decahydrobenzo[b][1,4]diazacyclododecin-3-yl)-1H-1,2,3-triazole-4-carboxamide,
(S)-3-(1-(3-chloro-2-fluorophenyl)-5-methyl-1H-pyrazole-4-carboxamido)-2,9-dioxo-1,2,3,4,5,6,7,8,9,10-decahydrobenzo[b][1,4]diazacyclododecine-12-carboxylic acid,
(S)-3-(4-(5-chloro-2-(4-(trifluoromethyl)-1H-1,2,3-triazol-1-yl)phenyl)-6-oxopyrimidin-1(6H)-yl)-2,9-dioxo-1,2,3,4,5,6,7,8,9,10-decahydrobenzo[b][1,4]diazacyclododecine-12-carboxylate, and
(S)-3-(4-(5-chloro-2-(4-(trifluoromethyl)-1H-1,2,3-triazol-1-yl)phenyl)-6-oxopyrimidin-1(6H)-yl)-2,9-dioxo-1,2,3,4,5,6,7,8,9,10O-decahydrobenzo[b][1,4]diazacyclododecine-12-carboxylic acid.

* * * * *